(12) United States Patent
Bruenker et al.

(10) Patent No.: US 10,323,099 B2
(45) Date of Patent: Jun. 18, 2019

(54) MULTISPECIFIC DOMAIN EXCHANGED COMMON VARIABLE LIGHT CHAIN ANTIBODIES

(71) Applicant: Hoffmann-La Roche Inc., Little Falls, NJ (US)

(72) Inventors: Peter Bruenker, Hittnau (CH); Christiane Neumann, Niederweningen (CH); Christian Klein, Bonstetten (CH); Ekkehard Moessner, Kreuzlingen (CH); Wolfgang Schaefer, Mannheim (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/092,847

(22) Filed: Apr. 7, 2016

(65) Prior Publication Data

US 2016/0319036 A1 Nov. 3, 2016

Related U.S. Application Data

(63) Continuation of application No. PCT/EP2014/071531, filed on Oct. 8, 2014.

(30) Foreign Application Priority Data

Oct. 11, 2013 (EP) ..................................... 13188283

(51) Int. Cl.
| | | |
|---|---|---|
| *C07K 16/30* | (2006.01) | |
| *C07K 16/40* | (2006.01) | |
| *C07K 16/28* | (2006.01) | |

(52) U.S. Cl.
CPC .......... *C07K 16/40* (2013.01); *C07K 16/2878* (2013.01); *C07K 16/3053* (2013.01); *C07K 2317/24* (2013.01); *C07K 2317/31* (2013.01); *C07K 2317/35* (2013.01); *C07K 2317/41* (2013.01); *C07K 2317/51* (2013.01); *C07K 2317/515* (2013.01); *C07K 2317/522* (2013.01); *C07K 2317/524* (2013.01); *C07K 2317/526* (2013.01); *C07K 2317/56* (2013.01); *C07K 2317/60* (2013.01); *C07K 2317/73* (2013.01)

(58) Field of Classification Search
CPC ......... C07K 16/30; C07K 16/40; C07K 16/28
USPC ....................................................... 424/133.1
See application file for complete search history.

(56) References Cited

U.S. PATENT DOCUMENTS

| | | | |
|---|---|---|---|
| 4,150,149 A | 4/1979 | Wolfsen et al. | |
| 4,361,544 A | 11/1982 | Goldberg | |
| 4,444,744 A | 4/1984 | Goldberg | |
| 4,737,456 A | 4/1988 | Weng et al. | |
| 4,816,567 A | 3/1989 | Cabilly et al. | |
| 5,202,238 A | 4/1993 | Fell, Jr. et al. | |
| 5,204,244 A | 4/1993 | Fell et al. | |
| 5,500,362 A | 3/1996 | Robinson et al. | |
| 5,571,894 A | 11/1996 | Wels et al. | |
| 5,587,458 A | 12/1996 | King et al. | |
| 5,624,821 A | 4/1997 | Winter et al. | |
| 5,648,237 A | 7/1997 | Carter | |
| 5,648,260 A | 7/1997 | Winter et al. | |
| 5,677,425 A | 10/1997 | Bodmer et al. | |
| 5,731,168 A | 3/1998 | Carter et al. | |
| 5,747,654 A | 5/1998 | Pastan et al. | |
| 5,789,199 A | 8/1998 | Joly et al. | |
| 5,798,229 A | 8/1998 | Strittmatter et al. | |
| 5,821,333 A | 10/1998 | Carter et al. | |
| 5,821,337 A | 10/1998 | Carter et al. | |
| 5,840,523 A | 11/1998 | Simmons et al. | |
| 5,869,046 A | 2/1999 | Presta et al. | |
| 5,959,083 A | 9/1999 | Bosslet et al. | |
| 5,959,177 A | 9/1999 | Hein et al. | |
| 6,040,498 A | 3/2000 | Stomp et al. | |
| 6,166,185 A | 12/2000 | Davis et al. | |
| 6,171,586 B1 | 1/2001 | Lam et al. | |
| 6,194,551 B1 | 2/2001 | Idusogie et al. | |
| 6,239,259 B1 | 5/2001 | Davis et al. | |
| 6,248,516 B1 | 6/2001 | Winter et al. | |
| 6,267,958 B1 | 7/2001 | Andya et al. | |
| 6,417,429 B1 | 7/2002 | Hein et al. | |
| 6,420,548 B1 | 7/2002 | Vézina et al. | |
| 6,511,663 B1 | 1/2003 | King et al. | |

(Continued)

FOREIGN PATENT DOCUMENTS

| | | |
|---|---|---|
| CN | 1173878 A | 2/1998 |
| CN | 1176659 A | 3/1998 |

(Continued)

OTHER PUBLICATIONS

Bacac et al. (Clin Cancer Res 2016;22:3286-3297. Published OnlineFirst Feb. 9, 2016).*

(Continued)

*Primary Examiner* — Lynn A Bristol

(74) *Attorney, Agent, or Firm* — Morrison & Foerster LLP

(57) ABSTRACT

Multispecific antibodies based on antibodies that share a common light chain are described herein. The multispecific antibodies include: modified heavy chains having, by domain exchange, a common light chain variable domain VL; and two modified light chains having, by domain exchange, variable heavy chain domains of a first antibody ($VH_1$) and a second antibody ($VH_2$), wherein one light chain is of kappa isotype and one light chain is of lambda isotype. The present invention also relates to methods for the manufacture of such antibodies and their use.

12 Claims, 9 Drawing Sheets

Specification includes a Sequence Listing.

(56) References Cited

U.S. PATENT DOCUMENTS

| | | |
|---|---|---|
| 6,558,672 B1 | 5/2003 | Pastan et al. |
| 6,586,207 B2 | 7/2003 | Tirrell et al. |
| 6,602,684 B1 | 8/2003 | Umaña et al. |
| 6,737,056 B1 | 5/2004 | Presta |
| 6,897,044 B1 | 5/2005 | Braslawsky et al. |
| 6,946,292 B2 | 9/2005 | Kanda et al. |
| 6,982,321 B2 | 1/2006 | Winter |
| 7,125,978 B1 | 10/2006 | Vézina et al. |
| 7,129,330 B1 | 10/2006 | Little et al. |
| 7,183,076 B2 | 2/2007 | Arathoon et al. |
| 7,276,585 B2 | 10/2007 | Lazar et al. |
| 7,317,091 B2 | 1/2008 | Lazar et al. |
| 7,332,581 B2 | 2/2008 | Presta |
| 7,355,008 B2 | 4/2008 | Stavenhagen et al. |
| 7,371,826 B2 | 5/2008 | Presta |
| 7,381,408 B2 | 6/2008 | Mezo et al. |
| 7,504,256 B1 | 3/2009 | Ogawa et al. |
| 7,521,541 B2 | 4/2009 | Eigenbrot et al. |
| 7,642,228 B2 | 1/2010 | Carter et al. |
| 7,651,688 B2 | 1/2010 | Hanai et al. |
| 7,666,622 B2 | 2/2010 | Sharma et al. |
| 7,695,936 B2 | 4/2010 | Carter et al. |
| 7,919,257 B2 | 4/2011 | Hoogenboom et al. |
| 7,942,042 B2 | 5/2011 | Kawakita et al. |
| 7,951,917 B1 | 5/2011 | Arathoon et al. |
| 8,188,231 B2 | 5/2012 | Lazar et al. |
| 8,216,805 B2 | 7/2012 | Carter et al. |
| 8,227,577 B2 | 7/2012 | Klein et al. |
| 8,242,247 B2 | 8/2012 | Klein et al. |
| 8,268,314 B2 | 9/2012 | Baehner et al. |
| 8,304,713 B2 | 11/2012 | Pradel |
| 8,309,300 B2 | 11/2012 | Jununtula et al. |
| 8,313,913 B2 | 11/2012 | Nakamura et al. |
| 8,642,745 B2 | 2/2014 | Arathoon et al. |
| 8,765,412 B2 | 7/2014 | Matsumoto |
| 8,796,424 B2 | 8/2014 | Croasdale et al. |
| 8,945,552 B2 | 2/2015 | Baehner et al. |
| 9,150,639 B2 | 10/2015 | Yamasaki et al. |
| 9,241,994 B2 | 1/2016 | Igawa |
| 9,308,259 B2 | 4/2016 | Epshtein et al. |
| 9,605,084 B2 * | 3/2017 | Moore ................ C07K 16/468 |
| 9,890,204 B2 | 2/2018 | Brinkman et al. |
| 9,982,036 B2 | 5/2018 | Bossenmaier et al. |
| 2002/0062010 A1 | 5/2002 | Arathoon et al. |
| 2002/0155537 A1 | 10/2002 | Carter et al. |
| 2002/0164328 A1 | 11/2002 | Shinkawa et al. |
| 2003/0099974 A1 | 5/2003 | Lillie et al. |
| 2003/0115614 A1 | 6/2003 | Kanda et al. |
| 2003/0124129 A1 | 7/2003 | Oliner |
| 2003/0157108 A1 | 8/2003 | Presta |
| 2004/0018557 A1 | 1/2004 | Qu et al. |
| 2004/0033561 A1 | 2/2004 | O'Keefe et al. |
| 2004/0038339 A1 | 2/2004 | Kufer et al. |
| 2004/0073013 A1 | 4/2004 | Fukushima et al. |
| 2004/0093621 A1 | 5/2004 | Shitara et al. |
| 2004/0109865 A1 | 6/2004 | Niwa et al. |
| 2004/0110282 A1 | 6/2004 | Kanda et al. |
| 2004/0110704 A1 | 6/2004 | Yamane et al. |
| 2004/0132140 A1 | 7/2004 | Satoh et al. |
| 2004/0214988 A1 | 10/2004 | Tirrell et al. |
| 2004/0220388 A1 | 11/2004 | Metens et al. |
| 2004/0259075 A1 | 12/2004 | Dimitrove et al. |
| 2004/0259150 A1 | 12/2004 | Nakamura et al. |
| 2005/0014934 A1 | 1/2005 | Hinton et al. |
| 2005/0031613 A1 | 2/2005 | Nakamura et al. |
| 2005/0054048 A1 | 3/2005 | Grasso et al. |
| 2005/0064509 A1 | 4/2005 | Bradbury et al. |
| 2005/0079170 A1 | 4/2005 | Le Gall et al. |
| 2005/0123476 A1 | 6/2005 | Bugge et al. |
| 2005/0123546 A1 | 6/2005 | Umana et al. |
| 2005/0152894 A1 | 7/2005 | Krummen et al. |
| 2005/0163782 A1 | 7/2005 | Glaser et al. |
| 2005/0249722 A1 | 11/2005 | Beliard et al. |
| 2005/0260186 A1 | 11/2005 | Bookbinder et al. |
| 2006/0063921 A1 | 3/2006 | Moulder et al. |
| 2006/0104968 A1 | 5/2006 | Bookbinder et al. |
| 2006/0122370 A1 | 6/2006 | Oliner et al. |
| 2006/0134709 A1 | 6/2006 | Stavenhagen et al. |
| 2006/0160184 A1 | 7/2006 | Hoogenboom et al. |
| 2006/0280747 A1 | 12/2006 | Fuh et al. |
| 2007/0071675 A1 | 3/2007 | Wu et al. |
| 2007/0071742 A1 | 3/2007 | Fang et al. |
| 2007/0092940 A1 | 4/2007 | Eigenbrot et al. |
| 2007/0134759 A1 | 6/2007 | Nishiya et al. |
| 2007/0141065 A1 | 6/2007 | Fuh et al. |
| 2007/0166305 A1 | 7/2007 | Hanai et al. |
| 2007/0269369 A1 | 11/2007 | Gegg et al. |
| 2007/0274985 A1 | 11/2007 | Dubel et al. |
| 2007/0274998 A1 | 11/2007 | Uktu |
| 2007/0287170 A1 | 12/2007 | Davis et al. |
| 2008/0063641 A1 | 3/2008 | Huang et al. |
| 2008/0187954 A1 | 8/2008 | Kallmeier et al. |
| 2008/0234183 A1 | 9/2008 | Hallbrink et al. |
| 2008/0241884 A1 | 10/2008 | Shitara et al. |
| 2009/0023811 A1 | 1/2009 | Biadatti et al. |
| 2009/0060910 A1 | 3/2009 | Johnson |
| 2009/0155275 A1 | 6/2009 | Wu et al. |
| 2009/0162359 A1 | 6/2009 | Klein et al. |
| 2009/0162360 A1 | 6/2009 | Klein et al. |
| 2009/0175851 A1 | 7/2009 | Klein et al. |
| 2009/0203078 A1 | 8/2009 | Ogawa et al. |
| 2009/0194692 A1 | 9/2009 | Kobaru |
| 2009/0232811 A1 | 9/2009 | Klein et al. |
| 2010/0015133 A1 | 1/2010 | Igawa et al. |
| 2010/0081796 A1 | 4/2010 | Brinkman et al. |
| 2010/0111967 A1 | 5/2010 | Baehner et al. |
| 2010/0254989 A1 | 10/2010 | Bossenmaier et al. |
| 2010/0256338 A1 | 10/2010 | Brinkmann et al. |
| 2010/0256340 A1 | 10/2010 | Brinkmann et al. |
| 2010/0286374 A1 | 11/2010 | Kannan et al. |
| 2010/0316645 A1 | 12/2010 | Imhof-Jung et al. |
| 2010/0322934 A1 | 12/2010 | Imhof-Jung et al. |
| 2010/0322935 A1 | 12/2010 | Croasdale et al. |
| 2011/0054151 A1 | 3/2011 | Lazar et al. |
| 2012/0029481 A1 | 2/2012 | Pech et al. |
| 2012/0149879 A1 | 6/2012 | Brinkmann et al. |
| 2012/0164726 A1 | 6/2012 | Klein et al. |
| 2012/0177637 A1 | 7/2012 | Hoogenboom et al. |
| 2012/0184718 A1 | 7/2012 | Bruenker et al. |
| 2012/0225071 A1 | 9/2012 | Klein et al. |
| 2012/0237506 A1 | 9/2012 | Bossenmaier et al. |
| 2012/0237507 A1 | 9/2012 | Bossenmaier et al. |
| 2013/0022601 A1 | 1/2013 | Brinkmann et al. |
| 2013/0045492 A1 | 2/2013 | Babb et al. |
| 2013/0058936 A1 * | 3/2013 | Bruenker ............ C07K 16/468 424/136.1 |
| 2013/0058937 A1 | 3/2013 | Auer et al. |
| 2013/0060011 A1 * | 3/2013 | Bruenker ............ C07K 16/468 530/387.3 |
| 2013/0078249 A1 | 3/2013 | Ast et al. |
| 2013/0156772 A1 | 6/2013 | Bossenmaier et al. |
| 2013/0266568 A1 | 10/2013 | Brinkmann et al. |
| 2013/0267686 A1 | 10/2013 | Brinkmann et al. |
| 2013/0273054 A1 | 10/2013 | Bossenmaier et al. |
| 2014/0112914 A1 | 4/2014 | Nezu et al. |
| 2014/0154254 A1 | 6/2014 | Kannan et al. |
| 2014/0199294 A1 | 7/2014 | Mimoto et al. |
| 2014/0249296 A1 | 9/2014 | Ploegh |
| 2014/0294810 A1 | 10/2014 | Lowman et al. |
| 2014/0322756 A1 | 10/2014 | Arathoon et al. |
| 2014/0370019 A1 | 12/2014 | Bruenker et al. |
| 2014/0370020 A1 | 12/2014 | Kuramochi et al. |
| 2015/0132307 A1 | 5/2015 | Auer et al. |
| 2015/0166670 A1 | 6/2015 | Castoldi et al. |
| 2015/0232541 A1 | 8/2015 | Fenn |
| 2015/0232560 A1 | 8/2015 | Heindl et al. |
| 2015/0274845 A1 * | 10/2015 | Bruenker ............ C07K 16/468 424/136.1 |
| 2015/0291704 A1 | 10/2015 | Beck |
| 2015/0315296 A1 | 11/2015 | Schaefer et al. |
| 2015/0344570 A1 | 12/2015 | Igawa et al. |
| 2016/0168259 A1 | 1/2016 | Igawa |
| 2016/0039937 A1 | 2/2016 | Yamasaki et al. |
| 2016/0075785 A1 | 3/2016 | Ast et al. |

(56) References Cited

U.S. PATENT DOCUMENTS

| | | | |
|---|---|---|---|
| 2016/0238600 A1 | 4/2016 | Hoogenboom et al. | |
| 2016/0130347 A1* | 5/2016 | Bruenker | C07K 16/2809 424/136.1 |
| 2016/0208019 A1* | 7/2016 | Bacac | C07K 16/468 |
| 2016/0222132 A1* | 8/2016 | Keyt | C07K 16/00 |
| 2017/0029529 A1* | 2/2017 | Croasdale | C07K 16/32 |
| 2017/0037121 A1* | 2/2017 | Schlothauer | C07K 16/22 |
| 2017/0037153 A1* | 2/2017 | Skolaut | C07K 16/22 |
| 2017/0044246 A1* | 2/2017 | Schlothauer | C07K 16/22 |
| 2017/0096485 A1 | 4/2017 | Bacac et al. | |
| 2017/0096495 A1 | 4/2017 | Bacac et al. | |
| 2017/0114135 A1 | 4/2017 | Codarri-Deak et al. | |
| 2017/0114141 A1* | 4/2017 | Amann | C12Y 304/14005 |
| 2017/0114146 A1 | 4/2017 | Klein et al. | |
| 2017/0129962 A1 | 5/2017 | Regula et al. | |
| 2017/0145116 A1 | 5/2017 | Regula et al. | |
| 2017/0174786 A1 | 6/2017 | Bacac et al. | |
| 2017/0190783 A1 | 7/2017 | Bacac et al. | |
| 2017/0247467 A1* | 8/2017 | Amann | C07K 16/40 |
| 2017/0253670 A1* | 9/2017 | Klein | C07K 16/464 |
| 2017/0306018 A1 | 10/2017 | Vu et al. | |
| 2017/0306036 A1 | 10/2017 | Vu et al. | |
| 2017/0349669 A1 | 12/2017 | Sabine et al. | |
| 2018/0037633 A1 | 2/2018 | Bossenmaier et al. | |
| 2018/0312573 A1 | 11/2018 | Bossenmaier et al. | |

FOREIGN PATENT DOCUMENTS

| | | |
|---|---|---|
| CN | 1232039 A | 10/1999 |
| CN | 1603345 A | 4/2005 |
| CN | 101065151 A | 10/2007 |
| CN | 101205255 A | 6/2008 |
| CN | 101218251 A | 7/2008 |
| CN | 101355966 A | 1/2009 |
| EP | 0 307 434 B1 | 3/1989 |
| EP | 0 307 434 B2 | 3/1989 |
| EP | 0 637 593 A1 | 2/1995 |
| EP | 1 331 266 A1 | 7/2003 |
| EP | 1 870 458 A1 | 12/2007 |
| EP | 1 870 459 A1 | 12/2007 |
| EP | 1 925 319 A1 | 5/2008 |
| EP | 2 050 764 A1 | 4/2009 |
| EP | 2 443 154 B1 | 4/2012 |
| EP | 2 554 669 A1 | 2/2013 |
| EP | 2 647 707 A1 | 10/2013 |
| EP | 2 728 002 A1 | 5/2014 |
| EP | 2 787 078 A1 | 10/2014 |
| EP | 2 940 135 A1 | 11/2015 |
| JP | 2008-531049 A | 8/2008 |
| JP | 2011-506510 A | 3/2011 |
| JP | 2012-525149 A | 10/2012 |
| JP | 2013-539461 A | 10/2013 |
| JP | 2015-502373 A | 1/2015 |
| RU | 2005/124281 A | 1/2006 |
| RU | 2295537 C2 | 3/2007 |
| WO | WO-1993/01161 A1 | 1/1993 |
| WO | WO-93/06217 A1 | 4/1993 |
| WO | WO-1993/10819 A1 | 6/1993 |
| WO | WO-1993/16185 A2 | 8/1993 |
| WO | WO-1993/16185 A3 | 8/1993 |
| WO | WO-94/09131 A1 | 4/1994 |
| WO | WO-94/10202 A1 | 5/1994 |
| WO | WO-94/29350 A2 | 12/1994 |
| WO | WO-94/29350 A3 | 12/1994 |
| WO | WO-94/29351 A2 | 12/1994 |
| WO | WO-94/29351 A3 | 12/1994 |
| WO | WO-1995/09917 A1 | 4/1995 |
| WO | WO-96/027011 A1 | 9/1996 |
| WO | WO-1996/27612 A1 | 9/1996 |
| WO | WO-1997/01580 A1 | 1/1997 |
| WO | WO-1997/014719 A1 | 4/1997 |
| WO | WO-97/30087 A1 | 8/1997 |
| WO | WO-1997/028267 A1 | 8/1997 |
| WO | WO-1997/028267 C1 | 8/1997 |
| WO | WO-98/10431 A2 | 3/1998 |
| WO | WO-98/10431 C1 | 3/1998 |
| WO | WO-1998/45331 A2 | 10/1998 |
| WO | WO-1998/45331 A3 | 10/1998 |
| WO | WO-1998/45332 A2 | 10/1998 |
| WO | WO-1998/45332 A3 | 10/1998 |
| WO | WO-1998/48032 A2 | 10/1998 |
| WO | WO-1998/48032 A3 | 10/1998 |
| WO | WO-98/50431 A2 | 11/1998 |
| WO | WO-98/50431 A3 | 11/1998 |
| WO | WO-98/58964 A1 | 12/1998 |
| WO | WO-99/22764 A1 | 5/1999 |
| WO | WO-1999/37791 A1 | 7/1999 |
| WO | WO-99/51642 A1 | 10/1999 |
| WO | WO-1999/54342 A1 | 10/1999 |
| WO | WO-1999/66951 A2 | 12/1999 |
| WO | WO-1999/66951 A3 | 12/1999 |
| WO | WO-1999/66951 C1 | 12/1999 |
| WO | WO-2000/05265 A2 | 2/2000 |
| WO | WO-2000/05265 A3 | 2/2000 |
| WO | WO-2009/021754 A2 | 2/2000 |
| WO | WO-2000/35956 A1 | 6/2000 |
| WO | WO-00/61739 A1 | 10/2000 |
| WO | WO-01/29246 A1 | 4/2001 |
| WO | WO-2001/77342 A1 | 10/2001 |
| WO | WO-2001/085795 A1 | 11/2001 |
| WO | WO-2001/90192 A2 | 11/2001 |
| WO | WO-2001/90192 A3 | 11/2001 |
| WO | WO-2002/02781 A1 | 1/2002 |
| WO | WO-02/31140 A1 | 4/2002 |
| WO | WO-2002/33073 A1 | 4/2002 |
| WO | WO-2002/096948 A2 | 12/2002 |
| WO | WO-2002/096948 A3 | 12/2002 |
| WO | WO-2002/096948 A9 | 12/2002 |
| WO | WO-03/011878 A2 | 2/2003 |
| WO | WO-03/011878 A3 | 2/2003 |
| WO | WO-2003/030833 A2 | 4/2003 |
| WO | WO-2003/030833 A3 | 4/2003 |
| WO | WO-2003/035835 A2 | 5/2003 |
| WO | WO-2003/035835 A3 | 5/2003 |
| WO | WO-03/055993 A1 | 7/2003 |
| WO | WO-2003/057134 A2 | 7/2003 |
| WO | WO-2003/057134 A3 | 7/2003 |
| WO | WO-2003/073238 A2 | 9/2003 |
| WO | WO-2003/073238 A3 | 9/2003 |
| WO | WO-03/084570 A1 | 10/2003 |
| WO | WO-03/085107 A1 | 10/2003 |
| WO | WO-03/085119 A1 | 10/2003 |
| WO | WO-2003/097105 A1 | 11/2003 |
| WO | WO-2003/106501 A1 | 12/2003 |
| WO | WO-2004/003019 A2 | 1/2004 |
| WO | WO-2004/003019 A3 | 1/2004 |
| WO | WO-2004/032961 A1 | 4/2004 |
| WO | WO-2004/056312 A2 | 7/2004 |
| WO | WO-2004/056312 A3 | 7/2004 |
| WO | WO-2004/058298 A1 | 7/2004 |
| WO | WO-2004/065540 A2 | 8/2004 |
| WO | WO-2004/065540 A3 | 8/2004 |
| WO | WO-2004/072117 A2 | 8/2004 |
| WO | WO-2004/072117 A3 | 8/2004 |
| WO | WO-2004/106375 A1 | 12/2004 |
| WO | WO-2005/000900 A1 | 1/2005 |
| WO | WO-2005/001025 A2 | 1/2005 |
| WO | WO-2005/001025 A3 | 1/2005 |
| WO | WO-2005/004809 A2 | 1/2005 |
| WO | WO-2005/004809 A3 | 1/2005 |
| WO | WO-2005/005635 A2 | 1/2005 |
| WO | WO-2005/005635 A3 | 1/2005 |
| WO | WO-2005/011735 A1 | 2/2005 |
| WO | WO-2005/018572 A2 | 3/2005 |
| WO | WO-2005/018572 A3 | 3/2005 |
| WO | WO-2005/027966 A2 | 3/2005 |
| WO | WO-2005/027966 A3 | 3/2005 |
| WO | WO-2005/033778 A2 | 4/2005 |
| WO | WO-2005/033778 A3 | 4/2005 |
| WO | WO-2005/035586 A1 | 4/2005 |
| WO | WO-2005/035727 A2 | 4/2005 |
| WO | WO-2005/035727 A3 | 4/2005 |
| WO | WO-2005/035778 A1 | 4/2005 |

(56) References Cited

FOREIGN PATENT DOCUMENTS

| | | |
|---|---|---|
| WO | WO-2005/044853 A2 | 5/2005 |
| WO | WO-2005/044853 A3 | 5/2005 |
| WO | WO-2005/044859 A2 | 5/2005 |
| WO | WO-2005/044859 A3 | 5/2005 |
| WO | WO-2005/051422 A1 | 6/2005 |
| WO | WO-2005/051976 A2 | 6/2005 |
| WO | WO-2005/053742 A1 | 6/2005 |
| WO | WO-2005/063816 A2 | 7/2005 |
| WO | WO-2005/063816 A3 | 7/2005 |
| WO | WO-2005/074524 A2 | 8/2005 |
| WO | WO-2005/074524 A3 | 8/2005 |
| WO | WO-2005/092925 A2 | 10/2005 |
| WO | WO-2005/092925 A3 | 10/2005 |
| WO | WO-2005/100402 A1 | 10/2005 |
| WO | WO-2006/020258 A2 | 2/2006 |
| WO | WO-2006/020258 A3 | 2/2006 |
| WO | WO-2006/029879 A2 | 3/2006 |
| WO | WO-2006/029879 A3 | 3/2006 |
| WO | WO-2006/031370 A2 | 3/2006 |
| WO | WO-2006/031370 A3 | 3/2006 |
| WO | WO-2006/034488 A2 | 3/2006 |
| WO | WO-2006/034488 A3 | 3/2006 |
| WO | WO-2006/044908 A2 | 4/2006 |
| WO | WO-2006/044908 A3 | 4/2006 |
| WO | WO-2006/045049 A1 | 4/2006 |
| WO | WO-2006/068953 A2 | 6/2006 |
| WO | WO-2006/068953 A3 | 6/2006 |
| WO | WO-2006/082515 A2 | 8/2006 |
| WO | WO-2006/082515 A3 | 8/2006 |
| WO | WO-2006/091209 A2 | 8/2006 |
| WO | WO-2006/091209 A3 | 8/2006 |
| WO | WO-2006/093794 A1 | 8/2006 |
| WO | WO-2006/103100 A2 | 10/2006 |
| WO | WO-2006/103100 A3 | 10/2006 |
| WO | WO-2006/106905 A1 | 10/2006 |
| WO | WO-2006/113665 A2 | 10/2006 |
| WO | WO-2006/113665 A3 | 10/2006 |
| WO | WO-2006/114700 A2 | 11/2006 |
| WO | WO-2006/114700 A3 | 11/2006 |
| WO | WO-2006/116260 A2 | 11/2006 |
| WO | WO-2006/116260 A3 | 11/2006 |
| WO | WO-2006/132352 A1 | 12/2006 |
| WO | WO-2007/024715 A2 | 3/2007 |
| WO | WO-2007/024715 A3 | 3/2007 |
| WO | WO-2007/031875 A2 | 3/2007 |
| WO | WO-2007/031875 A3 | 3/2007 |
| WO | WO-2007/044887 A2 | 4/2007 |
| WO | WO-2007/044887 A3 | 4/2007 |
| WO | WO-2007/048037 A2 | 4/2007 |
| WO | WO-2007/048037 A3 | 4/2007 |
| WO | WO-2007/068895 A1 | 6/2007 |
| WO | WO-2007/084181 A2 | 7/2007 |
| WO | WO-2007/084181 A3 | 7/2007 |
| WO | WO-2007/085837 A1 | 8/2007 |
| WO | WO-2007/087445 A3 | 8/2007 |
| WO | WO-2007/089445 A3 | 8/2007 |
| WO | WO-2007/095338 A2 | 8/2007 |
| WO | WO-2007/095338 A3 | 8/2007 |
| WO | WO-2007/108013 A2 | 9/2007 |
| WO | WO-2007/108013 A3 | 9/2007 |
| WO | WO-2007/109254 A2 | 9/2007 |
| WO | WO-2007/110205 A2 | 10/2007 |
| WO | WO-2007/110205 A3 | 10/2007 |
| WO | WO-2007/146959 A2 | 12/2007 |
| WO | WO-2007/146959 A3 | 12/2007 |
| WO | WO-2007/147901 A1 | 12/2007 |
| WO | WO-2007/149010 A1 | 12/2007 |
| WO | WO-2008/005828 A2 | 1/2008 |
| WO | WO-2008/005828 A3 | 1/2008 |
| WO | WO-2008/017963 A3 | 2/2008 |
| WO | WO-2008/022349 A2 | 2/2008 |
| WO | WO-2008/027236 A2 | 2/2008 |
| WO | WO-2008/027236 A2 | 3/2008 |
| WO | WO-2008/027236 A3 | 3/2008 |
| WO | WO-2008/077077 A2 | 6/2008 |
| WO | WO-2008/077077 A3 | 6/2008 |
| WO | WO-2008/077546 A1 | 7/2008 |
| WO | WO-2008/100624 A2 | 8/2008 |
| WO | WO-2008/100624 A3 | 8/2008 |
| WO | WO-2008/132568 A2 | 11/2008 |
| WO | WO-2008/132568 A3 | 11/2008 |
| WO | WO-2009/018386 A1 | 2/2009 |
| WO | WO-2009/021745 A1 | 2/2009 |
| WO | WO-2009/021754 A3 | 2/2009 |
| WO | WO-2009/023843 A1 | 2/2009 |
| WO | WO-2009/032782 A2 | 3/2009 |
| WO | WO-2009/032782 A3 | 3/2009 |
| WO | WO-2005/051976 A3 | 6/2009 |
| WO | WO-2009/080251 A1 | 7/2009 |
| WO | WO 2009/080252 A1 | 7/2009 |
| WO | WO-2009/080253 A1 | 7/2009 |
| WO | WO-2009/080254 A1 | 7/2009 |
| WO | WO-2009/089004 A1 | 7/2009 |
| WO | WO-2009/126944 A1 | 10/2009 |
| WO | WO-2010/034441 A1 | 4/2010 |
| WO | WO-2010/040508 A1 | 4/2010 |
| WO | WO-2010/040508 A8 | 4/2010 |
| WO | WO-2010/040508 A9 | 4/2010 |
| WO | WO-2010/045193 A1 | 4/2010 |
| WO | WO-2010/065882 A1 | 6/2010 |
| WO | WO-2010/084197 A1 | 7/2010 |
| WO | WO-2010/087994 A2 | 8/2010 |
| WO | WO-2010/087994 A3 | 8/2010 |
| WO | WO-2010/108127 A1 | 9/2010 |
| WO | WO-2010/112193 A1 | 10/2010 |
| WO | WO-2010/112194 A1 | 10/2010 |
| WO | WO-2010/115552 A1 | 10/2010 |
| WO | WO-2010/115589 A1 | 10/2010 |
| WO | WO-2010/115589 A8 | 10/2010 |
| WO | WO-2010/115598 A1 | 10/2010 |
| WO | WO-2010/129304 A2 | 11/2010 |
| WO | WO-2010/129304 A3 | 11/2010 |
| WO | WO-2010/136172 A1 | 12/2010 |
| WO | WO-2010/145792 A1 | 12/2010 |
| WO | WO-2010/145793 A1 | 12/2010 |
| WO | WO-2011/003557 A1 | 1/2011 |
| WO | WO-2011/028952 A1 | 3/2011 |
| WO | WO-2011/034605 A2 | 3/2011 |
| WO | WO-2011/034605 A3 | 3/2011 |
| WO | WO-2011/090754 A1 | 7/2011 |
| WO | WO-2011/090762 A1 | 7/2011 |
| WO | WO-2011/097603 A1 | 8/2011 |
| WO | WO-2011/118739 A1 | 9/2011 |
| WO | WO-2011/143545 A1 | 11/2011 |
| WO | WO-2012/023053 A2 | 2/2012 |
| WO | WO-2012/023053 A3 | 2/2012 |
| WO | WO-2012/148873 A2 | 2/2012 |
| WO | WO-2012/025525 A1 | 3/2012 |
| WO | WO-2012/025530 A1 | 3/2012 |
| WO | WO-2012/058768 A1 | 5/2012 |
| WO | WO-2012/073985 A1 | 6/2012 |
| WO | WO-2012/075037 A1 | 6/2012 |
| WO | WO-2012/116927 A1 | 9/2012 |
| WO | WO-2012/131555 A2 | 10/2012 |
| WO | WO-2012/131555 A3 | 10/2012 |
| WO | WO-2012/143379 A1 | 10/2012 |
| WO | WO-2012/148873 A3 | 11/2012 |
| WO | WO-2012/148873 A4 | 11/2012 |
| WO | WO-2013/002362 A1 | 1/2013 |
| WO | WO-2013/003555 A1 | 1/2013 |
| WO | WO-2013/012733 A1 | 1/2013 |
| WO | WO-2013/026832 A1 | 2/2013 |
| WO | WO-2013/026833 A1 | 2/2013 |
| WO | WO-2013/026835 A1 | 2/2013 |
| WO | WO-2013/065708 A1 | 5/2013 |
| WO | WO-2013/092001 A1 | 6/2013 |
| WO | WO-2013/092716 A1 | 6/2013 |
| WO | WO-2013/096291 A2 | 6/2013 |
| WO | WO-2013/096291 A3 | 6/2013 |
| WO | WO-2013/150043 A1 | 10/2013 |
| WO | WO-2013/157953 A1 | 10/2013 |
| WO | WO-2013/157954 A1 | 10/2013 |
| WO | WO-2013/174873 A1 | 11/2013 |
| WO | WO-2014/012085 A2 | 1/2014 |

(56) References Cited

FOREIGN PATENT DOCUMENTS

| WO | WO-2014/012085 A3 | 1/2014 |
|---|---|---|
| WO | WO-2014/049003 A1 | 4/2014 |
| WO | WO-2014/081955 A1 | 5/2014 |
| WO | WO-2014/082179 A1 | 6/2014 |
| WO | WO-2014/104165 A1 | 7/2014 |
| WO | WO-2014/144357 A1 | 9/2014 |
| WO | WO-2015/101588 A1 | 7/2015 |
| WO | WO-2016/016299 A1 | 2/2016 |
| WO | WO-2016/055432 A2 | 4/2016 |
| WO | WO-2016/055432 A3 | 4/2016 |
| WO | WO-2016/087416 A1 | 6/2016 |
| WO | WO-2017/055385 A1 | 4/2017 |
| WO | WO-2017/055392 A1 | 4/2017 |
| WO | WO-2017/055393 A1 | 4/2017 |

OTHER PUBLICATIONS

Croasdale et al. (Archives of Biochemistry and Biophysics 526 (2012) 206-218).*
Klein et al. (MABS 2016, vol. 8, No. 6, 1010-1020).*
Schaefer et al. (mAbs 8:1, 49-55; Jan. 2016).*
Schanzer et al (MABS 2016, vol. 8, No. 4, 811-827).*
Brunker et al. (Mol Cancer Ther; 15(5):946-957 (May 2016); Published OnlineFirst Apr. 1, 2016).*
Atwell et al. "Stable Heterodimers from Remodeling the Domain Interface of a Homodimer using a Phage Display Library," *J. Mol. Biol.* 270:26-35, (1997).
Barnes et al. "Advances in Animal Cell Recombinant Protein Production: GS-NS0 Expression System," *Cytotechnology* 32:109-123, (2000).
Barnes et al. "Characterization of the Stability of Recombinant Protein Production in the GS-NSO Expression System," *Biotech. Bioeng.* 73(4):261-270, (May 20, 2001).
Boerner et al. "Production of Antigen-Specific Human Monoclonal Antibodies From in Vitro-Primed-Human Splenocytes," *J. Immunol.* 147(1):86-95, (Jul. 1, 1991).
Brüggemann et al. "Designer Mice: The Production of Human Antibody Repertoires in Transgenic Animals," *Year Immunol.* 7:33-40, (1993).
Brüggemann et al. "Comparison of the Effector Functions of Human Immunoglobulins Using a Matched Set of Chimeric Antibodies," *J. Exp. Med.* 166:1351-1361, (Nov. 1, 1987).
Carter et al. "Humanization of an Anti-p185$^{HER2}$ Antibody for Human Cancer Therapy," *Proc. Natl. Acad. Sci. USA* 89:4285-4289, (May 1992).
Charlton. "Expression and Isolation of Recombinant Antibody Fragments in *E. coli*" Chapter 14 in *Methods in Molecular Biology*, B.K.C. Lo, ed., Humana Press, Totowa, NJ, 248:245-254, (2003).
Chowdhury. "Engineering Hot Spots for Affinity Enhancement of Antibodies," Chapter 11 in *Methods in Molecular Biology*, Welschof, M. et al. ed., Humana Press, Totowa, NJ, 207:179-196, (2008).
Clynes et al. "Fc Receptors are Required in Passive and Active Immunity to Melanoma," *Proc. Natl. Acad. Sci. USA* 95:652-656, (1998).
Cohen et al. "Nonchromosomal Antibiotic Resistance in Bacteria: Genetic Transformation of *Escherichia coli* by R-Factor DNA," *Proc. Natl. Acad. Sci. USA* 69(8):2110-2114, (Aug. 1972).
Cole et al. "The EBV-Hybridoma technique and its application to human lung cancer" in *Monoclonal Antibodies and Cancer Therapy* Alan R. Liss, Inc., New York, pp. 77-96 (1985).
Coloma et. al. "Design and Production of Novel Tetravalent Bispecific Antibodies," *Nature Biotech.* 15:159-163, (Feb. 1997).
Cragg et al. "Complement-Mediated Lysis by Anti-CD20 mAb Correlates with Segregation Into Lipid Rafts," *Blood* 101(3):1045-1052, (Feb. 1, 2003.).
Cragg, et al. "Antibody Specificity Controls in Vivo Effector Mechanisms of Anti-CD20 Reagents," *Blood* 103(7):2738-2743, (Apr. 1, 2004).

Cunningham et al. "High-Resolution Epitope Mapping of hGH-Receptor Interactions by Alanine-Scanning Mutagenesis," *Science* 244:1081-1085, (Jun. 2, 1989).
De Haard et al. "A large Non-Immunized Human Fab Fragment Phage Library That Permits Rapid Isolation and Kinetic Analysis of High Affinity Antibodies," *The Journal of Biological Chemistry* 274(26):18218-18230, (Jun. 25, 1999).
Duncan et al. "The Binding Site for C1q on IgG," *Nature* 332:738-40, (Apr. 21, 1988).
Durocher et al. "High-Level and High-Throughput Recombinant Protein Production by Transient Transfection of Suspension-Growing Human 293-EBNA1 Cells," *Nucl. Acids. Res.* 30(2 e9):1-9, (2002).
Flatman et al. "Process Analytics for Purification of Monoclonal Antibodies," *J. Chromatogr. B* 848:79-87, (2007; e-published Dec. 11, 2006).
Gazzano-Santoro et al. "A Non-radioactive Complement-dependent Cytotoxicity Assay for Anti-CD20 Monoclonal Antibody," *J. Immunol. Methods* 202:163-171, (1997).
Geisse et al. "Eukaryotic Expression Systems: A Comparison," *Protein Expr. Purif.* 8:271-282, (1996).
Gerngross. "Advances in the Production of Human Therapeutic Proteins in Yeasts and Filamentous Fungi," *Nat. Biotech.* 22(11):1409-1414, (Nov. 2004).
Graham et al. "Characteristics of a Human Cell Line Transformed by DNA from Human Adenovirus Type 5," *J. Gen Virol.* 36:59-72, (1977).
Graham et al. "A New Technique for the Assay of Infectivity of Human Adenovirus 5 DNA," *Virology* 52:456-467, (1973).
Guyer et al. "Immunoglobulin Binding by Mouse Intestinal Epithelial Cell Receptors," *J. Immunol.* 117(2):587-593, (Aug. 1976).
Hellstrom et al. "Antitumor Effects of L6, an IgG2a Antibody That Reacts with Most Human Carcinomas," *Proc. Natl. Acad. Sci. USA* 83:7059-7063, (Sep. 1986).
Hellstrom et al. "Strong Antitumor Activities of IgG3 Antibodies to a Human Melanoma-Associated Ganglioside," *Proc. Natl. Acad. Sci. USA* 82:1499-1502, (Mar. 1985).
Hoogenboom et al. "By-Passing Immunisation Human Antibodies from Synthetic Repertoires of Germline $V_H$ Gene Segments Rearranged in Vitro," *J. Mol. Biol.*, 227:381-388, (1992).
Hoogenboom et al. "Overview of Antibody Phage-Display Technology and Its Applications," Chapter 1 in *Methods in Molecular Biology*, O'Brien et al., ed., Human Press, Totowa, NJ, 178:1-37, (2001).
Idusogie et al. "Mapping of the C1q Binding Site on Rituxan, a Chimeric Antibody with a Human IgG1 Fc," *J. Immunol.* 164:4178-4184, (2000).
Jackman et al. "Development of a Two-part Strategy to Identify a Therapeutic Human Bispecific Antibody That Inhibits IgE Receptor Signaling," *The Journal of Biological Chemistry* 285(27):20850-20859, (Jul. 2, 2010).
Jakobovits et al., "Analysis of Homozygous Mutant Chimeric Mice: Deletion of the Immunoglobulin Heavy-Chain Joining Region Blocks B-Cell Development and Antibody Production" *Proc. Natl. Acad. Sci. USA* 90(6):2551-2555 (Mar. 15, 1993).
Jakobovits et al., "Germ-line Transmission and Expression of a Human-Derived Yeast Artificial Chromosome," *Nature* 362(6417):255-258 (Mar. 18, 1993).
Johnson et al. "Kabat Database and Its Applications: 30 Years After the First Variability Plot," *Nucleic Acids Res.* 28(1):214-218, (2000).
Kabat et al. "Evolutionary and Structural influences on Light Chain Constant ($C_L$) Region of Human and Mouse Immunoglobulins," *Proc. Natl. Acad. Sci. USA* 72(7):2785-2788, (Jul. 1975).
Kabat et al. "Sequences of Proteins of Immunological Interest," *National Institutes of Health*, vol. 1, Fifth Edition, pp. 647-723, (1991).
Kam et al. "Carbon Nanotubes as Multifunctional Biological Transporters and Near-Infrared Agents for Selective Cancer Cell Destruction," *Proc. Natl. Acad. Sci. USA* 102(33):11600-11605, (Aug. 16, 2005).
Kanda et al. "Comparison of Cell Lines for Stable Production of Fucose-Negative Antibodies With Enhanced ADCC," *Biotechnol. Bioeng.* 94(4):680-688, (Jul. 5, 2006; e-published Apr. 11, 2006).

(56) References Cited

OTHER PUBLICATIONS

Kaufman. "Overview of Vector Design for Mammalian Gene Expression," *Mol. Biotechnol.* 16:151-160, (2000).
Kim et al. "Localization of the Site of the Murine IgG1 Molecule that is Involved in Binding to the Marine Intestinal Fc Receptor," *Eur. J. Immunol.* 24:2429-2434, (1994).
Klein et al. "Progress in Overcoming the Chain Association Issue in Bispecific Heterodimeric IgG Antibodies," *MABS* 4(6):653-663, (Nov. 1, 2012).
Li et al. "Optimization of Humanized IgGs in Glycoengineered *Pichia pastoris*," *Nat. Biotech.* 24(2):210-215, (Feb. 2006; e-published Jan. 22, 2006).
Makrides. "Components of Vectors for Gene Transfer arid Expression in Mammalian Cells," *Protein Expr. Purif.* 17:183-202, (1999).
Marks et al. "By-passing Immunization Human Antibodies from V-gene Libraries Displayed on Phage," *J. Mol. Biol.* 222:581-597, (1991).
Mather. "Establishment and Characterization of Two Distinct Mouse Testicular Epithelial Cell Lines," *Biol. Reprod.* 23:243-251, (1980).
Mather et al. "Culture of Testicular Cells in Hormone-Supplemented Serum-Free Medium," *Annals N.Y. Acad. Sci.* 383:44-68, (1982).
Merchant et al. "An Efficient Route to Human Bispecific IgG," *Nature Biotechnology* 16(7):677-681, (Jul. 1, 1998).
Milstein et al. "Hybrid Hybridomas and Their use in Immunohistochemistry," *Nature* 305: 537-540, (Oct. 6, 1983).
Morrison et al. "Variable Region Domain Exhange Influences the Functional Properties of IgG," *Journal of Immunology* 160:2802-2808, (1998).
Morrison. "Two Heads are Better Than One," *Nature Biotech.* 25(11):1233-1234, (Nov. 2007).
Morrison et al. "Chimeric Human Antibody Molecules: Mouse Antigen-Binding Domains With Human Constant Region Domains," *Proc. Natl. Acad. Sci. USA* 81:6851-6855, (Nov. 1984).
Neuberger et al. "A Hapten-Specific Chimaeric IgE Antibody With Human Physiological Effector Function," *Nature* 314:268-270, (Mar. 1985).
Norderhaug et al. "Versatile Vectors for Transient and Stable Expression of Recombinant Antibody Molecules in Mammalian Cells," *J. Immunol. Methods* 204:77-87, (1997).
Okazaki et al. "Fucose Depletion from Human IgG1 Oligosaccharide Enhances Binding Enthalpy and Association Rate Between IgG1 and FcγRIIIa," *J. Mol. Biol.* 336:1239-1249, (2004).
Orlandi et al. "Cloning Immunoglobulin Variable Domains for Expression by the Polymerase Chain Reaction," *Proc. Natl. Acad. Sci. USA* 86:3833-3837, (May 1989).
Petkova et al. "Enhanced Half-Life of Genetically Engineered Human IgG1 Antibodies in a Humanized FcRn Mouse Model: Potential Application in Humorally Mediated Autoimmune Disease," *Int'l. Immunol.* 18(12):1759-1769, (2006).
Ravetch et al. "Fc Receptors," *Annu. Rev. Immunol.* 9:457-92, (1991).
Ridgway et al. "'Knobs-Into-Holes' Engineering of Antibody $C_H3$ Domains for Heavy Chain Heterodimerization," *Protein Eng.* 9(7):617-621, (1996).
Riechmann et al. "Reshaping Human Antibodies for Therapy," *Nature* 332:323-329, (Mar. 24, 1988).
Ripka et al. "Two Chinese Hamster Ovary Glycosylation Mutants Affected in the Conversion of GDP-Mannose to GDP-Fucose," *Arch. Biochem. Biophys.* 249(2):533-545, (Sep. 1986).
Schaefer et al. "Immunoglobulin Domain Crossover as a Generic Approach for the Production of Bispecific IgG Antibodies," *Proc. Natl. Acad. Sci. USA* 108(27):11187-11192, (Jul. 5, 2011).
Schlaeger et al. "Transient Gene Expression in Mammalian Cells Grown in Serum-Free Suspension Culture," *Cytotechnology* 30:71-83, (1999).
Schlaeger. "The Protein Hydrolysate, Primalone RL, is a Cost-Effective Multiple Growth Promoter of Mammalian Cell Culture in Serum-Containing and Serum-Free Media and Displays Anti-Apoptosis Properties," *J. Immunol. Methods* 194:191-199, (1996).
Shields et al. "High Resolution Mapping of the Binding Site on Human IgG1 for FcγRI, FcγRII, FcγRIII, and FcRn and Design of IgG1 Variants with Improved Binding to the FcγR," *J. Biol. Chem.* 276(9):6591-6604, (Mar. 2, 2001).
Urlaub et al. "Isolation of Chinese Hamster Cell Mutants Deficient in Dihydrofolate Reductase Activity," *Proc. Natl. Acad. Sci. USA* 77(7):4216-4220, (Jul. 1980).
Van Dijk et al. "Human Antibodies as Next Generation Therapeutics," *Curr. Opin. Pharmacol.* 5:368-374, (2001).
Vijayalakshmi. "Antibody Purification Methods," *Appl. Biochem. Biotech.* 75:93-102, (1998).
Virnekäs et al. "Trinucleotide Phosphoramidites: Ideal Reagents for the Synthesis of Mixed Oligonucleotides for Random Mutagenesis," *Nucleic Acids Res.* 22(25):5600-5607, (Dec. 25, 1994).
Werner et al. "Appropriate Mammalian Expression Systems for Biopharmaceuticals," *Drug Res.* 48:870-880, (Aug. 1998).
Wright et al. "Effect of Glycosylation on Antibody Function: Implications for Genetic Engineering," 6*TIBTECH* 15:26-32, (Jan. 1997).
Yamane-Ohnuki et al. "Establishment of *FUT8* Knockout Chinese Hamster Ovary Cells: An Ideal Host Cell Line for Producing Completely Defucosylated Antibodies With Enhanced Antibody-Dependent Cellular Cytotoxicity," *Biotech. Bioeng.* 87:614-622, (2004, e-pub. Aug. 6, 2004).
Yazaki et al. "Expression of Recombinant Antibodies in Mammalian Cell Lines," Chapter 15 *in Methods in Molecular Biology* B.K.C. Lo, ed., Humana Press, Totowa, NJ, 248:255-268, (2003).
International Search Report dated Jan. 16, 2015, for PCT Application No. PCT/EP2014/071531, filed on Oct. 8, 2014, 6 pages.
Written Opinion dated Jan. 16, 2015, for PCT Application No. PCT/EP2014/071531, filed on Oct. 8, 2014, 5 pages.
Aggarwal et al. "Fibroblast Activation Protein Peptide Substrates Identified from Human Collagen I Derived Gelatin Cleavage Sites," *Biochemistry* 47(3):1076-1086, (Jan. 22, 2008).
Alt et al. "Novel Tetravalent and Bispecific IgG-Like Antibody Molecules Combining Single-chain Diabodies With the Immunoglobulin γ1 Fc or CH3 Region," *FEBS Lett.* 454(1-2):90-94, (Jul. 2, 1999).
Anonymous. "Production in yeasts of stable antibody fragments," *Expert Opinion on Therapeutic Patents* 7(2):179-183, (1997).
Atwell et al. "Stable Heterodimers From Remodeling the Domain Interface of a Homodimer Using a Phage Display Library," *J. Mol. Biol.* 270 (1):26-35 (1997).
Ausubel et al. Short Protocols in Molecular Biology, Greene Publishing and Wiley Interscience, New York, New York, (Table of Contents), (1987).
Avgeris et al. "Kallikrein-Related Peptidase Genes As Promising Biomarkers for Prognosis and Monitoring of Human Malignancies," Biol. Chem 391(5):505-511, (May 2010).
Bao et al. "HER2-Mediated Upregulation of MMP-1 Is Involved in Gastric Cancer Cell Invasion," *Arch Biochem Biophys* 499(1-2):49-55, (Jul. 2010).
Baserga et al. (2003). "The IGF-1 Receptor in Cancer Biology," *Int. J. Cancer* 107:873-877.
Beckman et al. "Antibody Constructs in Cancer Therapy. Protein Engineering Strategies to Improve Exposure in Solid Tumors," *Cancer* 109(2):170-179, (Jan. 15, 2007, e-pub. Dec. 11, 2006).
Berkman, R.A. et al. "Expression of the Vascular Permeability Factor/Vascular Endothelial Growth Factor Gene in Central Nervous System Neoplasms," *J. Clin. Invest.* 91:153-159, (Jan. 1993).
Bera et al. "A Bivalent Disulfide-Stabilized Fv With Improved Antigen Binding to erbB2," *J. Mol. Biol.* 281(3):475-483, (Aug. 21, 1998).
Bird et al. "Single-Chain Antigen-Binding Proteins," *Science* 242(4877):423-6, (Oct. 21, 1988).
Bird et al. "Single-Chain Antigen-Binding Proteins," *Science* 244(4903):409, *Erratum*, (Apr. 28, 1989).
Boado et al. "IgG-Single Chain Fv Fusion Protein Therapeutic for Alzheimer's Disease: Expression in CHO Cells and Pharmacokinetics and brain delivery in the rhesus monkey," *Biotechnology and Bioengineering* 105(3):627-635, (Feb. 15, 2010).
Borgström et al. "Complete Inhibition of Angiogenesis and Growth of Microtumors by Anti-Vascular Endothelial Growth Factor Neu-

(56) References Cited

OTHER PUBLICATIONS tralizing Antibody: Novel Concepts of Angiostatic Therapy from Intravital Videomicroscopy," *Cancer Research* 56:4032-4039, (1996).
Bostrom et al. "Variants of the Antibody Herceptin That Interact With HER2 and VEGF at the Antigen Binding Site," *Science* 323:1610-1614, (2009).
Briggs et al. "Cystatin E/M Suppresses Legumain Activity and Invasion of Human Melanoma," *BMC Cancer* 10(17):1-13, (Jan. 2010).
Brinkmann. "Disulfide-Stabilized Fv Fragments," Chapter 14 in 2 in Antibody Engineering, Kontermaan et al. eds., vol. 2, Springer-Verlag, Berlin Heidelberg, Germany, pp. 181-189, (Apr. 30, 2010).
Brinkmann et al., "A Recombinant Immunotoxin Containing a Disulfide-Stabilized Fv Fragment," *Proc. Natl. Acad. Sci. USA* 90(16):7538-7542, (1993).
Brocks et al. "A TNF Receptor Antagonistic scFv, Which is Not Secreted in Mammalian Cells, is Expressed as a Soluble Mono- and Bivalent scFv Derivative in Insect Cells," *Immunotechnology* 3: 173-184, (1997).
Brorson et al. "Mutational Analysis of Avidity and Fine Specificity of Anti-Levan Antibodies," *J. Immunol.* 163:6694-6701 (1994).
Brown, L.F. et al. "Expression of Vascular Permeability Factor (Vascular Endothelial Growth Factor) and its Receptors in Breast Cancer," *Human Pathol.* 26(1):86-91, (Jan. 1995).
Brown, L.F. et al. "Expression of Vascular Permeability Factor (Vascular Endothelial Growth Factor) and its Receptors in Adenocarcinomas of the Gastrointestinal Tract," *Cancer Res.* 53:4727-4735, (Oct. 1, 1993).
Brummell et al. "Probing the Combining Site of an Anti-Carbohydrate Antibody by Saturation-Mutagenesis: Role of the Heavy-Chain CDR3 Residues," *Biochemistry* 32(4):1180-1187 (1993).
Brunhouse et al. "Isotypes of IgG: Comparison of the Primary Structures of Three Pairs of Isotypes Which Differ in Their Ability to Activate Complement," *Mol Immunol.* 16(11): 907-917 (Nov. 1979).
Budtschanow et al. "System of Humoral Immunity Antibodies (Theme 2)," Guidance Manual for General Immunology, *Twer* (2008) p. 3, English Translation, 3 pages, (5 pages both English Equivalent and Russian Reference.
Burgess et al. "Possible Dissociation of the Heparin-Binding and Mitogenic Activities of Heparin-Binding (Acidic Fibroblast Growth Factor-1 From Its Receptor-Binding Activities by Site-Directed Mutagenesis of a Single Lysine Residue," *Journal of Cell Biology* 111:2129-2138, (Nov. 1990).
Burks et al. "In Vitro Scanning Saturation Mutagenesis of an Antibody Binding Pocket," *Proc. Natl. Acad. Sci. USA* 94(2):412-417 (1997).
Burton et al. "The C1q Receptor Site on Immunoglobulin G," *Nature* 288(5789):338-344, (Nov. 27, 1980).
Caron et al. "Engineered Humanized Dimeric Forms of IgG Are More Effective Antibodies," *J. Exp. Med.* 176(4):1191-1195, (Oct. 1, 1992).
Carro et al. "Serum Insulin-Like Growth Factor I Regulates Brain Amyloid-β Levels," *Nature Medicine* 8(12):1390-1397, (2002, e-pub. Nov. 4, 2002).
Carter. "Bispecific Human IgG by Design," *Immunol. Methods* 248:7-15, (2001).
Casset et al. "A Peptide Mimetic of an Anti-CD4 Monoclonal," *Biochem and Biophys Res Comm.* 307:198-205, (2003).
Castoldi et al. "Molecular Characterization of Novel Trispecific ErbB-cMet-IGF1R Antibodies and Their Antigen-Binding Properties," *Prot. Engin. Des. Selection* 25:551-560, (2012).
Céspedes et al. "Mouse Models in Oncogenesis and Cancer Therapy," *Clin. Transl. Oncol.* 8(5):318-329 (2006).
Chan, L.A. et al. "Variable Region Domain Exchange in Human IgGs Promotes Antibody Complex Formulation with Accompanying Structural Changes and Altered Effector Functions," *Molecular Immunology* 41(5):527-538. (2004).

Chernaia. "[Cathepsin L from human brain tumor. Purification and contents]," *Ukr Biokhim Zh.* 70(5):97-103, (Sep.-Oct. 1998). (English Translation of Abstract.) (Article in Russian).
Cheung, A.H. et al. "Endothelial Tie2/Tek Ligands Angiopoietin-1 (ANGPT1) and Angiopoietin-2 (ANGPT2): Regional Localization of the Human Genes to 8q22.3-q23 and 8p23," *Genomics* 48(3):389-391, (Mar. 15, 1998).
Chicheportiche et al. "TWEAK, A New Secreted Ligand in the Tumor Necrosis Factor Family That Weakly Induces Apoptosis," *J. Biol. Chem.* 272(51):32401-32410, (1997).
Chitnis et al. "The Type 1 Insulin-Like Growth Factor Receptor Pathway," *Clin. Cancer Res.* 14(20):6364-6370, (Oct. 16, 2008).
Chung et al., "Development of a novel albumin-binding prodrug that is cleaved by urokinase-type-plasminogen activator (uPA)," *Bioorg Med Chem Lett.* 16(19):5157-5163 (Oct. 1, 2006).
Coleman. "Effects of Amino Acid Sequence Changes on Antibody-Antigen Interactions," *Research in Immunol.* 145(1):33-38, (1994).
Connolly, D.T. et al. "Human Vascular Permeability Factor," *J. Biol. Chem.* 264(33):20017-20024, (Nov. 25, 1989).
Cordingley et al. "Substrate requirements of human rhinovirus 3C protease for peptide cleavage in vitro," *J. Biol. Chem.* 265(16):9062-9065, (1990).
Cortesio et al. "Calpain 2 and PTP1B function in a novel pathway with Src to regulate invadopodia dynamics and breast cancer cell invasion," *J. Cell Biol.* 180(5):957-971, (Mar. 10, 2008).
Coxon et al. "Combined treatment of angiopoietin and VEGF pathway antagonists enhances antitumor activity in preclinical models of colon carcinoma," *99th AACR Annual Meeting*, Abstract #1113, (Apr. 2008).
Crawford et al. "Matrix metalloproteinase-7 is expressed by pancreatic cancer precursors and regulates acinar-to-ductal metaplasia in exocrine pancreas," *J. Clin. Invest.* 109(11):1437-1444, (Jun. 2002).
Cudic et al. "Extracellular proteases as targets for drug development," *Curr. Protein Pept. Sci.* 10(4):297-307, (Aug. 2009).
Cuesta et al. "Multivalent Antibodies: When Design Surpasses Evolution," *Trends Biotech.* 28:355-362, (2010).
Cullen et al. "Granzymes in cancer and immunity," *Cell Death Differ.*17(4):616-623, (Apr. 2010).
Dall'Acqua, W. et al. "Contribution of Domain Interface Residues to the Stability of Antibody CH3 Domain Homodimers", *Biochemistry*, 37:9266-9273, (1998).
Davis et al. "SEEDbodies: Fusion Proteins Based on Strand-Exchange Engineered Domain (SEED) $C_H3$ Heterodimers in an Fc Analogue Platform for Asymmetric Binders or Immunofusions and Bispecific Antibodies," *Protein Engineering Design & Selection* 23(4):195-202, (2010, e-pub. Feb. 4, 2010).
Davies et al. "Expression of GnTIII in a Recombinant Anti-CD20 CHO Production Cell Line: Expression of Antibodies With Altered Glycoforms Leads to an Increase in ADCC Through Higher Affinity for FcγRIII," *Biotechnol. Bioeng.* 74:288-294, (2001).
Dennis. "Off by a Whisker," *Nature* 442:739-741, (2006).
Deyev. "Multivalency: the Hallmark of Antibodies Used for Optimization of Tumor Targeting by Design," *Bioessays* 30(9):904-918, (2008).
Dimmock, N.J. et al. "Valency of Antibody Binding to Virions and Its Determination by Surface Plasmon Resonance," *Rev. Med. Virol.* 14:123-135, (2004).
Donaldson et al. "Design and Development of Masked Therapeutic Antibodies to Limit Off-Target Effects: Application to Anti-EGFR antibodies," *Cancer Biology & Therapy* 8(22):2145-2150, (Nov. 15, 2009).
Dufner et al. "Harnessing Phage and Ribosome Display for Antibody Optimization," *Trends Biotechol.* 24(11):523-29 (2006).
Dvorak, H. et al. "Vascular Permeability Factor/Vascular Endothelial Growth Factor, Microvascular Hyperpermeability, and Angiogenesis," *Am. J. Pathol.* 146(5):1029-1039, (May 1995).
Edelman et al. "The Covalent Structure of an Entire γG Immunoglobulin Molecule," *Proc. Natl. Acad. Sci. USA* 63:78-85, (1969).
Fiedler et al. "Purification and Characterisation of His-Tagged Antibody Fragments," Chapter 17 *in Antibody Engineering*, Kontermann and Dubel (Eds.), Springer Lab Manuals, PP. 243-256, (2001).

(56) References Cited

OTHER PUBLICATIONS

Fenn et al. "Crystal Structure of an Anti-Ang2 CrossFab Demonstrates Complete Structural and Functional Integrity of the Variable Domain," *PLOS ONE* 8(4):e61953 (Apr. 1, 2013).
Ferrara, N. et al. "The Biology of Vascular Endothelial Growth Factor," *Endocr. Rev.* 18(1):4-25, (1997).
Fischer et al. "Bispecific Antibodies: Molecules That Enable Novel Therapeutic Strategies," *Pathobiology* 74:3-14, (2007).
Fujimori et al. "A Modeling Analysis of Monoclonal Antibody Percolation Through Tumors: A Binding-Site Barrier," *J. Nuc. Med.* 31(7):1191-1198, (Jul. 1990).
Galamb et al. "Inflammation, Adenoma and Cancer: Objective Classification of Colon Biopsy Specimens With Gene Expression Signature," *Dis Markers* 25(1):1-16, (2008).
Gerspach et al. "Target-Selective Activation of a TNF Prodrug by Urokinase-Type Plasminogen Activator (uPA) Mediated Proteolytic Processing at the Cell Surface," *Cancer Immunol. Immunother* 55:1590-1600 (2006).
Gold et al. "A Novel Bispecific, Trivalent Antibody Construct for Targeting Pancreatic Carcinoma," *Cancer Res.* 68(12):4819-4826, (2008).
Goldenberg et al. "Bi-Specific Antibodies That Bind Specific Target Tissue and Targeted Conjugates," Derwent Information Ltd., 12 pages, (2012).
Greenwood et al. "Structural Motifs Involved in Human IgG Antibody Effector Functions,". *Eur. J. Immunology* 23(5):1098-1104, (May 1993).
Grote et al. "Bispecific Antibody Derivatives Based on Full-Length IgG Formats," Chapter 16 in *Methods in Molecular Biology* 901:247-263, (2012).
Gunasekaran et al. "Enhancing Antibody Fc Heterodimer Formation Through Electrostatic Steering Effects: Applications to Bispecific Molecules and Monovalent IgG," *The Journal of Biological Chemistry* 285(25):19637-19646, (Jun. 18, 2010).
Hartog et al. "The Insulin-like Growth Factor 1 Receptor in Cancer: Old Focus, New Future," *European Journal of Cancer*, Pergamon Press, Oxford, GB, 43(13):1895-1904, (Aug. 23, 2007).
Hellings et al. "Interleukin-17 Orchestrates the Granulocyte Influx Into Airways After Allergen Inhalation in a Mouse Model of Allergic Asthma" *Am. J. Respir. Cell Mol. Biol.* 28:42-50, (2003).
Henry et al. "Clinical implications of fibroblast activation protein in patients with colon cancer," *Clin. Cancer Res.* 13(6):1736-1741, (Mar. 15, 2007).
Hezareh et al. "Effector Function Activities of a Panel of Mutants of a Broadly Neutralizing Antibody against Human Immunodeficiency Virus Type 1," *Journal of Virology* 75(24):12161-12168, (Dec. 2001).
Hollander. "Bispecific antibodies for cancer therapy," *Immunotherapy* 1(2):211-222, (Mar. 2009).
Holliger et al. "Engineered antibody fragments and the rise of single domains," *Nat Biotechnol.* 23(9):1126-1136, (Sep 2005).
Hust et al. "Single Chain Fab (scFab) Fragment," *BMC Biotechnology* 7(14):1-15, (Mar. 8, 2007).
Huston, J.S. et al. "Medical Applications of Single-Chain Antibodies," *Intern. Rev. Immunol.* 10(2-3):195-217, (1993).
Huston et al. "Protein Engineering of Antibody Binding Sites: Recovery of Specific Activity in an Anti-Digoxin Single-Chain Fv analogue Produced in *Escherichia coli,*" *Proc. Natl. Acad. Sci. U.S.A.* 85(16):5879-5883, (Aug. 1988).
Ibragimova et al. "Stability of the β-Sheet of the WW domain: A molecular dynamics simulation study," *Biophysical Journal* 77:2191-2198, (Oct. 1999).
Jang et al. "The Structural Basis for DNA Binding by an Anti-DNA Auto Antibody," *Mol. Immunol.* 35(18):1207-1217 (1998).
Jefferis et al. "IgG-Fc-Mediated Effector Functions: Molecular Definition of Interaction Sites for Effector Ligands and the Role of Glycosylation," *Immunol Rev.* 163:59-76, (1998).

Jendreyko et al. "Simultaneous, Phenotypic Knockout of VEGF-R2 and Tie-2 With an Intradiabody Enhances Antiangiogenic Effects In Vivo," Therapieoptimierung and Risikostratifizierung, Scripps Research Institute, 218:143-151, (2006).
Jia et al. "A novel trifunctional IgG-like bispecific antibody to inhibit HIV-1 infection and enhance lysis of HIV by targeting activation of complement," *Virology Journal* 7(142):1-4, (Jun. 29, 2010).
Johnson et al. "Construction of Single-Chain Fv Derivatives Monoclonal Antibodies and their Production in *Escherichia coli,*" *Methods Enzymol.* 203:88-98, (1991).
Kabat et al. *Sequences of Proteins of Immunological Interest* (Table of Contents and Introduction), 5th edition, Bethesda, MD: Public Health Service, NIH, vol. 1, (1991).
Karadag et al. "ADAM-9 (MDC-9/meltrin-γ), a Member of the A Disintegrin and Metalloproteinase Family, Regulates Myeloma-Cell-Induced Interleukin-6 Production in Osteoblasts by Direct Interaction With the αvβ5 Integrin," *Blood* 107(8):3271-3278, (Apr. 2006).
Kazama et al., "Hepsin, A Putative Membrane-Associated Serine Protease, Activates Human Factor VI and initiates a Pathway of Blood Coagulation on the Cell Surface Leading to Thrombin Formation," *JBC* 270:66-72, (1995).
Keck, P.J. et al. "Vascular Permeability Factor, An Endothelial Cell Mitogen Related to PDGF," *Science* 246:1309-1312, (1989).
Kim et al. "Inhibition of Vascular Endothelial Growth Factor-Induced Angiogenesis Suppresses Tumour Growth In Vivo," *Nature* 362:841-844, (1993).
Kim, I. et al. "Molecular Cloning and Characterization of a Novel Angiopoietin Family Protein, Angiopoietin-3," *FEBS Let.* 443:353-56, (1999).
Kim, I. et al. "Molecular Cloning, Expression, and Characterization of Angiopoietin-Related Protein. Angiopoietin-Related Protein Induces Endothelial Cell Sprouting," *J. Biol. Chem.* 274(37):26523-26528, (Sep. 1999).
Kleinschmidt et al. "Design of a Modular Immunotoxin Connected by Polyionic Adapter Peptides," *J. Mol. Biol.* 327(2):445-452, (Mar. 21, 2003).
Kobayashi et al. "Similarities in the Biodistribution of Iodine-Labeled Anti-Tac Single-Chain Disulfide-Stabilized Fv Fragment and Anti-Tac Disulfide-Stabilized Fv Fragment," *Nuclear Medicine & Biology* 25:387-393, (1998).
Kobayshi et al. "Tryptophan H33 plays an important role in pyrimidine (6-4) pyrimidone photoproduct binding by a high-affinity antibody," *Protein Engineering* 12(10):879-844 (1999).
Kodukula et al. "Biosynthesis of phosphatidylinositol glycan-anchored membrane proteins. Design of a simple protein substrate to characterize the enzyme that cleaves the COOH-terminal signal peptide," *The Journal of Biological Chemistry* 266(7):4464-4470 (Mar. 5, 1991).
Komiyama et al. "IL-17 plays an important role in the development of experimental autoimmune encephalomyelitis" *J Immunol* 177:566-573, (2006).
Kotake et al. "IL-17 in synovial fluids from patients with rheumatoid arthritis is a potent stimulator of osteoclastogenesis," *J. Clin. Invest.* 103:1345-1352, (1999).
Krugmann et al. "Structural Requirements for Assembly of Dimeric IgA Probed by Site-Directed Mutagenesis of J Chain and a Cysteine Residue of the α-chain CH2 Domain," *The Journal of Immunology* 159:244-249, (1997).
Kumar et al. "Molecular Cloning and Expression of the Fabs of Human Autoantibodies in *Escherichia coli,*" *J. Biol. Chem.* 275(45):35129-35136, (Nov. 10, 2000).
Lamkanfi et al. "Inflammasomes: guardians of cytosolic sanctity," *Immunol. Rev.* 227(1):95-105, (Jan. 2009).
Lazar et al. "Transforming Growth Factor α: Mutation of Aspartic Acid 47 and Leucine 48 Results in Different Biological Activities," *Molecular and Cellular Biology* 8(3):1247-1252, (Mar. 1988).
Lee et al. "Using Substrate Specificity of Antiplasmin-Cleaving Enzyme for Fibroblast Activation Protein Inhibitor Design," *Biochemistry* 48(23):5149-5158, (Jun. 16, 2009).
Leeman et al. "The Structure, Regulation, and Function of Human Matrix Metalloproteinase-13," *Crit. Rev Biochem Mol. Biol.* 37(3):149-166, (2002).

(56) References Cited

OTHER PUBLICATIONS

Leitzgen et al. "Assembly of Immunoglobulin Light Chains as a Prerequisite for Secretion," *Journal of Biological Chemistry* 272(5):3117-3123, (Jan. 31, 1997).

Leung, D.W. et al. "Vascular Endothelial Growth Factor Is a Secreted Angiogenic Mitogen," *Science* 246:1306-1309, (Dec. 8, 1989).

Lewis, M.L. et al. "Generation of Bispecific IgG Antibodies by Structure-Based Design on an Orthogonal Fab Interface," *Nature Biotechnology* 32(2):191-198, (Feb. 1, 2014).

Lin et al. "Structure-Function Relationships in Glucagon: Properties of Highly Purified Des-His-, Monoiodo-, and [Des-Asn$^{28}$, Thr$^{29}$](homoserine lactone$^{27}$)-glucagon," *Biochemistry USA* 14:1559-1563, (1975).

Liang et al. "Cross-Species Vascular Endothelial Growth Factor (VEGF)-blocking Antibodies Completely Inhibit the Growth of Human Tumor Xenografts and Measure the Contribution of Stromal VEGF," *Journal of Biological Chemistry* 281 (2):951-961, (2006).

Liotta et al. "Metastatic Potential Correlates With Enzymatic Degradation of Basement Membrane Collagen," *Nature* 284(5751) 67-68, (Mar. 6, 1980).

Liu et al. "Clinical and imaging diagnosis of primary hepatic lymphoma," *J First Mil Med. Univ.* 25(10):1290-1292, three pages, (2005). (Translation of the Abstract Only.).

Lodish et al. "Post-Translational Modifications and Quality Control in the Rough ER," Chapter 17, Section 17.6 in *Molecular Cell Biology*, 4th edition, W.H. Freeman and Company, New York, pp. 707-712, (1999).

Lopez-Otin et al. "The Regulatory Crosstalk Between Kinases and Proteases in Cancer," *Nat. Rev. Cancer* 10(4):278-292, (Apr. 2010).

Love et al. "Recombinant Antibodies Possessing Novel Effector Functions," *Methods in Enzymology* 178:515-527, (1989).

Lu et al. "A Fully Human Recombinant IgG-Like Bispecific Antibody to Both the Epidermal growth Factor Receptor and the Insulin-Like Growth Factor Receptor for Enhanced Antitumor Activity," *The Journal of Biological Chemistry* 280(20):19665-19672, (May 20, 2005).

Lu et al. "ADAMTS1 and MMP1 Proteolytically Engage EGF-like Ligands in an Osteolytic Signaling Cascade for Bone Metastasis," *Genes Dev.* 23(16):1882-1894, (Aug. 2009).

Lukas et al. "Inhibition of C1-Mediated Immune Hemolysis by Monomeric and Dimeric Peptides from the Second Constant Domain of Human Immunoglobulin G," *The Journal of Immunolgy* 127(6):2555-2560, (Dec. 1981).

Lund et al. "Oligosaccharide-Protein Interactions in IgG Can Modulate Recognition by Fcγ Receptors," *FASEB Journal* 9:115-119, (1995).

Lynch et al. "TWEAK Induces Angiogenesis and Proliferation of Endothelial Cells," *J. Biol. Chem.* 274(13):8455-8459, (Mar. 26, 1999).

Maisonpierre, P.C. et al. "Angiopoietin-2, A Natural Antagonist for Tie2 that Disrupts in vivo Angiogenesis," *Science* 277:55-60, (Jul. 4, 1997).

Mamoune et al. "Calpain-2 as a target for limiting prostate cancer invasion," *Cancer Res.* 63(15):4632-4640, (Aug. 2003).

Marsters et al. "Identification of a Ligand for the Death-Domain-Containing Receptor Apo3," *Curr. Biol.* 8(9):525-528, (1998).

Marvin et al. "Recombinant approaches to IgG-like bispecific antibodies," *Acta Pharmacol. Sin.* 26:649-658, (2005).

Marvin et al. "Bispecific antibodies for dual-modality cancer therapy: killing two signaling cascades with one stone," *Curr. Opin. Drug Discov. Devl.* 9:184-193, (2006).

Matrisian. "Cancer biology: extracellular proteinases in malignancy," *Curr. Biol.* 9(20):R776-R778, (Oct. 1999).

Mattern, J. et al. "Association of Vascular Endothelial Growth Factor Expression With Intratumoral Microvessel Density and Tumour Cell Proliferation in Human Epidermoid Lung Carcinoma," *Brit. J. Cancer* 73:931-934, (1996).

Matusevicius et al. "Interleukin-17 mRNA Expression in Blood and CSF Mononuclear Cells is Augmented in Multiple Sclerosis," *Multiple Sclerosis* 5:101-104, (1999).

McLean, G.R. et al. "A point mutation in the CH3 domain of human IgG3 inhibits antibody secretion without affecting antigen specificity", *Molecular Immunology*, 42:1111-1119, (2005).

Meissner et al. "Transient Gene Expression: Recombinant Protein Production with Suspension-Adapted HEK293-EBNA Cells," *Biotechnology and Bioengineering* 75:197-203, (2001).

Melnyk et al. "Vascular Endothelial Growth Factor Promotes Tumor Dissemination by a Mechanism Distinct from Its Effect on Primary Tumor Growth," *Cancer Research* 56:921-924, (1996).

Metz et al. "Bispecific Antibody Derivatives With Restricted Binding Functionalities that are Activated by Proteolytic Processing," *Prot. Eng. Des. Sel.* 25:571-580, (2012).

Michaelson et al. "Anti-Tumor Activity of Stability-Engineered Igg-Like Bispecific Antibodies Targeting TRAIL-R2 and LTβR," *MAbs* 1(2):128-141, (Mar. 2009, e-pub. Mar. 11, 2009).

Miller et al. "Design, Construction, and In Vitro Analyses of Multivalent Antibodies," *J. Immunol.* 170:4854-4861, (2003).

Mimura et al. "Role of Oligosaccharide Residues of IgG1-Fc in FcγRIIb Binding," *The Journal of Biological Chemistry* 276(49): 45539-45547, (Dec 7, 2001).

Minn et al. "Genes that Mediate Breast Cancer Metastasis to Lung," *Nature* 436(7050):518-524, (Jul. 2005), 15 pages.

Mirny, L. et al. "Protein Folding Theory: From Lattice to All-Atom Models", *Annu. Rev. Biophys. Biomol. Struct.*, 30:361-96, (2001).

Morgan et al. "The N-terminal End of the $C_H2$ Domain of Chimeric Human IgG1 anti-HLA-DR is Necessary for C1q, FcγRI and Fc≡RIII Binding," *Immunology* 86:319-324, (1995).

Morrison. "Success in Specification," *Nature* 368:812-813, (Apr. 1994).

Mukhopadhyay et al. "Matrix metalloproteinase-12 is a therapeutic target for asthma in children and young adults," *J. Allergy Clin Immunol.* 126:70-76, (2010).

Müller et al. "Recombinant Bispecific Antibodies for Cellular Cancer Immunotherapy," *Current Opinion in Molecular Therapeutics* 9:319-326, (2007).

Müller et al. "Bispecific Antibodies," Chapter 2 in Handbook of Therapeutic Antibodies, Dübel, S. ed., Wiley-VCH Verlag GmbH & Company KGaA, Weinheim, pp. 345-378, (2007).

Müller et al. "The First Constant Domain ($C_H1$ and $C_L$) of an Antibody Used as Heterodimerization Domain for Bispecific Miniantibodies," *FEBS Letters* 422:259-264, (1998).

Myatt et al. "Pathogenic Potential of Human Monoclonal Immunoglobulin Light Chains: Relationship of in vitro Aggregation to in vivo Organ Deposition," *Proc. Natl. Acad. Sci. USA* 91:3034-3038, (Apr. 1994).

Nagaoka et al. "Single Amino Acid Substitution in the Mouse IgG1 Fc Region Induces Drastic Enhancement of the Affinity to Protein A," *Protein Engineering* 16(4):243-245, (2003).

Netzel-Arnett et al. "Sequence Specificities of Human Fibroblast and Neutrophil Collagenases," *J. Biol. Chem.* 266(11):6747-6755, (Apr. 15, 1991).

Netzel-Arnett et al. "Comparative Sequence Specificities of Human 72- and 92-kDa Gelatinases (Type IV Collagenases) and PUMP (matrilysin)," *Biochemistry* 32(25):6427-6432, (Jun. 29, 1993).

Niwa et al. "IgG Subclass-Independent Improvement of Antibody-Dependent Cellular Cytotoxicity by Fucose Removal From Asn$^{297}$-Linked Oligosaccharides," *J. Immunol. Methods* 306:151-160, (2005).

Novotný, J. et al. "Structural invariants of antigen binding: Comparison of immunoglobulin $V_L$-$V_H$ and $V_L$-$V_L$ domain dimmers", *Proc. Natl. Acad. Sci. USA*, 82:4592-4596, (1985).

Ohno et al. "Antigen-binding specificities of antibodies are primarily determined by seven residues of $V_H$," *Proc. Natl. Acad. Sci. USA* 82(9):2945-2949, (May 1985).

Olafsen, T. et al. "Complement-Mediated lysis of Cultured Osteosarcoma Cell Lines Using Chimeric Mouse/Human TP-1 IgG1 and IgG3 Antibodies," *Cancer Immunol. Immunother.* 48:411-418, (1999).

Oliner et al. "Suppression of Angiogenesis and Tumor Growth by Selective Inhibition of Angiopoietin-2," *Cancer Cell* 6:507-516, (2004).

(56) References Cited

OTHER PUBLICATIONS

Orcutt, et al. "A Modular IgG-scFv Bispecific Antibody Topology," *Protein Engineering, Design & Selection* 23(4):221-228, (Apr. 2010, e-pub. Dec. 17, 2009).
Pace et al. "How to Measure and Predict the Molar Absorption Coefficient of a Protein," *Protein Science* 4(11): 2411-2423, (Nov 1995).
Pakula, A.A."Genetic Analysis of Protein Stability and Function," *Annu. Rev. Genet.* 23:289-310, (1989).
Pan, Q. et al. "Blocking Neuropilin-1 Function Has an Additive Effect with nti-VEGF to Inhibit Tumor Growth," *Cancer Cell* 11:53-67, (Jan. 2007).
Paul. "Immunoglobulins: Structure and Function," *in Fundamental Immunology*, Jeske, D.D. et al.New York, New York, Raven Press, p. 131-165. (1 page translation of 7.9.1 Disculfide Bonds), (1984).
Pleass et al. "Identification of Residues in the CH2/CH3 Domain Interface of IgA Essential for Interaction With the Human fcα Receptor (Fcα R) CD89," *The Journal of Biology Chemistry* 274(33):23508-23514, (Aug. 13, 1999).
Plückthun et al. "New Protein Engineering Approaches to Multivalent and Bispecific Antibody Fragments," *Immunotechnology* 3:83-105, (1997).
PreScission Protease, GE Healthcare Catalogue No. 27-0843-01, located at http://www.gelifesciences.com/webapp/wcs/stores/servlet/productById/en/GELifeScience, last visited on Jul. 10, 2013, one page.
Radaev et al. "Recognition of IgG by Fcγ Receptor," *The Journal of Biological Chemistry* 276(19): 16478-16483, (May 11, 2001).
Rajagopal et al. "A Form of Anti-Tac(Fv) Which is Both Single-chain and Disulfide Stabilized: Comparison with its single-chain and Disulfide-stabilized Homologs," *Protein Engineering* 10(12):1453-1459, (1997).
Raju. "Glycosylation Variations with Expression Systems and Their Impact on Biological Activity of Therapeutic Immunoglobulins," *BioProcess International* 1(4): 44-53, (Apr. 2003).
Rawlings. "A Large and Accurate Collection of Peptidase Cleavages in The MEROPS Database," *Database* (Oxford), pp. 1-14, (2009, e-pub. Nov. 2, 2009).
Reiter et al. "Stabilization of the Fv Fragments in Recombinant Immunotoxins by Disulfide Bonds Engineered into Conserved Framework Regions," *Biochemistry* 33:5451-5449, (1994).
Reiter et al. "Improved Binding and Antitumor Activity of a Recombinant Anti-erbB2 Immunotoxin by Disulfide Stabilization of the Fv fragment," *JBC* 269:18327-18331, (1994).
Reiter et al. "Engineering Interchain Disulfide Bonds Into Conserved Framework Regions of Fv Fragments: Improved Biochemical Characteristics of Recombinant Immunotoxins Containing Disulfide-Stabilized Fv," *Protein Eng.* 7(5):697-704, (May 1994).
Reiter et al., "Cytotoxic and Antitumor Activity of a Recombinant Immunotoxin Composed of Disulfide-Stabilized Anti-Tac Fv Fragment and Truncated Pseudomonas exotoxin," *International Journal of Cancer* 58:142-149, (1994).
Reiter et al., "Antitumor Activity and Pharmacokinetics in Mice of a Recombinant Immunotoxin Containing a Disulfide-Stabilized Fv Fragment," *Cancer Research* 54:2714-2718, (1994).
Reiter et al. "Antibody Engineering of Recombinant Fv Immunotoxins for Improved Targeting of Cancer: Disulfide-Stabilized Fv Immunotoxins," *Clin. Cancer Res.* 2(2):245-252, (Feb. 1, 1996).
Reiter et al. "Disulfide Stabilization of Antibody Fv: Computer Predictions and Experimental Evaluation," *Protein Engineering* 8:1323-1331, (1995).
Reiter et al. "Construction of a Functional Disulfide-Stabilized TCR Fv Indicates That Antibody and TCR Fv Frameworks Are Very Similar in Structure," *Immunity* 2:281-287, (1995).
Reiter et al. "Engineering Antibody Fv Fragments for Cancer Detection and Therapy: Disulfide-Stabilized Fv Fragments," *Nature Biotechnology* 14:1239-1245, (1996).
Reyes, A.E. et al. "Pharmacokinetics of a Novel One Armed Antibody to C-Met in Mice, Rats and Monkeys," Genentech, Inc., *Amer. Assn. Pharm. Sci.* 10:S1, (2008).

Roitt et al. "Immunology," English Translation by McElroy Translation Company, Moscow *Mir* (2000), p. 110-111, eight pages.
Roitt, A. et al. "Multispecific Antibodies Comprising Full Length Antibodies and Single Chain Fab Fragments," *Immunology*, English Translation, Moscow:*Mir*, pp. 388-389, (2000).
Rossi, E.A. et al. "Multivalent Anti-CD20/Anti-CD22 Bispecific Antibody Fusion Proteins Made by the DNL Method Show Potent Lymphoma Cytotoxicity," *Blood, American Society of Hematology* 108(11):707A, Poster Board No. Session 673-II, Abstract No. 2495, from 48th Annual Meeting of the American Society of Hematology, Orland, Florida, Dec. 9-12, 2006, (2006).
Routier et al. "The Glycosylation Pattern of a Humanized IgGI Antibody (D1.3) Expressed in CHO Cells," *Glycoconjugate Journal* 14:201-207, (1997).
Rudikoff et al. "Single Amino Acid Substitution Altering Antigen-Binding Specificity," *Proc. Natl. Acad. Sci. USA* 79: 1979-1983, (1982).
Rudnick et al. "Affinity and Avidity in Antibody-Based Tumor Targeting," *Cancer Biotherapy & Radiopharmaceuticals* 24(2):155-161, (2009).
Ruppert et al. "Protease levels in breast, ovary and other gynecological tumor tissues: prognostic importance in breast cancer," *Cancer Detect. Prev.* 21(5):452-459, (1997).
Sambrook et al. Molecular Cloning: A Laboratory Manual "The Table of Contents" Cold Spring Harbor, New York: Cold Spring Harbor Laboratory Press, (1989).
Schlatter et al. "On the Optimal Ratio of Heavy to Light Chain Genes for Efficient Recombinant Antibody Production by CHO Cells," *Biotechnol. Prog.* 21:122-133, (2005, e-pub. Nov. 16, 2004).
Schmidt et al. "Suppression of Metastasis Formation by a Recombinant Single Chain Antibody-Toxin Targeted to Full-length and Oncogenic Variant EGF Receptors," *Oncogene* 18:1711-1721, (1999).
Schmiedl et al. "Expression of a bispecific dsFv-dsFv' antibody fragment in *Escherichia coli*," *Protein Engineering* 13(10):725-734, (Oct. 2000).
Schmiedl et al. "Effects of Unpaired Cysteines on Yield, Solubility and Activity of Different Recombinant Antibody Constructs Expressed in *E. coli*" *Journal of Immunological Methods* 242:101-114, (2000).
Schoonjans, et al. "Fab Chains as an Efficient Heterodimerization Scaffold for the Production of Recombinant Bispecific and Trispecific Antibody Derivatives," *Journal of Immunology* 165:7050-7057, (2000).
Schwartz et al. "A Superactive Insulin: (B10-aspartic acid]insulin(human)," *Proc. Natl. Acad. Sci. USA* 84:6408-6411, (Sep. 1987).
Scott et al. "Biologic Protease Inhibitors As Novel Therapeutic Agents," *Biochimie* 92(11):1681-1688, (Nov. 2010, e-pub. Mar. 24, 2010).
Shen et al. "Single Variable Domain Antibody as a Versatile Building Block for the Construction of IgG-Like Bispecific Antibodies," *Journal of Immunological Methods* 318:65-74, (2007).
Shen et al. "Single Variable Domain-IgG fusion: A Novel Recombinant Approach to Fc Domain-Containing Bispecific Antibodies," *J. of Biological Chemistry* 281(16):10706-10714, (Apr. 21, 2006, e-pub. Feb. 15, 2006).
Shields et al. "Lack of Fucose on Human IgG1 N-Linked Oligosaccharide Improves Binding to Human FcγRIII and Antibody-dependent Cellular Toxicity," *J Biol Chem.* 277(30):26733-26740, (Jul. 26, 2002).
Shinkawa et al. "The Absence of Fucose but Not the Presence of galactose or Bisecting N-Acetylglucosamine of Human IgG1 Complex-Type Oligosaccharides Shows the Critical Role of Enhancing Antibody-Dependent Cellular cytotoxicity," *J. Biol. Chem.* 278 (5) 3466-3473, (2003).
Simmons et al. "Expression of full-length immunoglobulins in *Escherichia coli*: Rapid and Efficient production of aglycosylated antibodies," *Journal of Immunological Methods* 263:133-147, (2002).
Simon et al. "Antibody Domain Mutants Demonstrate Autonomy of the Antigen Binding Site," *The EMBO Journal* 9(4):1051-1056, (1990).
Singer, M. et al. "Genes and Genomes," Moscoer, MIR 1(1998) 63-64 (With English Translation).

(56) References Cited

OTHER PUBLICATIONS

Smith-Gill et al. "Contributions of Immunoglobulin Heavy and Light Chains to Antibody Specificity for Lysozyme and Two Haptens," *J. Immunol.* 139(12):4135-4144, (Dec. 15, 1987).

Song et al. "Light Chain of Natural Antibody Plays a Dominant Role in Protein Antigen Binding," *Biochem. Biophys. Res. Comm.* 268(2):390-394, (Feb. 16, 2000).

Stetler-Stevenson et al. "Progelatinase A activation during tumor cell invasion," *Invasion Metastasis* 14(1-6):259-268, (1994-1995).

Stevenson et al. "A Chimeric Antibody With Dual Fc Regions (bisFabFc) Prepared by Manipulations at the IgG Hinge," *Anti-cancer Drug Des.* 3(4):219-230, (Mar. 1989).

Stork et al. "A Novel Tri-Functional Antibody Fusion Protein With Improved Pharmacokinetic Properties Generated by Fusing a Bispecific Single-Chain Diabody With an Albumin-Binding Domain From Streptococcal Protein G," *Protein Eng. Des. Sel.* 20(11):569-576, (Nov. 2007, e-pub. Nov. 3, 2007).

Surati, M. et al. "Role of MetMAb (OA-5D5) in c-MET Active lung Malignancies," *Expert Opin. Biol. Ther.* 11(12):1655-1662, (2011).

Talmadge et al. "Murine Models to Evaluate Novel and Conventional Therapeutic Strategies for Cancer," *Am. J. Pathol.* 170(3):793-804, (Mar. 2007).

Tao et al. "The Differential Ability of Human IgG1 and IgG4 to Activate Complement is Determined by the COOH-terminal Sequence of the $C_H2$ Domain," *J. Exp. Med* 173:1025-1028, (Apr. 1991).

Terpe. "Overview of Tag Protein Fusions: From Molecular and Biochemical Fundamentals to Commercial Systems," *Appl Microbiol Biotechnol* 60:523-533, (2003; E-Pub. Nov. 7, 2002).

Thommesen et al. "Lysine 322 in the Human IgG3 $C_H2$ Domain Is Crucial for Antibody Dependent Complement Activation," *Molecular Immunology* 37:995-1004, (2000).

Thurber et al. "Antibody Tumor Penetration: Transport Opposed by Systemic and Antigen-Mediated Clearance," *Adv. Drug Deliv. Rev.* 60(12):1421-1434, (Sep. 2008, e-Pub. Apr. 24, 2008).

Torres, M. et al. "Variable-Region-Identical Antibodies Differing in Isotype Demonstrate Differences in Fine Specificity and Idiotype", *The Journal of Immunology*, 174:2132. (2005).

Tripathi et al. "Laminin-332 Is a Substrate for Hepsin, A Protease Associated With Prostate Cancer Progression," *JBC* 283:30576-30584, (2008).

Ueki et al. "Expression of Hepatocyte Growth Factor and its Receptor c-met Proto-Oncogene in Hepatocellular Carcinoma," *Hepatology* 25(4):862-866, (1997).

Umaña et al. "Engineered Glycoforms of an Antineuroblastoma IgG1 with Optimized Anibody-Dependent Cellular Cytotoxic Activity," *Nature Biotechnology* 17(2):176-180 (Feb. 1999).

Van Spriel et al. "Immunotherapeutic perspective for bispecific antibodies," *Immunology Today* 21(8):391-397, (Aug. 2000).

Van'T Veer et al. "Gene expression profiling predicts clinical outcome of breast cancer," *Nature* 415(6871):530-536, (Jan. 2002).

Vazquez-Ortiz et al. "Overexpression of cathepsin F, matrix metalloproteinases 11 and 12 in cervical cancer," *BMC Cancer* 5:68, (Jun. 30, 2005).

Velasco et al. "Human Cathepsin O. Molecular Cloning From a Breast Carcinoma, Production of the Active Enzyme in *Escherichia coli*, and Expression Analysis in Human Tissues," *J. Biol. Chem.* 269(43):27136-27142, (Oct. 28, 1994).

Veveris-Lowe et al., "Seminal Fluid Characterization for Male Fertility and Prostate Cancer: Kallikein-Related Serine Proteases and whole Proteome Approaches," *Semin Thromb Hemost.* 33(1):87-99, (2007).

Voskoglou-Nomikos et al. "Clinical Predictive Value of the in Vitro Cell Line, Human Xenograft, and Mouse Allograft Preclinical Cancer Models," *Clin. Can. Res.* 9:4227-4239, (Sep. 15, 2003).

Walker et al. "Efficient and Rapid Affinity Purification of Proteins Using Recombinant Fusion Proteases," *Bio/Technology* 12:601-605, (1994).

Wallasch et al. "Heregulin-Dependent Regulation of HER2/neu Oncogenic Signaling by Heterodimerization With HER3," *EMBO J.* 14(17):4267-4275, (1995).

Ward et al. "Binding Activities of a Repertoire of Single Immunoglobulin Variable Domains Secreted From *Escherichia coli*," *Nature* 341:544-546, (Oct. 12, 1989).

Warren et al. "Regulation by Vascular Endothelial Growth Factor of Human Colon Cancer Tumorigenesis in a Mouse Model of Experimental Liver Metastasis," *J. Clin. Invest.* 95:1789-1797, (1995).

Webber et al. "Preparation and characterization of a Disulfide-Stabilized Fv Fragment of the Anti-Tac Antibody: Comparison With Its Single-Chain Analog," *Molecular Immunology* 32:249-258, (1995).

Wielockx et al. "Matrilysin (matrix metalloproteinase-7): A New Promising Drug Target in Cancer and Inflammation?" *Cytokine Growth Factor Rev.* 15(2-3):111-115, (Apr.-Jun. 2004).

Willems et al. "Optimizing Expression and purification From Cell Culture Medium of Trispecific Recominant Antibody Derivatives," *Journal of Chromatography B* 786:161-176, (2003).

Woof et al. "Human Antibody-Fc receptor interactions illuminated by crystal structures," *Nat. Rev. Immunol.* 4:1-11, (2004).

Wright et al. "ADAM28: a potential oncogene involved in asbestos-related lung adenocarcinomas," *Genes Chromosomes Cancer* 49(8);688-698, (Aug. 2010).

Wu et al. "Simultaneous Targeting of Multiple Disease Mediators by a Dual-Variable-Domain Immunoglobulin," *Nature Biotechnology* 25(11):1290-1297, (Nov. 2007).

Xie et al. "A New format of Bispecific Antibody: Highly efficient heterodimerization, expression and tumor cell lysis," *J. of Immunol. Methods* 296:95-101, (2005).

Yancopoulos, G.D. et al. "Vascular-Specific Growth Factors and Blood Vessel Formation," *Nature* 407:242-248, (Sep. 14, 2000).

Zeidler et al. "Simultaneous Activation of T Cells and Accessory Cells by a New Class of Intact Bispecific Antibody Results in Efficient Tumor Cell Killing," *Journal of Immunology* 163:1246-1252, (1999).

Ziolkowska et al. "High Levels of IL-17 in Rheumatoid Arthritis Patients: IL-15 Triggers In Vitro IL-17 Production via Cyclosporin A-Sensitive Mechanism," *J. Immunol.* 164:2832-2838, (2000).

Zuo et al. "An Efficient Route to the Production of an IgG-Like Bispecific Antibody," *Protein Engineering* 13(5):361-367, (2000).

Patentee's Submission of Jun. 11, 2012, for European Patent No. 1 957 533, filed on Oct. 23, 2006, Reply to Communication Pursuant to Article 94(3) EPC dated Dec. 2, 2011, 7 pages.

International Search Report dated Jul. 29, 2013, for PCT Patent Application No. PCT/EP2013/060529, filed on May 22, 2013, 7 pages.

International Search Report dated Dec. 6, 2011, for PCT Patent Application No. PCT/EP2011/064476 filed on Aug. 23, 2011, 7 pages.

International Search Report dated Dec. 6, 2011, for PCT Patent Application No. PCT/EP2011/064468 filed on Aug. 23, 2011, 7pages.

International Search Report dated Sep. 9, 2015, for PCT Application No. PCT/EP2015/057165, filed on Apr. 1, 2015, 5 pages.

International Search Report, dated Sep. 29, 2015 for PCT/EP2015/067369, filed on Jul. 29, 2015, 5 pages.

Written Opinion of the International Searching Authority dated Jul. 29, 2013, for PCT Patent Application No. PCT/EP2013/060529, filed on May 22, 2013, 7 pages.

Written Opinion of the International Searching Authority dated Dec. 6, 2011, for PCT Patent Application No. PCT/EP2011/064476 filed on Aug. 23, 2011, 4 pages.

Written Opinion of the International Searching Authority dated Dec. 6, 2011, for PCT Patent Application No. PCT/EP2011/064468 filed on Aug. 23, 2011, 4 pages.

Written Opinion dated Sep. 9, 2015, for PCT Application No. PCT/EP2015/057165, filed on Apr. 1, 2015, 7 pages.

Written Opinion of the International Searching Authority dated Sep. 29, 2015, for PCT Patent Application No. PCT/EP2015/067369 filed on Jul. 29, 2015, 4 pages.

Agata, Y. et al. "Expression of the PD-1 Antigen on the Surface of Stimulated Mouse T and B Lymphocytes," *Int. Immunology* 8(5):765-772, (1996).

Anthony, R.M. et al. "A Recombinant IgG Fc that Recapitulates the Anti-inflammatory Activity of IVIG," *Science*, 320(5874):373-376, (2008).

(56) References Cited

OTHER PUBLICATIONS

Armour, K.L. et al. "Recombinant Human IgG Molecules Lacking Fcγ Receptor I Binding and Monocyte Triggering Activities," *Eur. J. Immunol.* 29:2613-2624, (1999).
Bendig, M.M. "Humanization of Rodent Monoclonal Antibodies by CDR Grafting," *Methods: A companion to Methods in Enzymology* 8:83-93 (1995).
Boado, R.J. et al. "Engineering and Expression of a Chimeric Transferrin Receptor Monoclonal Antibody for Blood-Brain Barrier Delivery in the Mouse," *Biotechnology and Bioengineering* 102(4):1251-1258, (Mar. 1, 2009).
Boado, R.J. et al. "Selective Targeting of a TNFR Decoy Receptor Pharmaceutical to the Primate Brain as a Receptor-Specific IgG Fusion Protein," *J. of Biotechnology* 146(1-2):84-91, (Mar. 1, 2010).
Boado, R.J. et al. "Drug Targeting of Erythropoietin Across the Primate Blood-Brain Barrier With an IgG Molecular Trojan Horse," *J. Pharmacology and Experimental Therapeutics* 333(3):961-969, (Jun. 1, 2010).
Carter, P.J. "Potent antibody therapeutics by design," *Nature Reviews Immunology* 6:343-357, (May 2006).
Castoldi, R. et al. "TetraMabs: Simultaneous Targeting of Four Oncogenic Receptor Tyrosine Kinases for Tumor Growth Inhibition in Heterogeneous Tumor Cell Populations," *Protein Engineering, Design & Selection* 29(10):467-475, (2016, e-pub Aug. 29, 2016).
Chames P. et al. "Bispecific Antibodies for Cancer Therapy," *Current Opinion in Drug Discovery & Development*, 12(2):276-283,(2009).
Chan, A.C. et al. "Therapeutic Antibodies for Autoimmunity and Inflammation," *Nat. Rev. Immunol.*, 10(5):301-316, (May 2010).
Chen, L. et al. "Improved Variants of SrtA for Site-Specific Conjugation on Antibodies and Proteins With High Efficiency," *Scientific Reports* 6(31899):1-12, (Aug. 18, 2016).
Chin, J.W. et al. "Addition of p-azido-L-phenylalanine to the Genetic Code of *Escherichia coli*," *J. Am. Chem. Soc.*, 124(31):9026-9027, (2002).
Chin, J.W. et al. "In vivo Photocrosslinking With Unnatural Amino Acid Mutagenesis," *ChemBioChem*, 3(11):1135-1137, (2002).
Chin J.W., et al. "Addition of a Photocrosslinking Amino Acid to the Genetic Code of *Escherichia coli*," *Proc. Natl. Acad. Sci. U.S.A.*, 99(17):11020-11024, (2002).
Chinai, J.M. et al. "New Immunotherapies Targeting the PD-1 Pathway," *Trends in Pharmacological Sciences* 36(9):587-595, (Sep. 2015), 21 pages.
Clancy, K.W., et al. "Sortase Transpeptidases: Insights Into Mechanism, Substrate Specificity, and Inhibition," *Biopolymers*, 94(4):385-396, (2010).
Cruse, J.M., et al. 2nd ed., CRC Press p. 37, 316-317. (2003).
Daëron, M. "Fc Receptor Biology," *Annu. Rev. Immunol.* 15:203-234, (1997).
De Haas, M. et al. "Fcγ Receptors of Phagocytes," *J. Lab. Clin. Med.* 126(4):330-341, (Oct. 1995).
Friend, P.J. et al. "Phase I Study of an Engineered Aglycosylated Humanized CD3 Antibody in Renal Transplant Rejection," *Transplantation*, 68(11):1632-1637, (1999).
Hatfield, K.J. et al. "Antiangiogenic Therapy in Acute Myelogenous Leukemia: Targeting of Vascular Endothelial Growth Factor and Interleukin 8 as Possible Antileukemic Strategies," *Curr. Cancer Drug Targets*, 5(4):229-248, (2005).
Herberman, R.B. "Immunodiagnosis of Cancer," in Fleisher (ed.), "The Clinical Biochemistry of Cancer," p. 347 (American Association of Clinical Chemists (1979).
Huber, R. et al. "Crystallographic Structure Studies of an IgG Molecule and an Fc Fragment," *Nature*, 264:415-420, (1976).
Hudson, P.J. et al. "Engineered Antibodies," *Nat. Med.* 9:129-134, (2003).
Ilangovan, U. et al. "Structure of Sortase, The Transpeptidase That Anchors Proteins to the Cell Wall of *Staphylococcus aureus*," *Proc. Natl. Acad. Sci. U.S.A.* 98(11):6056-6061, (2001).

Ishida, Y. et al. "Induced Expression of PD-1, A Novel Member of the immunoglobulin Gene Superfamily, Upon Programmed Cell Death," *EMBO J.* 11(11):3887-3895, (1992).
Jiang, X.-R. et al. "Advances in the Assessment and Control of the Effector Functions of Therapeutic Antibodies," *Nat. Rev. Drug Discov.* 10(2):101-111, (2011).
Labrijn, A.F. et al. "Species-Specific Determinants in the IgG CH3 Domain Enable Fab-Arm Exchange by Affecting the Noncovalent CH3-CH3 Interaction Strength," *The Journal of Immunology* 187:3238-3246, (2011, e-pub. Aug. 12, 2011).
Lee, H.-S. et al. "Generation and Characterization of a Novel Single-Gene-Encoded Single-Chain Immunoglobulin Molecule With Antigen Binding Activity and Effector Functions" *Mol Immunol.* 36(1):61-71, (1999).
Levary, D.A. et al. "Protein-Protein Fusion Catalyzed by Sortase A," *PLOS One* 6:e18342.1-e18342.6, (2011).
Madej, M.P. et al. "Engineering of an Anti-Epidermal Growth Factor Receptor Antibody to Single Chain Format and Labeling by Sortase A-Mediated Protein Ligation," *Biotechnology and Bioengineering* 109(6):1461-1470, (2012).
Mallender, W.D. et al "Comparative Properties of the Single Chain Antibody and Fv Derivatives of mAb 4-4-20. Relationship Between Interdomain Interactions and the High Affinity for Fluorescein Ligand," *Journal of Biological Chemistry* 271(10):5338-5346, (Mar. 8, 1996).
Metz, S. et al. "Bispecific Digoxigenin-Binding Antibodies for Targeted Payload Delivery," *Proc. Natl. Acad. Sci. U.S.A.* 108 (20):8194-8199, (May 17, 2011).
Mizukami, Y. et al. "Induction of Interleukin-8 Preserves the Angiogenic Response in HIF-1α-Deficient Colon Cancer Cells," *Nat. Med.*, 11(9):992-997, (2005).
Möhlmann S. et al. "In vitro Sortagging of an Antibody Fab Fragment: Overcoming Unproductive Reactions of Sortase With Water and Lysine Side Chains," *Chembiochem: A European Journal of Chemical Biology*, 12(11):1774-1780, (2011).
Noren, C.J. et al. "A General Method for Site-Specific Incorporation of Unnatural Amino Acids into Proteins," *Science*, 244:182-188, (1989).
Novellino, L. et al. "A Listing of Human Tumor Antigens Recognized by T Cells: Mar. 2004 update," *Cancer Immunol. Immunother*, 54(3):187-207, (2005).
Pardridge, W.M. "Drug Transport Across the Blood-Brain Barrier," *J. of Cerebral Blood Flow & Metabolism* 32(11):1959-1972, (Aug. 29, 2012).
Parmiani, G. et al. "Unique human tumor antigens: immunobiology and use in clinical trials," *J. Immunol.* 178(4):1975-1979, (2007).
Paul W.E. "Structure and Function of Immunoglobulins," Chapter 9 in *Fundamental Immunology*, Third Edition, Raven Press, New York, New York, pp. 292-295, (1993).
Pluckthun, A. "Antibodies from *Escherichia coli*," Chapter 11 in *The Pharmacology of Monoclonal Antibodies: Handbook of Pharmacology*, Rosenberg and Moore, eds., Berlin:Springer-Verlag, vol. 113, pp. 269-315, (1994).
Popp M.W-L. et al. "Making and Breaking Peptide Bonds: Protein Engineering Using Sortase," *Angewandte Chemie*, 50(22):5024-5032, (2011).
Presta, L.G. "Molecular Engineering and Design of Therapeutic Antibodies," *Current Opinion in Immunology* 20:460-470, (2008).
Remington's *Pharmaceutical Sciences*, Table of Contents (1980).
Ren, Y. et al. "Macrophage Migration Inhibitory Factor Stimulates Angiogenic Factor Expression and Correlates With Differentiation and Lymph Node Status in Patients With Esophageal Squamous Cell Carcinoma," *Ann. Surg.* 242:55-63, (2005).
Robbie, G. J. et a l. (Dec. 2013). "A Novel Investigational Fc-Modified Humanized Monoclonal Antibody, Motavizumab-YTE, Has an Extended Half-Life in Healthy Adults," *Antimicrobial Agents and Chemotherapy* 57(12):6147-6153.
Rose, R.J. et al. "Quantitative Analysis of the Interaction Strength and Dynamics of Human IgG4 Half Molecules by Native Mass Spectrometry," *Structure* 19:1274-1282, (Sep. 7, 2011).
Routledge, E.G. et al. "The Effect of Aglycosylation on the Immunogenicity of a Humanized Therapeutic CD3 Monoclonal Antibody," *Transplantation*, 60(8):847-853, (1995).

(56) References Cited

OTHER PUBLICATIONS

Roux, K.H. et al. "Comparisons of the Ability of Human IgG3 Hinge Mutants, IgM, IgE, and IgA2, To Form Small Immune Complexes: A Role for Flexibility and Geometry," *J. Immunol.* 161(8):4083-4090, (1998).

Sakamoto, T. et al. "Enzyme-Mediated Site-Specific Antibody-Protein Modification Using a ZZ Domain as a Linker," *BioConjugate Chem.* 21:2227-2293 (2010, e-pub. Nov. 11, 2010).

Salfeld, J.G. "Isotype Selection in Antibody Engineering," *Nat. Biotechnol.* 25(12):1369-1372, (Dec. 2007).

Scheuer, W. et al."Anti-Tumoral, Anti-Angiogenic and Anti-Metastatic Efficacy of a Tetravalent Bispecific Antibody (TAvi6) Targeting VEGF-A and Angiopoietin-2," *MABS* 8(3):562-573, (2016).

Sensi, M. et al. "Unique Tumor Antigens: Evidence for Immune Control of Genome Integrity and Immunogenic Targets for T Cell-Mediated Patient-Specific Immunotherapy," *Clin. Cancer Res.*, 12(17):5023-5032, (2006).

Sondermann, P. et al. "The 3.2-A Crystal Structure of the Human IgG1 Fc Fragment-FcγRIII Complex," *Nature*, 406:267-273, (2000).

Strop, P. et al. "Generating Bispecific Human IgG1 and IgG2 Antibodies from Any Antibody Pair," *Journal of Molecular Biology*, 420(3):204-219, (2012).

Ta, H.T. et al. "Enzymatic Single-Chain Antibody Tagging a Universal Approach to Targeted Molecular Imaging and Cell Homing in Cardiovascular Disease," *Circulation Research*, 109(4):365-373, (2011).

Thies, M.J. et al. "Folding and Association of the Antibody Domain CH3: prolyl Isomerization Precedes Dimerization," *J. Mol. Biol.* 293:67-79, (1999).

Ton-That, H. et al. "Purification and Characterization of Sortase, The Transpeptidase That Cleaves Surface Proteins of *Staphylococcus aureus* at the LPXTG Motif," *Proc. Natl. Acad. Sci. U. S.A.* 96(22):12424-12429, (1999).

Tsukiji, S. et al. "Sortase-Mediated Ligation: A Gift from Gram-Positive Bacteria to Protein Engineering," *Chembiochem*, 10(5):787-798, (2009).

Wagner, K. et al."Bispecific Antibody Generated With Sortase and Click Chemistry Has Broad Anti-influenza Virus Activity," *Proc. Natl. Acad. Sci. USA* 111:16820-16825, (Nov. 25, 2014).

Wang, L. et al. "Expanding the Genetic Code," *Chem. Commun (Camb.)*, 7:1-11, (2002).

Wang. J. et al. (2016, e-pub. May 15, 2015). "Projected Human Pharmacokinetics of Monoclonal Antibodies From Nonclinical Data: Comparative Evaluation of Prediction Approaches in Early Drug Development," *Biopharm. Drug Dispos.* 37:51-65.

Ward, E.S. et al. "The Effector Functions of Immunoglobulins: Implications for Therapy," *Ther. Immunol.* 2:77-94, (1995).

Witte M.D. et al. "Preparation of Unnatural N-to-N and C-to-C Protein Fusions," *Proceedings of the National Academy of Sciences of the United States of America*, 109(30):11993-11998, (2012).

Yu, Y.J. et al."Developing Therapeutic Antibodies for Neurodegenerative Disease," *Neurotherapeutics* 10(3):459-472, (Apr. 3, 2013).

Declaration and Curriculum Vitae for Josh T. Pearson, dated Jan. 17, 2018, 13 pages.

International Preliminary Report on Patentability for PCT Application No. PCT/EP2014/079353, dated Jul. 12, 2016, filed Dec. 29, 2014, 9 pages.

International Search Report for PCT Application No. PCT/EP2014/079353, dated Apr. 20, 2015, filed Dec. 29, 2014, 6 pages.

International Search Report dated May 8, 2014, for PCT Patent Application No. PCT/EP2013/063258, filed on Jun. 25, 2013, 7 pages.

Written Opinion International for PCT Application No. PCT/EP2014/079353, dated Apr. 4, 2015, filed Dec. 29, 2014, 8 pages.

Written Opinion of the International Searching Authority dated May 8, 2014, for PCT Patent Application No. PCT/EP2013/063258, filed on Jun. 25, 2013, 7 pages.

Zhang, Z. et al. "Human Polyvalent Immunoglobulin for Treatment," *Foreign Medicine Blood, Transfusion and Hematology* 23(6):365, (Dec. 31, 2000). With English Translation.

\* cited by examiner

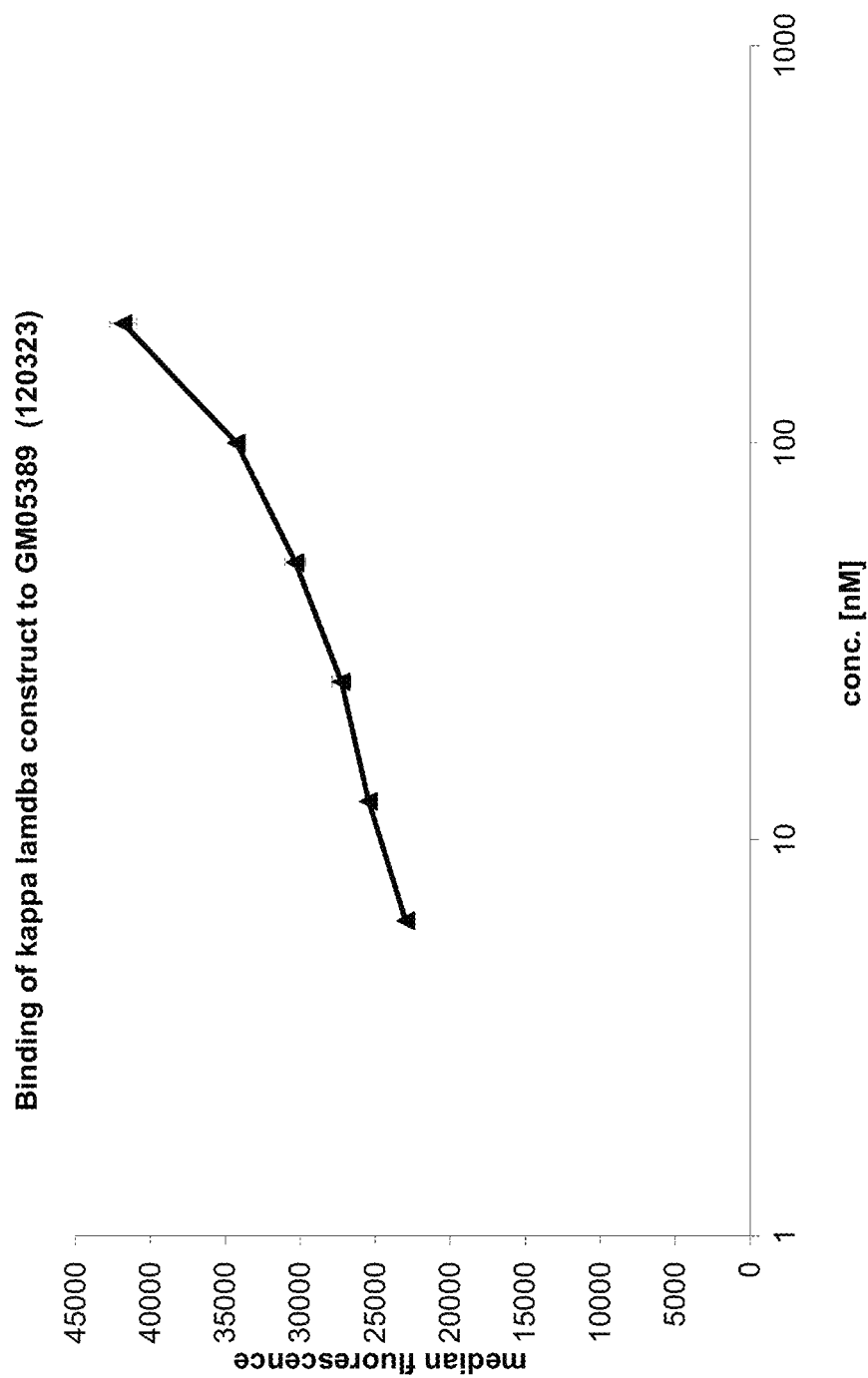

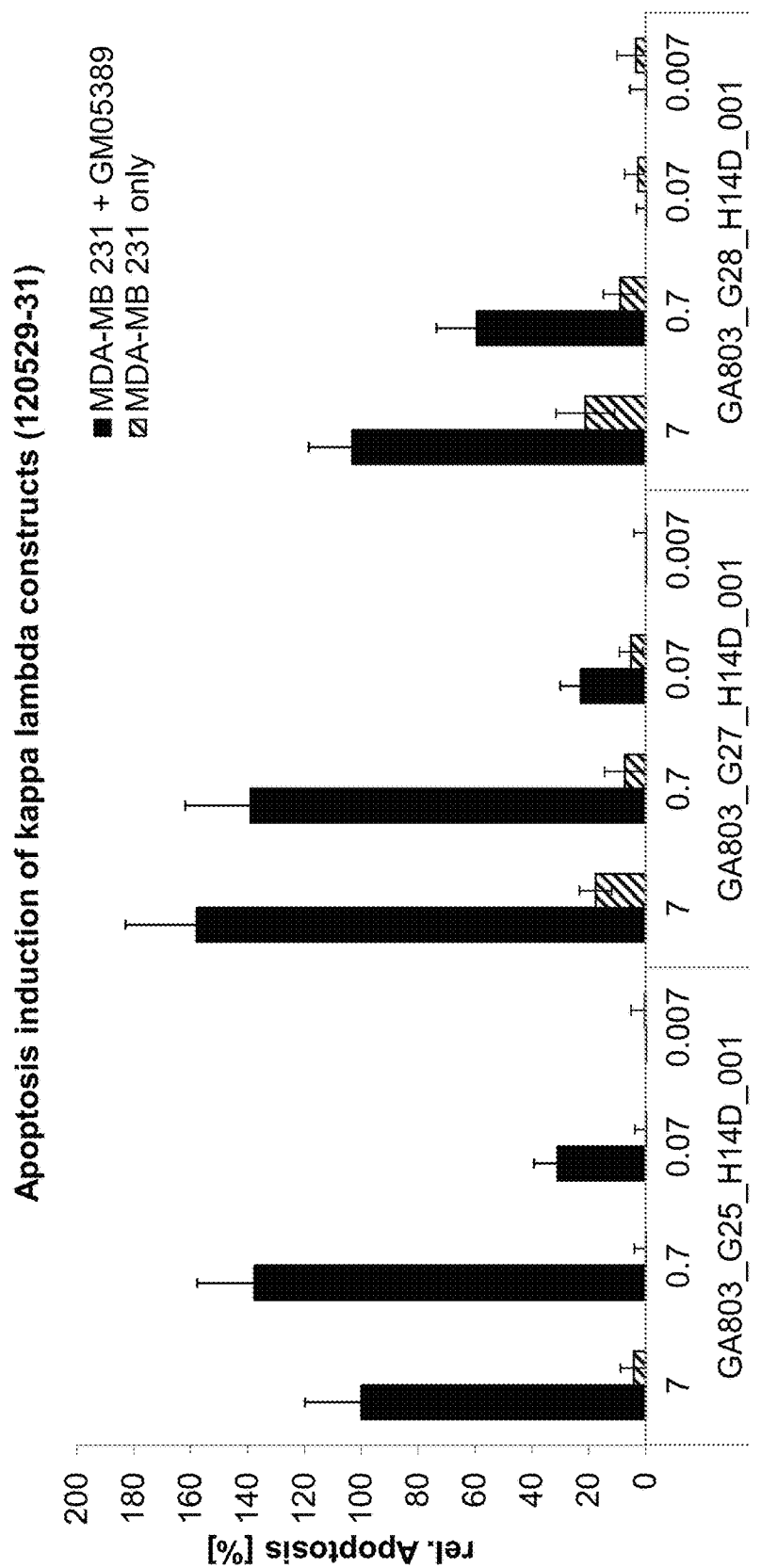

SEQUENCE LISTING

```
<160> NUMBER OF SEQ ID NOS: 12

<210> SEQ ID NO 1
<211> LENGTH: 1374
<212> TYPE: DNA
<213> ORGANISM: Artificial
<220> FEATURE:
<223> OTHER INFORMATION: nucleotide sequence of modified heavy chain
      CH3-CH2-CH1-VL, wherein VL is a variable domain of a common light
      chain (CLC-Fc cross-Mab)

<400> SEQUENCE: 1
atgggatgga gctgtatcat cctcttcttg gtagcaacag ctaccggtgt gcattccgac      60
atccagatga cccagagccc cagcagcctg agcgccagcg tgggcgacag agtgaccatc     120
acctgcagcg ccagccaggg catccggaac tacctgaact ggtatcagca gaagcccggc     180
aaggccccca agctgctgat ctactacacc agcagcctgc acagcggcgt gcctagccgg     240
tttagcggca gcggctccgg caccgacttc accctgacca ttagctccct gcagcccgag     300
gacttcgcca cctactactg ccagcagtac agcaagctgc cctggacctt cggccaggga     360
acaaaggtgg agatcaagag ctccgctagc accaagggcc catcggtctt cccccctggca    420 ccctcctcca agagcacctc tgggggcaca gcggccctgg gctgcctggt caaggactac     480
ttccccgaac cggtgacggt gtcgtggaac tcaggcgccc tgaccagcgg cgtgcacacc     540
ttcccggctg tcctacagtc ctcaggactc tactccctca gcagcgtggt gaccgtgccc     600
tccagcagct gggcaccca gacctacatc tgcaacgtga atcacaagcc cagcaacacc     660
aaggtggaca agaaagttga gcccaaatct tgtgacaaaa ctcacacatg cccaccgtgc     720
ccagcacctg aactcctggg gggaccgtca gtcttcctct tccccccaaa acccaaggac     780
accctcatga tctcccggac ccctgaggtc acatgcgtgg tggtggacgt gagccacgaa     840
gaccctgagg tcaagttcaa ctggtacgtg gacggcgtgg aggtgcataa tgccaagaca     900
aagccgcggg aggagcagta acagcacg taccgtgtgg tcagcgtcct caccgtcctg      960
caccaggact ggctgaatgg caaggagtac aagtgcaagg tctccaacaa agccctccca    1020
gcccccatcg agaaaaccat ctccaaagcc aaagggcagc ccgagaacc acaggtgtac    1080 accctgcccc catcccggga tgagctgacc aagaaccagg tcagcctgac ctgcctggtc   1140
aaaggcttct atcccagcga catcgccgtg gagtgggaga gcaatgggca gccggagaac   1200
aactacaaga ccacgcctcc cgtgctggac tccgacggct ccttcttcct ctacagcaag   1260
ctcaccgtgg acaagagcag gtggcagcag gggaacgtct tctcatgctc cgtgatgcat   1320
gaggctctgc acaaccacta cacgcagaag agcctctccc tgtctccggg taaa         1374

<210> SEQ ID NO 2
<211> LENGTH: 738
<212> TYPE: DNA
<213> ORGANISM: Artificial
<220> FEATURE:
<223> OTHER INFORMATION: nucleotide sequence of modified light chain
``` comprising a polypeptide consisting of Ckappa-VH1-Ckappa wherein
VH1 is the variable heavy chain domain from an antibody which
binds to a first antigen (anti-DR5 VH1 2A11-CL (kappa))

<400> SEQUENCE: 2

| | |
|---|---|
| atgggctgga gctgcatcat cctgttcctg gtggccaccg ccaccggcgt gcattccgag | 60 |
| gtgcagctgc tggagagcgg cggcggcctg gtgcagcccg gcggcagcct gaggctgagc | 120 |
| tgcgccgcca gcggcttcac cttcagcagc tacgccatga gctgggtgag gcaggccccc | 180 |
| ggcaagggcc tggagtgggt gagcgccatc agcggcagcg gcggcagcac ctactacgcc | 240 |
| gacagcgtga agggcaggtt caccatcagc agggacaaca gcaagaacac cctgtacctg | 300 |
| cagatgaaca gcctgagggc cgaggacacc gccgtgtact actgcgccag ggcccctac | 360 |
| ggcaggtacg ccgccctgga ctactggggc cagggcaccc tggtgaccgt gagcagcgct | 420 |
| agcgtggccg ctcccagcgt gttcatcttc ccacccagcg acgagcagct gaagtccggc | 480 |
| acagccagcg tggtgtgcct gctgaacaac ttctaccccc gcgaggccaa ggtgcagtgg | 540 |
| aaggtggaca acgccctgca gagcggcaac agccaggaat ccgtgaccga gcaggacagc | 600 |
| aaggactcca cctacagcct gagcagcacc ctgaccctga gcaaggccga ctacgagaag | 660 |
| cacaaggtgt acgcctgcga agtgacccac cagggcctgt ccagccccgt gaccaagagc | 720 |
| ttcaaccggg gcgagtgc | 738 |

<210> SEQ ID NO 3
<211> LENGTH: 744
<212> TYPE: DNA
<213> ORGANISM: Artificial
<220> FEATURE:
<223> OTHER INFORMATION: nucleotide sequence of modified light chain
comprising a polypeptide consisting of Ckappa-VH1-Ckappa wherein
VH1 is the variable heavy chain domain from an antibody which
binds to a first antigen (anti-DR5 VH1 8E11 -CL (kappa))

<400> SEQUENCE: 3

| | |
|---|---|
| atgggctgga gctgcatcat cctgttcctg gtggccaccg ccaccggcgt gcattccgag | 60 |
| gtgcaattgt tggagtctgg gggaggcttg gtacagcctg gggggtccct gagactctcc | 120 |
| tgtgcagcct ccggattcac ctttagcagt tatgccatga gctgggtccg ccaggctcca | 180 |
| gggaaggggc tggagtgggt ctcagctatt agtggtagtg gtggtagcac atactacgca | 240 |
| gactccgtga agggccggtt caccatctcc agagacaatt ccaagaacac gctgtatctg | 300 |
| cagatgaaca gcctgagagc cgaggacacg gccgtatatt actgtgcgaa agactcttct | 360 |
| tcttggtact cctacgcttt cgactactgg ggccaaggaa ccctggtcac cgtctcgagt | 420 |
| gctagcgtgg ccgctcccag cgtgttcatc ttcccaccca gcgacgagca gctgaagtcc | 480 |
| ggcacagcca gcgtggtgtg cctgctgaac aacttctacc ccgcgaggc caaggtgcag | 540 |
| tggaaggtgg acaacgccct gcagagcggc aacagccagg aatccgtgac cgagcaggac | 600 |
| agcaaggact ccacctacag cctgagcagc accctgaccc tgagcaaggc cgactacgag | 660 |
| aagcacaagg tgtacgcctg cgaagtgacc caccagggcc tgtccagccc cgtgaccaag | 720 |
| agcttcaacc ggggcgagtg ctga | 744 |

<210> SEQ ID NO 4
<211> LENGTH: 729
<212> TYPE: DNA
<213> ORGANISM: Artificial
<220> FEATURE:
<223> OTHER INFORMATION: nucleotide sequence of modified light chain
comprising a polypeptide consisting of Ckappa-VH1-Ckappa wherein VH1 is the variable heavy chain domain from an antibody which
binds to a first antigen (anti-DR5 VH1 21C11 -CL (kappa))

<400> SEQUENCE: 4

| | | | | |
|---|---|---|---|---|
| atgggctgga | gctgcatcat | cctgttcctg | gtggccaccg | ccaccggcgt gcattcccag | 60 |
| gtgcaattgg | tgcagtctgg | ggctgaggtg | aagaagcctg | gtcctcggt gaaggtctcc | 120 |
| tgcaaggcct | ccggaggcac | attcagcagc | tacgctataa | gctgggtgcg acaggcccct | 180 |
| ggacaagggc | tcgagtggat | gggaaggatc | atccctatct | ttggtacagc aaactacgca | 240 |
| cagaagttcc | agggcagggt | caccattact | gcagacaaat | ccacgagcac agcctacatg | 300 |
| gagctgagca | gcctgagatc | tgaggacacc | gccgtgtatt | actgtgcgag agaaggtttc | 360 |
| tacatcgact | actggggcca | agggaccacc | gtgaccgtct | cctcagctag cgtggccgct | 420 |
| cccagcgtgt | tcatcttccc | cccagcgac | gagcagctga | agtccggcac agccagcgtg | 480 |
| gtgtgcctgc | tgaacaactt | ctaccccgc | gaggccaagg | tgcagtggaa ggtggacaac | 540 |
| gccctgcaga | gcggcaacag | ccaggaatcc | gtgaccgagc | aggacagcaa ggactccacc | 600 |
| tacagcctga | gcagcaccct | gaccctgagc | aaggccgact | acgagaagca aggtgtac | 660 |
| gcctgcgaag | tgacccacca | gggcctgtcc | agcccgtga | ccaagagctt caaccggggc | 720 |
| gagtgctga | | | | | 729 |

<210> SEQ ID NO 5
<211> LENGTH: 735
<212> TYPE: DNA
<213> ORGANISM: Artificial
<220> FEATURE:
<223> OTHER INFORMATION: nucleotide sequence of modified light chain
VH2-Clambda wherein VH2 is the variable heavy chain domain from an
antibody which binds to a second antigen (anti-FAP VH2 3C6 -CL
(lambda))

<400> SEQUENCE: 5

| | | | | |
|---|---|---|---|---|
| atgggatgga | gctgtatcat | cctcttcttg | gtagcaacag | ctaccggtgt gcattccgag | 60 |
| gtgcagctgc | tggagagcgg | cggcggcctg | gtgcagcccg | gcggcagcct gaggctgagc | 120 |
| tgcgccgcca | gcggcttcac | cttcagcagc | tacgccatga | gctgggtgag gcaggccccc | 180 |
| ggcaagggcc | tggagtgggt | gagcgccatc | agcggcagcg | gcggcagcac ctactacgcc | 240 |
| gacagcgtga | agggcaggtt | caccatcagc | agggacaaca | gcaagaacac cctgtacctg | 300 |
| cagatgaaca | gcctgagggc | cgaggacacc | gccgtgtact | actgcgccaa gagcgtggtg | 360 |
| tacagctacg | accccggctt | cgactactgg | ggccagggca | ccctggtgac cgtgtccgga | 420 |
| cagcccaagg | ccgcccccag | cgtgaccctg | ttcccccca | gcagcgagga gctgcaggcc | 480 |
| aacaaggcca | ccctggtgtg | cctgatcagc | gacttctacc | cgggcgccgt gaccgtggcc | 540 |
| tggaaggccg | acagcagccc | cgtgaaggcc | ggcgtggaga | ccaccacccc cagcaagcag | 600 |
| agcaacaaca | agtacgccgc | cagcagctac | ctgagcctga | ccccgagca gtggaagagc | 660 |
| cacaggagct | acagctgcca | ggtgacccac | gagggcagca | ccgtggagaa gaccgtggcc | 720 |
| cccaccgagt | gcagc | | | | 735 |

<210> SEQ ID NO 6
<211> LENGTH: 458
<212> TYPE: PRT
<213> ORGANISM: Artificial
<220> FEATURE:
<223> OTHER INFORMATION: amino acid sequence of modified heavy chain
CH3-CH2-CH1-VL, wherein VL is a variable domain of a common light
chain (CLC-Fc cross-Mab)

```
<400> SEQUENCE: 6

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Ser Ala Ser Gln Gly Ile
        35                  40                  45

Arg Asn Tyr Leu Asn Trp Tyr Gln Gln Lys Pro Gly Lys Ala Pro Lys
    50                  55                  60

Leu Leu Ile Tyr Tyr Thr Ser Leu His Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Tyr Ser Lys
            100                 105                 110

Leu Pro Trp Thr Phe Gly Gln Gly Thr Lys Val Glu Ile Lys Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Val Glu Pro Lys Ser Cys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Asp Glu
        355                 360                 365

Leu Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
```

```
                    405                 410                 415
Leu Tyr Ser Lys Leu Thr Val Asp Lys Ser Arg Trp Gln Gln Gly Asn
                420                 425                 430

Val Phe Ser Cys Ser Val Met His Glu Ala Leu His Asn His Tyr Thr
            435                 440                 445

Gln Lys Ser Leu Ser Leu Ser Pro Gly Lys
        450                 455

<210> SEQ ID NO 7
<211> LENGTH: 246
<212> TYPE: PRT
<213> ORGANISM: Artificial
<220> FEATURE:
<223> OTHER INFORMATION: amino acid sequence of modified light chain
      comprising a polypeptide consisting of Ckappa-VH1-Ckappa wherein
      VH1 is the variable heavy chain domain from an antibody which
      binds to a first antigen (anti-DR5 VH1 2A11-CL (kappa))

<400> SEQUENCE: 7

Met Gly Trp Ser Cys Ile Ile Leu Phe Leu Val Ala Thr Ala Thr Gly
1               5                   10                  15

Val His Ser Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Ala Met Ser Trp Val Arg Gln Ala Pro Gly Lys Gly Leu
    50                  55                  60

Glu Trp Val Ser Ala Ile Ser Gly Ser Gly Gly Ser Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Gly Pro Tyr Gly Arg Tyr Ala Ala Leu Asp Tyr
        115                 120                 125

Trp Gly Gln Gly Thr Leu Val Thr Val Ser Ser Ala Ser Val Ala Ala
    130                 135                 140

Pro Ser Val Phe Ile Phe Pro Pro Ser Asp Glu Gln Leu Lys Ser Gly
145                 150                 155                 160

Thr Ala Ser Val Val Cys Leu Leu Asn Asn Phe Tyr Pro Arg Glu Ala
                165                 170                 175

Lys Val Gln Trp Lys Val Asp Asn Ala Leu Gln Ser Gly Asn Ser Gln
            180                 185                 190

Glu Ser Val Thr Glu Gln Asp Ser Lys Asp Ser Thr Tyr Ser Leu Ser
        195                 200                 205

Ser Thr Leu Thr Leu Ser Lys Ala Asp Tyr Glu Lys His Lys Val Tyr
    210                 215                 220

Ala Cys Glu Val Thr His Gln Gly Leu Ser Ser Pro Val Thr Lys Ser
225                 230                 235                 240

Phe Asn Arg Gly Glu Cys
                245

<210> SEQ ID NO 8
<211> LENGTH: 247
<212> TYPE: PRT
<213> ORGANISM: Artificial
<220> FEATURE:
<223> OTHER INFORMATION: amino acid sequence of modified light chain
``` comprising a polypeptide consisting of Ckappa-VH1-Ckappa wherein
VH1 is the variable heavy chain domain from an antibody which
binds to a first antigen (anti-DR5 VH1 8E11 -CL (kappa))

<400> SEQUENCE: 8

Met Gly Trp Ser Cys Ile Ile Leu Phe Leu Val Ala Thr Ala Thr Gly
1               5                   10                  15

Val His Ser Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Ala Met Ser Trp Val Arg Gln Ala Pro Gly Lys Gly Leu
    50                  55                  60

Glu Trp Val Ser Ala Ile Ser Gly Ser Gly Gly Ser Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Asp Ser Ser Trp Tyr Ser Tyr Ala Phe Asp
        115                 120                 125

Tyr Trp Gly Gln Gly Thr Leu Val Thr Val Ser Ser Ala Ser Val Ala
    130                 135                 140

Ala Pro Ser Val Phe Ile Phe Pro Pro Ser Asp Glu Gln Leu Lys Ser
145                 150                 155                 160

Gly Thr Ala Ser Val Val Cys Leu Leu Asn Asn Phe Tyr Pro Arg Glu
                165                 170                 175

Ala Lys Val Gln Trp Lys Val Asp Asn Ala Leu Gln Ser Gly Asn Ser
            180                 185                 190

Gln Glu Ser Val Thr Glu Gln Asp Ser Lys Asp Ser Thr Tyr Ser Leu
        195                 200                 205

Ser Ser Thr Leu Thr Leu Ser Lys Ala Asp Tyr Glu Lys His Lys Val
    210                 215                 220

Tyr Ala Cys Glu Val Thr His Gln Gly Leu Ser Ser Pro Val Thr Lys
225                 230                 235                 240

Ser Phe Asn Arg Gly Glu Cys
                245

<210> SEQ ID NO 9
<211> LENGTH: 242
<212> TYPE: PRT
<213> ORGANISM: Artificial
<220> FEATURE:
<223> OTHER INFORMATION: amino acid sequence of modified light chain
comprising a polypeptide consisting of Ckappa-VH1-Ckappa wherein
VH1 is the variable heavy chain domain from an antibody which
binds to a first antigen (anti-DR5 VH1 21C11 -CL (kappa))

<400> SEQUENCE: 9

Met Gly Trp Ser Cys Ile Ile Leu Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ser Ser Val Lys Val Ser Cys Lys Ala Ser Gly Gly Thr Phe
        35                  40                  45

Ser Ser Tyr Ala Ile Ser Trp Val Arg Gln Ala Pro Gly Gln Gly Leu
    50                  55                  60

```
Glu Trp Met Gly Arg Ile Ile Pro Ile Phe Gly Thr Ala Asn Tyr Ala
65                  70                  75                  80

Gln Lys Phe Gln Gly Arg Val Thr Ile Thr Ala Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Glu Gly Phe Tyr Ile Asp Tyr Trp Gly Gln Gly
        115                 120                 125

Thr Thr Val Thr Val Ser Ser Ala Ser Val Ala Ala Pro Ser Val Phe
    130                 135                 140

Ile Phe Pro Pro Ser Asp Glu Gln Leu Lys Ser Gly Thr Ala Ser Val
145                 150                 155                 160

Val Cys Leu Leu Asn Asn Phe Tyr Pro Arg Glu Ala Lys Val Gln Trp
                165                 170                 175

Lys Val Asp Asn Ala Leu Gln Ser Gly Asn Ser Gln Glu Ser Val Thr
            180                 185                 190

Glu Gln Asp Ser Lys Asp Ser Thr Tyr Ser Leu Ser Ser Thr Leu Thr
        195                 200                 205

Leu Ser Lys Ala Asp Tyr Glu Lys His Lys Val Tyr Ala Cys Glu Val
    210                 215                 220

Thr His Gln Gly Leu Ser Ser Pro Val Thr Lys Ser Phe Asn Arg Gly
225                 230                 235                 240

Glu Cys

<210> SEQ ID NO 10
<211> LENGTH: 245
<212> TYPE: PRT
<213> ORGANISM: Artificial
<220> FEATURE:
<223> OTHER INFORMATION: amino acid sequence of modified light chain
      VH2-Clambda wherein VH2 is the variable heavy chain domain from an
      antibody which binds to a second antigen (anti-FAP VH2 3C6 -CL
      (lambda))

<400> SEQUENCE: 10

Met Gly Trp Ser Cys Ile Ile Leu Phe Leu Val Ala Thr Ala Thr Gly
1               5                   10                  15

Val His Ser Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Ala Met Ser Trp Val Arg Gln Ala Pro Gly Lys Gly Leu
    50                  55                  60

Glu Trp Val Ser Ala Ile Ser Gly Ser Gly Gly Ser Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Ser Val Val Tyr Ser Tyr Asp Pro Gly Phe Asp
        115                 120                 125

Tyr Trp Gly Gln Gly Thr Leu Val Thr Val Ser Gly Gln Pro Lys Ala
    130                 135                 140

Ala Pro Ser Val Thr Leu Phe Pro Pro Ser Ser Glu Glu Leu Gln Ala
145                 150                 155                 160

Asn Lys Ala Thr Leu Val Cys Leu Ile Ser Asp Phe Tyr Pro Gly Ala
```

```
                165                 170                 175
Val Thr Val Ala Trp Lys Ala Asp Ser Ser Pro Val Lys Ala Gly Val
            180                 185                 190

Glu Thr Thr Thr Pro Ser Lys Gln Ser Asn Asn Lys Tyr Ala Ala Ser
            195                 200                 205

Ser Tyr Leu Ser Leu Thr Pro Glu Gln Trp Lys Ser His Arg Ser Tyr
    210                 215                 220

Ser Cys Gln Val Thr His Glu Gly Ser Thr Val Glu Lys Thr Val Ala
225                 230                 235                 240

Pro Thr Glu Cys Ser
                245

<210> SEQ ID NO 11
<211> LENGTH: 14
<212> TYPE: PRT
<213> ORGANISM: Artificial Sequence
<220> FEATURE:
<223> OTHER INFORMATION: Synthetic Construct

<400> SEQUENCE: 11

Phe Asp Tyr Trp Gly Gln Gly Thr Leu Val Thr Val Ser Ser
1               5                   10

<210> SEQ ID NO 12
<211> LENGTH: 14
<212> TYPE: PRT
<213> ORGANISM: Artificial Sequence
<220> FEATURE:
<223> OTHER INFORMATION: Synthetic Construct

<400> SEQUENCE: 12

Met Asp Ala Trp Gly Gln Gly Thr Thr Val Thr Val Ser Ser
1               5                   10
```

MULTISPECIFIC DOMAIN EXCHANGED COMMON VARIABLE LIGHT CHAIN ANTIBODIES

CROSS REFERENCE TO RELATED APPLICATIONS

This application is a continuation of International Application No. PCT/EP2014/071531 having an international filind date of Oct. 8, 2014, the entire contents of which are incorporated herein by reference, and which claims benefit under 35 U.S.C. § 119 to European Patent Application No. 13188283.9 filed Oct. 11, 2013.

SEQUENCE LISTING

The instant application contains a Sequence Listing submitted via EFS-Web and hereby is incorporated by reference in its entirety. Said ASCII copy, created on Apr. 16, 2018, is named 146392037500SUBSEQLIST, and is 22,016 bytes in size.

The present invention relates to modified multispecific antibodies based on a common variable light chain domain (VL) and two different variable heavy chain domains ($VH_1$ and $VH_2$), their manufacture and use.

BACKGROUND OF THE INVENTION

Engineered proteins, such as bi- or multispecific antibodies capable of binding two or more antigens are known in the art. Such multispecific binding proteins can be generated using cell fusion, chemical conjugation, or recombinant DNA techniques.

A wide variety of recombinant multispecific antibody formats have been developed in the recent past, e.g. tetravalent bispecific antibodies by fusion of, e.g. an IgG antibody format and single chain domains (see e.g. Coloma, M. J., et al., Nature Biotech. 15 (1997) 159-163; WO 2001/077342; and Morrison, S. L., Nature Biotech. 25 (2007) 1233-1234).

In one approach, bispecific antibodies that are very similar to natural antibodies have been produced using the quadroma technology (see Milstein, C. and Cuello, A. C., Nature 305 (1983) 537-540) based on the somatic fusion of two different hybridoma cell lines expressing murine monoclonal antibodies with the desired specificities of the bispecific antibody. Because of the random pairing of two different antibody heavy and light chains within the resulting hybrid-hybridoma (or quadroma) cell line, up to ten different antibody species are generated of which only one is the desired, functional bispecific antibody. Due to the presence of mispaired byproducts, and significantly reduced production yields, means for sophisticated purification procedures are required (see e.g. Morrison, S. L., Nature Biotech. 25 (2007) 1233-1234). In general the same problem of mispaired byproducts remains if recombinant expression techniques are used.

In WO 98/50431 common light chains are used in multispecific antibodies to prevent mispairing of light and heavy chains, however the approach according to WO 98/50431 uses different heavy chains which are heterodimerized via the so-called 'knobs-into-holes' technology (Ridgway, J. B., Protein Eng. 9 (1996) 617-621; and WO 96/027011). In WO 98/50431 high yields of antibodies with heterodimerized ('knob-hole') heavy chains was observed. However, some homodimer formation ('hole-hole' or 'knob-knob') was also observed. The percentage of heterodimerized heavy chains could be further increased by remodeling the interaction surfaces of the two CH3 domains using a phage display approach and introducing a disulfide bridge between both CH3 domains in order to stabilize the heterodimers (Merchant A. M, et al., Nature Biotech 16 (1998) 677-681; Atwell, S., et al., J. Mol. Biol. 270 (1997) 26-35). New approaches using the principle of the knobs-into-holes technology are described e.g. in EP 1870459A1. One important constraint of this strategy is that the light chains of the two parent antibodies have to be 100% identical to prevent mispairing and formation of inactive molecules. The development of common light chains fitting to denovo generated antibodies is still challenging. Thus, this technique is not appropriate for easily developing recombinant, bispecific antibodies against two antigens starting from two different antibodies against the first and the second antigen, as either the heavy chains of these antibodies and/or the identical light chains have to be optimized.

WO 2012/023053 relates to bispecific antibodies using a common heavy chain. This approach is even more restricted instead of being generally applicable given the difficulties for generating common chains in general, and specifically as the binding properties for the bispecific antibodies have to be conferred only via the two different light chains directed against the first and second antigen without any contribution of the heavy chain. This is s clear constraint in view of the fact that in the majority of antibodies the heavy chain hypervariable regions, especially e.g. the complementarity determining region 3 of the heavy chain (CDR3-H), are attributed to be important for the binding properties of antibodies to their target antigen.

WO 2009/080252 relates to bivalent, bispecific antibodies, wherein in only one of the two antibody arms, the heavy chain variable domain (VH) and the light chain variable domain (VL) are exchanged in order to prevent light chain mispairing by generating light chains built up of different domains.

SUMMARY OF THE INVENTION

The present invention relates to modified multispecific antibodies based on a common variable light chain domain (VL) and two different variable heavy chain domains (herein referred to as $VH_1$ for the variable heavy chain domain of a first binding specificity and $VH_2$ for the variable heavy chain domain of a second binding specificity, respectively), their manufacture and their use.

The invention provides a multispecific antibody, wherein the antibody comprises
a) two modified heavy chains, wherein each heavy chain comprises in C-terminal to N-terminal direction heavy chain constant domains 3 to 1 (CH3, CH2 and CH1, in this order) and a light chain variable domain (VL), wherein the light chain variable domain (VL) is the variable domain of a common light chain;
b) one, in one embodiment exactly one, modified light chain, wherein the modified light chain comprises in C-terminal to N-terminal direction a constant light chain domain (CL) of kappa isotype (herein referred to as "CLic") and a variable heavy chain domain ($VH_1$) derived from an antibody, which specifically binds to a first antigen; and
c) one, in one embodiment exactly one, modified light chain, wherein the modified light chain comprises in C-terminal to N-terminal direction a constant light chain domain of lambda isotype (herein referred to as "CLX") and a variable heavy chain domain ($VH_2$) derived from an antibody, which specifically binds to a second antigen.

Within the antibody according to the present invention, the variable domains VH1 and VL form a first antigen binding site, which specifically binds to a first antigen, and the variable domains VH2 and VL form a second antigen binding site which binds to a second antigen.

In one embodiment of the invention, the multispecific antibody is a bivalent, bispecific antibody.

In one embodiment of the invention, the multispecific antibody is of IgG isotype. In one embodiment of the invention, the multispecific antibody is of IgG1 or IgG4 subclass. In one embodiment of the invention, the multispecific antibody is of IgG1 subclass.

One aspect of the invention is a nucleic acid encoding a multispecific antibody according to the invention. Another aspect of the invention is an expression vector containing said nucleic acid, wherein the expression vector is capable of expressing said nucleic acid in a prokaryotic or eukaryotic host cell. Yet another aspect of the invention is a prokaryotic or eukaryotic host cell comprising said expression vector.

One aspect of the invention is a method for the preparation of a multispecific antibody according to the invention, comprising the steps of
a) transforming a host cell with expression vectors comprising nucleic acid molecules encoding a multispecific antibody according to the invention;
b) culturing said host cell under conditions that allow synthesis of said multispecific antibody molecule; and
c) recovering said multispecific antibody molecule from said culture.

One aspect of the invention is a pharmaceutical composition comprising the multispecific antibody according to the invention and at least one pharmaceutically acceptable excipient.

One aspect of the invention is the multispecific antibody for use as a medicament.

One aspect of the invention is the multispecific antibody according to the invention for use in the treatment of cancer.

One aspect of the invention is the use of a multispecific antibody according to the invention for the manufacture of a medicament.

One embodiment of the invention is the use of a multispecific antibody according the invention for the manufacture of a medicament for the treatment of cancer.

One aspect of the invention is a method for the treatment of a patient in need of therapy, characterized by administering to the patient a therapeutically effective amount of a multispecific antibody according the invention.

One aspect of the invention is a method for the generation of a multispecific antibody based on a first antibody, which specifically binds to a first antigen, and a second antibody, which specifically binds to a second antigen, wherein the first antibody and the second antibody comprise a common light chain, comprising the steps of
a) modifying the light chain derived from said first antibody in order to obtain a light chain comprising in C-terminal to N-terminal direction a constant light chain domain of kappa isotype (CLI) and a heavy chain variable domain (VH$_1$) by replacing the light chain variable domain (VL) by the heavy chain variable domain (VH$_1$) of the heavy chain derived from said first antibody and, optionally, replacing the original constant light chain domain by a constant light chain domain of kappa isotype; and
b) modifying the light chain derived from said second antibody in order to obtain a light chain comprising in C-terminal to N-terminal direction a constant light chain domain of lambda isotype (CLλ) and a heavy chain variable domain (VH$_2$) by replacing the light chain variable domain (VL) by the heavy chain variable domain (VH$_2$) of the heavy chain derived from said second antibody and, optionally, replacing the original constant light chain domain by a constant light chain domain of lambda isotype;
and either one or both of the steps of c) and d):
c) modifying the heavy chain derived from said first antibody in order to obtain a heavy chain comprising in C-terminal to N-terminal direction heavy chain constant domains 3 to 1 (CH3, CH2 and CH1, in this order) and a light chain variable domain (VL) by replacing the heavy chain variable domain (VH$_1$) by the light chain variable domain (VL) of the light chain derived from said first antibody;
d) modifying the heavy chain derived from said second antibody in order to obtain a heavy chain comprising in C-terminal to N-terminal direction heavy chain constant domains 3 to 1 (CH3, CH2 and CH1, in this order) and a light chain variable domain (VL) by replacing the heavy chain variable domain (VH$_2$) by the light chain variable domain (VL) of the light chain derived from said second antibody.

In one embodiment said method further comprises the steps of
transforming a host cell with expression vectors comprising nucleic acid molecules encoding the multispecific antibody according to the invention,
culturing the host cell under conditions that allow synthesis of said multispecific antibody molecule; and
recovering said multispecific antibody molecule from said culture.

One aspect of the invention is a multispecific antibody obtained by said method.

The multispecific antibodies according to the present invention can be easily derived from two antibodies with different heavy chain variable domains (specifically binding to a first and a second antigen, respectively) which pair with a common light chain, respectively. With the multispecific antibodies of the invention, an engineering of the heavy chains, e.g. by the knobs-into-holes technology or similar heterodimerization approaches, is not necessary to ensure binding of the the heterodimers. The antibodies of the present invention possess an IgG-like structure and exhibit very good antigen binding properties. In addition, said antibodies exhibit a high variability with respect to antigen binding, because within the antibodies of the invention the antigen binding is mainly conferred via its variable heavy chain domains. This provides for a broad spectrum of possible epitopes bound by an antigen binding site, as the highest variability of a all antigen binding regions (CDRs) within an antibody is related to the CDR3 of the heavy chain variable domain. As a result, CDR3 of the heavy chain is often mainly responsible for specific antigen or epitope binding. In summary, this means that in most antibodies amino acid modifications within the CDR3 of the heavy chain variable domain are by far less tolerable with respect to the antigen binding properties of the antibody than amino acid modifications in all other CDRs.

In addition, the antibodies of the present invention are producible in good yield and can be easily separated from its side products, like unwanted homodimers, due two the different constant light chain domains (kappa and lambda) by using kappa and lambda specific purification steps.

BRIEF DESCRIPTION OF THE FIGURES

FIG. 8 Results from cell surface binding studies. Binding of the bispecific antibody according to the invention, which specifically binds to DR5 and FAP, to its antigen FAP was assessed in cell binding studies using the FAP expressing fibroblast cell line GM05389 by subsequent FACS analysis. Depicted is the result of the binding studies using the <FAP(3C6)[CLλ]-DR5(2A11)[CLκ]> bispecific antibody (specimen identifier GA803_G25_H14D_001) The constructs bind to GM05389 cells in a concentration dependent manner.

FIG. 9 Mediation of apoptosis in DR5 expressing MDA-MB 231 tumor cells by three bispecific antibodies according to the invention, which specifically bind to DR5 and FAP and include different DR5 binding sites derived from either one of the anti-DR5 antibody clones 2A11, 8E11 and 21C11 (specimen identifiers GA803_G25_H14D_001, GA803_G27_H14D_001, GA803_G28_H14D_00, respectively) was assessed using MDA-MB 231 cells either in the absence or in presence of FAP expressing fibroblasts (cell line GM05389). All constructs are capable of mediating apoptosis in MDA-MB 231 cells in the presence of FAP.

DETAILED DESCRIPTION OF THE INVENTION

1. Definitions

The terms "a", "an" and "the" generally include plural referents, unless the context clearly indicates otherwise.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence exchanges. In some embodiments, the number of amino acid exchanges are 10 or less, 9 or less, 8 or less, 7 or less, 6 or less, 5 or less, 4 or less, 3 or less, or 2 or less. In some embodiments, the VL acceptor human framework is 100% identical in its amino acid sequence to the VL human immunoglobulin framework amino acid sequence or the human consensus framework amino acid sequence.

Figure 1:
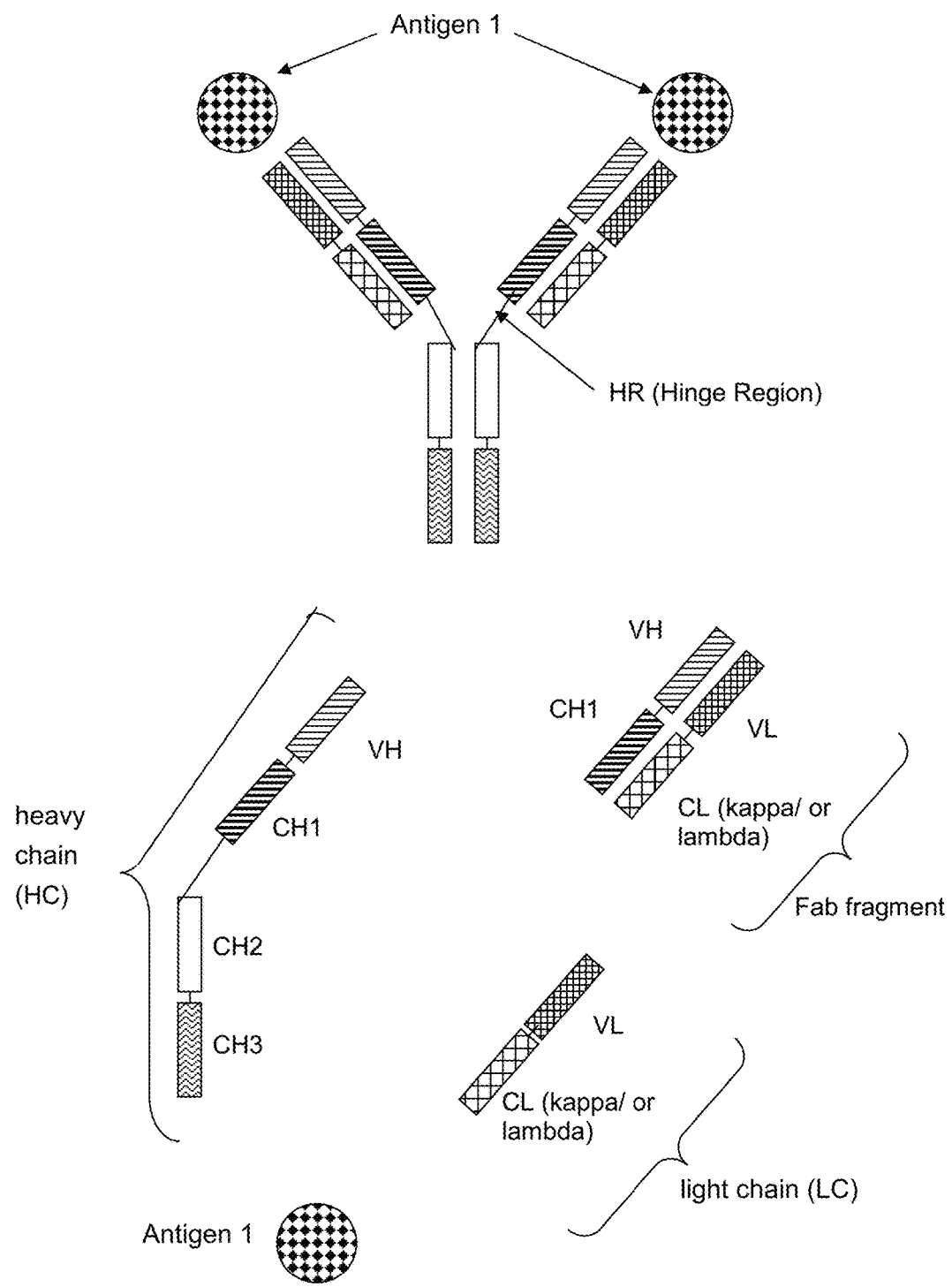
FIG. 1 A schematic illustration of a full length IgG-like antibody specific for one antigen with two pairs of heavy chains (HC) and light chains (LC), which respectively comprise variable and constant domains in a typical order.

The term "antibody" as used herein denotes a full length antibody consisting of two antibody heavy chains and two antibody light chains (see FIG. 1).

A heavy chain of a full length antibody is a polypeptide comprising in N-terminal to C-terminal direction an antibody heavy chain variable domain (VH), an antibody constant heavy chain domain 1 (CH1), an antibody heavy chain constant domain 2 (CH2), and an antibody heavy chain constant domain 3 (CH3), which is herein also abbreviated as "VH-CH1-CH2-CH3"; and optionally an antibody heavy chain constant domain 4 (CH4) in case of an antibody of the subclass IgE. In one embodiment, such an antibody comprises a hinge region (located between the CH1 and CH2 domains).

The light chain of a full length antibody is a polypeptide comprising in N-terminal to C-terminal direction an antibody light chain variable domain (VL), and an antibody light chain constant domain (CL), which is herein also abbreviated as "VL-CL". The antibody light chain constant domain (CL) can be of κ (kappa) or λ (lambda) isotype.

The light chains and heavy chains of an antibody are linked together via inter-polypeptide disulfide bonds formed between the CL domain of the light chain and the CH1 domain of the heavy chain and between the hinge regions of the two heavy chains of the full length antibody.

Examples of typical full length antibodies are natural antibodies like IgG (of subclasses IgG1, IgG2, IgG3 and IgG4), IgM, IgA, IgD, and IgE.

The antibodies according to the invention can be from a single species e.g. human, or they can be chimerized or humanized antibodies.

Wild type full length antibodies comprise two antigen binding sites, each one of which is formed by a pair of VH and VL domains, wherein both antigen binding sites specifically bind to the same (e.g. a first) antigen (see FIG. 1). The full length antibodies according to the invention comprise two antigen binding sites, each one of which formed by a pair of VH and VL domains, wherein one of the binding sites (i.e. the binding site formed by the pair of the VL domain of the common light chain and the VH domain of the heavy chain derived from the first antibody [$VH_1$]) specifically binds to at least one (e.g. a first) antigen; and wherein the other one of the binding sites (i.e. the binding site formed by the pair of the VL domain of the common light chain and the VH domain of the heavy chain derived from the second antibody [$VH_2$]) specifically binds to at least one other (e.g. a second) antigen (see FIG. 2).

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively.

The terms "binding site" or "antigen-binding site" as used herein denotes the region(s) of a multispecific antibody as described herein to which a ligand (e.g. the antigen or antigen fragment of it) actually binds and which is derived from an antibody molecule or a fragment thereof. The antigen-binding site of an antibody according to the invention comprises an antibody heavy chain variable domain (VH) and an antibody light chain variable domain (VL).

The antigen-binding sites (i.e the pairs of VH/VL domains) that specifically bind to the desired antigen can be derived a) from known antibodies specifically binding to the antigen or b) from new antibodies or antibody fragments obtained by de novo immunization methods using inter alia either the antigen protein or nucleic acid or fragments thereof or by phage display. For the multispecific antibody described herein, which binds to a first and a second antigen, the antigen binding sites which binds to the first and the second antigen comprise both a first common light chain variable domain (VL) and a second common light chain variable domain (VL), which are identical for both antigen binding sites.

An antigen-binding site of a multispecific antibody of the invention contains six complementarity determining regions (CDRs) which contribute in varying degrees to the affinity of the binding site for antigen. There are three heavy chain variable domain CDRs (CDRH1, CDRH2 and CDRH3) and three light chain variable domain CDRs (CDRL1, CDRL2 and CDRL3). The extent of CDR and framework regions (FRs) is determined by comparison to a compiled database of amino acid sequences in which those regions have been defined according to variability among the sequences.

Antibody specificity refers to selective recognition of the antibody or a binding site of the multispecific antibody for a particular epitope of an antigen. Natural antibodies, for example, are monospecific. Bispecific antibodies are antibodies which have two different antigen-binding specificities. Where an antibody has more than one specificity, the recognized epitopes may be associated with a single antigen or with more than one antigen.

The term "common light chain" as used herein refers to a light chain which is capable of pairing with a first heavy chain of an antibody which binds to a first antigen in order to form a binding site specifically binding to said first antigen and which is also capable of pairing with a second heavy chain of an antibody which binds to a second antigen in order to form a binding site specifically binding to said second antigen. A common light chain is a polypeptide comprising in N-terminal to C-terminal direction an antibody light chain variable domain (VL), and an antibody light chain constant domain (CL), which is herein also abbreviated as "VL-CL". Within the multispecific antibody according to the invention, the common light chain variable domain VL pairs with the heavy chain variable domain derived from the antibody specifically binding to the first antigen ($VH_1$) to form an antigen binding site specifically binding to the first antigen. In addition, the common light chain variable domain VL pairs with the heavy chain variable domain derived from the antibody specifically binding to the second antigen ($VH_2$) to form an antigen binding site specifically binding to the second antigen. Hence, the multispecific antibody described herein comprising such a common light chain variable domain comprises two identical common light chain variable domains (VL), which pair with $VH_1$ and a $VH_2$ to form antigen bindings site [$VH_1$/VL] which binds to a first antigen and [$VH_2$/VL] which binds to a second antigen. The two common light chain variable domains (VL) included within the multispecific antibody exhibit at least 95%, in one embodiment at least 99%, in one further embodiment 100% amino acid sequence identity.

Common light chains and methods to generate such common light chains including the common light chain variable domain (VL) thereof are described, e.g. in WO 98/50431 or in WO2010/084197, or in US 2013/045492, WO2011097603 and WO2012148873 (wherein a common light chain mouse was used). Also in example 1 as outlined herein, the generation of a common light chain and its variable domain is described in detail. The use of one common light chain variable domain within a multispecific antibody avoids the formation of heterodimers in which pairing of light chains derived from a first antibody and heavy chains derived from a second antibody results in antigen-binding domains that are not functional or, in other words, which are not capable of binding to the target antigen or antigens.

By "modified light chain" as used herein is meant a light chain, wherein by recombinant means at least one of its domains (variable or constant domain) has been exchanged by a corresponding heavy chain domain. In particular, within the multispecific antibody according to the invention, within the modified light chain the light chain variable domain VL was replaced by the heavy chain variable domain VH derived from the corresponding heavy chain. Therefore, a modified light chain of an antibody of the invention comprises from N-terminal to C-terminal direction the domains VH-CL.

By "modified heavy chain" as used herein is meant a heavy chain, wherein by recombinant means at least one of its domains (variable domain VH or constant domain CH1) has been exchanged by a corresponding light chain domain. In particular, within the multispecific antibody according to the invention, within the modified heavy chain the heavy chain variable domain VH was replaced by the light chain variable domain VL derived from the corresponding light chain. Therefore, a modified heavy chain of an antibody of the invention comprises in N-terminal to C-terminal direction at least the domains VL-CH1.

A multispecific antibody according to the invention comprises two modified heavy chains, both of which comprise at least the light chain variable domain VL of the common light chain and a constant heavy chain domain 1 (VL-CH1). In one embodiment, the modified heavy chains comprise in N-terminal to C-terminal direction the domains VL-CH1-CH2-CH3 and typically comprise a hinge region located between the CH1 and CH2 domains. In one embodiment, the modified heavy chains of the multispecific antibody exhibit at least 95%, in one embodiment at least 99%, in one further embodiment 100% amino acid sequence identity.

However, antibodies produced by host cells may undergo post-translational cleavage of one or more, particularly one or two, amino acids from the C-terminus of the heavy chain. Therefore an antibody produced by a host cell by expression of a specific nucleic acid molecule encoding a full-length heavy chain may include the full-length heavy chain, or it may include a cleaved variant of the full-length heavy chain (also referred to herein as a cleaved variant heavy chain). This may be the case where the final two C-terminal amino acids of the heavy chain are glycine (G446) and lysine (K447, numbering according to Kabat EU index). The population of antibodies may comprise antibodies having a full-length heavy chain and antibodies having a cleaved variant heavy chain. The population of antibodies may consist of a mixture of antibodies having a full-length heavy chain and antibodies having a cleaved variant heavy chain, wherein at least 50%, at least 60%, at least 70%, at least 80% or at least 90% of the antibodies have a cleaved variant heavy chain.

The term "monospecific" antibody as used herein denotes an antibody that has one or more binding sites each of which bind to the same epitope of the same antigen.

The term "valent" as used herein denotes the presence of a specified number of binding sites in an antibody molecule. A natural antibody for example or a full length antibody according to the invention has two binding sites and is bivalent. As such, the terms "bivalent", "tetravalent", and "hexavalent" denote the presence of two binding sites, four binding sites, and six binding sites, respectively, in an antibody molecule. The multispecific antibodies according to the invention are preferably bivalent, bispecific antibodies.

In a preferred embodiment, the multispecific antibodies of the invention are full length antibodies, i.e. comprise immunoglobulin constant regions. The full length antibodies of the invention comprise immunoglobulin constant regions of one or more immunoglobulin classes. Immunoglobulin classes include IgG, IgM, IgA, IgD, and IgE isotypes and, in the case of IgG and IgA, their subtypes. In a preferred embodiment, a full length antibody of the invention has a constant domain structure of an IgG isotype antibody.

The terms "monoclonal antibody" or "monoclonal antibody composition" as used herein refer to a preparation of antibody or antibody molecules of a single amino acid composition.

The term "chimeric antibody" refers to an antibody comprising a variable region, i.e., binding region, from one source or species and at least a portion of a constant region derived from a different source or species, usually prepared by recombinant DNA techniques. Chimeric antibodies comprising a murine variable region and a human constant region are preferred. Other preferred forms of "chimeric antibodies" encompassed by the present invention are those in which the constant region has been modified or changed from that of the original antibody to generate the properties according to the invention, especially in regard to C1q binding and/or Fc receptor (FcR) binding. Such chimeric antibodies are also referred to as "class-switched antibodies.". Chimeric antibodies are the product of expressed immunoglobulin genes comprising DNA segments encoding immunoglobulin variable regions and DNA segments encoding immunoglobulin constant regions. Methods for producing chimeric antibodies involve conventional recombinant DNA and gene transfection techniques are well known in the art. See, e.g., Morrison, S., L., et al., Proc. Natl. Acad. Sci. USA 81 (1984) 6851-6855; U.S. Pat. Nos. 5,202,238 and 5,204,244.

The term "humanized antibody" refers to antibodies in which the framework or "complementarity determining regions" (CDR) have been modified to comprise the CDR of an immunoglobulin of different specificity as compared to that of the parent immunoglobulin. In a preferred embodiment, a murine CDR is grafted into the framework region of a human antibody to prepare the "humanized antibody." See, e.g., Riechmann, L., et al., Nature 332 (1988) 323-327; and Neuberger, M. S., et al., Nature 314 (1985) 268-270. Particularly preferred CDRs correspond to those representing sequences recognizing the antigens noted above for chimeric antibodies. Other forms of "humanized antibodies" encompassed by the present invention are those in which the constant region has been additionally modified or changed from that of the original antibody to generate the properties according to the invention, especially in regard to C1q binding and/or Fc receptor (FcR) binding.

The term "human antibody", as used herein, is intended to include antibodies having variable and constant regions derived from human germ line immunoglobulin sequences. Human antibodies are well-known in the state of the art (van Dijk, M. A., and van de Winkel, J. G., Curr. Opin. Chem. Biol. 5 (2001) 368-374). Human antibodies can also be produced in transgenic animals (e.g., mice) that are capable, upon immunization, of producing a full repertoire or a selection of human antibodies in the absence of endogenous immunoglobulin production. Transfer of the human germ-line immunoglobulin gene array in such germ-line mutant mice will result in the production of human antibodies upon antigen challenge (see, e.g., Jakobovits, A., et al., Proc. Natl. Acad. Sci. USA 90 (1993) 2551-2555; Jakobovits, A., et al., Nature 362 (1993) 255-258; Brueggemann, M., et al., Year Immunol. 7 (1993) 33-40). Human antibodies can also be produced in phage display libraries (Hoogenboom, H. R., and Winter, G., J. Mol. Biol. 227 (1992) 381-388; Marks, J. D., et al., J. Mol. Biol. 222 (1991) 581-597). The techniques of Cole et al. and Boerner et al. are also available for the preparation of human monoclonal antibodies (Cole, S., P., C., et al., Monoclonal Antibodies and Cancer Therapy, Alan R. Liss (1985) 77-96; and Boerner, P., et al., J. Immunol. 147 (1991) 86-95). As already mentioned for chimeric and humanized antibodies according to the invention the term "human antibody" as used herein also comprises such antibodies which are modified in the constant region to generate the properties according to the invention, especially in regard to C1q binding and/or FcR binding, e.g. by "class switching" i.e. change or mutation of Fc parts (e.g. from IgG1 to IgG4 and/or IgG1/IgG4 mutation.).

The term "recombinant human antibody", as used herein, is intended to include all human antibodies that are prepared, expressed, created or isolated by recombinant means, such as antibodies isolated from a host cell such as a NS0 or CHO cell or from an animal (e.g. a mouse) that is transgenic for human immunoglobulin genes or antibodies expressed using a recombinant expression vector transfected into a host cell. Such recombinant human antibodies have variable and constant regions in a rearranged form. The recombinant human antibodies according to the invention have been subjected to in vivo somatic hypermutation. Thus, the amino acid sequences of the VH and VL regions of the recombinant antibodies are sequences that, while derived from and related to human germ line VH and VL sequences, may not naturally exist within the human antibody germ line repertoire in vivo.

The "variable domain" (variable domain of a heavy chain (VH) or variable domain of a light chain (VL)), as used herein denotes each of the pair of light and heavy chains, which is directly involved in the binding of the antibody to the antigen. Within the multispecific antibody of the invention two identical variable domains of a common light chain (VL) form two different antigen binding sites with a first variable domain of a heavy chain ($VH_1$) and a second variable domain of a heavy chain ($VH_2$).

The variable domains of human light chains and human heavy chains have the same general structure. Each variable domain comprises four framework (FR) regions whose sequences are widely conserved, which are connected by three "hypervariable regions" (or complementarity determining regions, CDRs). The framework regions adopt a β-sheet conformation and the CDRs may form loops connecting the β-sheet structure. The CDRs in each chain are held in their three-dimensional structure by the framework regions and form together with the CDRs from the other chain the antigen binding site. The antibody heavy and light chain CDR3 regions play a particularly important role in the binding specificity/affinity of antibodies.

An "individual" or "subject" as referred to herein is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is an antibody, which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC) means. For review of methods for assessment of antibody purity, see, e.g., Flatman, S. et al., J. Chromatogr. B 848 (2007) 79-87.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

The terms "hypervariable region" or "antigen-binding portion of an antibody" when used herein refer to the amino acid residues of an antibody which are responsible for antigen-binding. The hypervariable region comprises amino acid residues from the "complementarity determining regions" or "CDRs". "Framework" or "FR" regions are those variable domain regions other than the hypervariable region residues as herein defined. Therefore, the light and heavy chains of an antibody comprise from N- to C-terminus the domains FR1, CDR1, FR2, CDR2, FR3, CDR3, and FR4. CDRs on each chain are separated by such framework amino acids. Especially, CDR3 of the heavy chain is the region which contributes most to antigen binding. CDR and FR regions are determined according to the standard definition of Kabat, et al., Sequences of Proteins of Immunological Interest, 5th ed., Public Health Service, National Institutes of Health, Bethesda, Md. (1991).

As used herein, the term "binding" or "specifically binding" refers to the binding of the antibody to an epitope of the antigen in an in vitro assay, preferably in an plasmon resonance assay (BIAcore®, GE-Healthcare Uppsala, Sweden) with purified wild-type antigen. The affinity of the binding is defined by the terms ka (rate constant for the association of the antibody from the antibody/antigen complex), $k_D$ (dissociation constant), and $K_D$ ($k_D$/ka). "Binding" or "specifically binding" means a binding affinity ($K_D$) of $10^{-8}$ mol/l or less, in one embodiment of $10^{-8}$ M to $10^{-13}$ mol/l, in one embodiment of $10^{-9}$ M to $10^{-13}$ mol/l. Thus, in one embodiment of the invention a multispecific antibody as described herein is specifically binding to each antigen for which it is specific with a binding affinity ($K_D$) of $10^{-8}$ mol/l or less, in one further embodiment of $10^{-8}$ M to $10^{-13}$ mol/l, in one even further embodiment of $10^{-9}$ M to $10^{-13}$ mol/l.

The term "epitope" includes any polypeptide determinant capable of specific binding to an antibody. In certain embodiments, epitope determinant include chemically active surface groupings of molecules such as amino acids, sugar side chains, phosphoryl, or sulfonyl, and, in certain embodiments, may have specific three dimensional structural characteristics, and or specific charge characteristics. An epitope is a region of an antigen that is bound by an antibody.

The term "constant region" as used within the current applications denotes the sum of the domains of an antibody other than the variable region. The constant region is not directly involved in the binding to the antigen, but it exhibits various effector functions. Depending on the amino acid sequence of the constant region of their heavy chains, antibodies are divided in the classes: IgA, IgD, IgE, IgG and IgM, and several of these may be further divided into subclasses, such as IgG1, IgG2, IgG3, and IgG4, IgA1 and IgA2. The heavy chain constant regions that correspond to the different classes of antibodies are called α, δ, ε, γ, and μ, respectively. The light chain constant regions (CL) which can be found in all five antibody classes are called κ (kappa) and λ (lambda).

The term "constant region derived from human origin" as used in the current application denotes a constant heavy chain region of a human antibody of the subclass IgG1, IgG2, IgG3, or IgG4 and/or a constant light chain kappa or lambda region. Such constant regions are well known in the state of the art and e.g. described by Kabat, E. A., (see e.g. Johnson, G. and Wu, T. T., Nucleic Acids Res. 28 (2000) 214-218; Kabat, E. A., et al., Proc. Natl. Acad. Sci. USA 72 (1975) 2785-2788).

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical composition, refers to an amount effective, at dosages and for periods of time necessary, to achieve the desired therapeutic or prophylactic result.

The term "Fc region" herein is used to define a C-terminal region of an immunoglobulin heavy chain that contains at least a portion of the constant region.

The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat, E. A. et al., Sequences of Proteins of Immunological Interest, 5th ed., Public Health Service, National Institutes of Health, Bethesda, Md. (1991), NIH Publication 91-3242.

2. Detailed Description of the Embodiments of the Invention

The invention relates to a multispecific antibody, comprising
a) two modified heavy chains, wherein each heavy chain comprises in C-terminal to N-terminal direction heavy chain constant domains 3 to 1 (CH3, CH2 and CH1, in this order) and a light chain variable domain (VL), wherein the light chain variable domain (VL) is the variable domain of a common light chain;
b) one, in one embodiment exactly one, modified light chain, wherein the modified light chain comprises in C-terminal to N-terminal direction a constant light chain domain (CL) of kappa isotype (herein referred to as "CLκ") and a variable heavy chain domain ($VH_1$) derived from an antibody, which specifically binds to a first antigen; and
c) one, in one embodiment exactly one, modified light chain, wherein the modified light chain comprises in C-terminal to N-terminal direction a constant light chain domain of lambda isotype (herein referred to as "CLλ") and a variable heavy chain domain ($VH_2$) derived from an antibody, which specifically binds to a second antigen.

The invention also relates to a multispecific antibody, wherein the antibody comprises
a) two modified heavy chains, wherein each heavy chain comprises in C-terminal to N-terminal direction heavy chain constant domains 3 to 1 (CH3, CH2 and CH1, in this order) and a light chain variable domain (VL), wherein the light chain variable domain (VL) is a variable domain of a common light chain;
b) one, in one embodiment exactly one, modified first light chain, wherein the modified first light chain comprises in C-terminal to N-terminal direction a constant light chain domain (CL) of kappa isotype (herein referred to as "CLκ") and a variable heavy chain domain ($VH_1$) derived from an antibody, which specifically binds to a first antigen; and
c) one, in one embodiment exactly one, modified second light chain, wherein the modified second light chain comprises a polypeptide including in C-terminal to N-terminal direction a constant light chain domain of lambda isotype (herein referred to as "CLλ") and a variable heavy chain domain ($VH_2$) derived from an antibody, which specifically binds to a second antigen.

The invention further relates to a multispecific antibody, comprising:
a) two modified heavy chains comprising a polypeptide consisting of the domains CH3-CH2-CH1-VL, wherein VL is the variable domain of a common light chain;
b) one modified light chain comprising a polypeptide consisting of the domains CLκ-$VH_1$, wherein $VH_1$ is the variable heavy chain domain from an antibody which binds to a first antigen; and
c) one modified light chain comprising a polypeptide consisting of the domains CLλ-$VH_2$ wherein $VH_2$ is the variable heavy chain domain from an antibody which binds to a second antigen.

In one embodiment of the invention the multispecific antibody comprises
a) two modified heavy chains comprising a polypeptide consisting of CH3-CH2-CH1-VL, wherein VL is variable domain of a common light chain;
b) one modified light chain comprising a polypeptide consisting of CLκ-$VH_1$ wherein $VH_1$ is the variable heavy chain domain of an antibody which binds to a first antigen;
c) one modified light chain comprising a polypeptide consisting of CLλ-$VH_2$ wherein $VH_2$ is the variable heavy chain domain of an antibody which binds to a second antigen,
wherein the variable domains $VH_1$ and VL form a first antigen binding site, which specifically binds to a first antigen, and wherein the variable domains $VH_2$ and VL form a second antigen binding site, which specifically binds to a second antigen.

Within the multispecific antibody according to the invention the half of the antibody that recognizes the first antigen shares a common light chain variable domain with the half of the antibody recognizing the second antigen and said common light chain variable domain is swapped with the respective VH domain, giving rise to a CH3-CH2-CH1-VL type architecture. This ensures correct antibody chain association. Correct heavy chain pairing is ensured, since only one type of heavy chain is present within the multispecific antibody. In addition, correct light chain association is achieved due to the presence of one common light chain variable domain. Furthermore, the presence of CLκ linked to the $VH_1$ domain and CLλ linked to the $VH_2$ domain allows the purification of the desired bispecific antibody by applying subsequent purification steps with kappa- and lambda-specific columns to remove unwanted homodimers. Within the multispecific antibody according to the invention the variable domain VL of said first binding site and the variable domain VL of said second binding site exhibit at least 95%, in one embodiment at least 99%, in one further embodiment 100% amino acid sequence identity. In one embodiment, the variable domain VL of said first binding site and the variable domain VL of said second binding site are 100% identical in their amino acid sequence.

In one further aspect the invention relates to a multispecific antibody, comprising:
a) the first modified heavy chain and the first modified common light chain of an antibody which specifically binds to a first antigen; and
b) the second modified heavy chain and second modified common light chain of an antibody which specifically binds to a second antigen, wherein the variable domains VH and VL from the heavy chain and the first common light under a) are replaced by each other, wherein the variable domains VH and VL from the heavy chain and the second common light under b) are replaced by each other; and wherein the first common light under a) contains a kappa constant light chain domain CLκ; and wherein the second common light under b) contains a lambda constant light chain domain CLλ; and wherein both the VL domain from the first common light chain under a) and the VL domain of the second common light chain under b) are identical; and wherein both constant regions of the first heavy chain under a) and second heavy chain under b) are identical.

In one embodiment of the invention, the multispecific antibody is bivalent. In one embodiment of the invention, the multispecific antibody is a bispecific antibody. In one embodiment of the invention, the multispecific antibody is a bivalent, bispecific antibody.

In one embodiment of a multispecific antibody according to the invention, the heavy chain of the full length antibody consists in N-terminal to C-terminal direction a VH domain, a CH1 domain, a hinge region, a CH2 domain, and a CH3 comain. In one embodiment, the heavy chain of the full length antibody in N-terminal to C-terminal direction consists of a VH domain, a CH1 domain, a hinge region, a CH2 domain, and a CH3 comain. In one embodiment, the heavy chain of the full length antibody is a polypeptide consisting in N-terminal to C-terminal direction of VH, CH1, CH2 and CH3.

In one embodiment of the invention, the modified heavy chains comprise VL-CH1 domains, which are 100% identical in their amino acid sequence.

In one embodiment of the invention, the heavy chain constant domain CH3 of the multispecific antibody is not altered (i.e. by amino acid substitutions) to support heterodimerization. Specifically, the heavy chain constant domains CH3 are not asymmetrically altered, e.g. by the knobs-into-holes technology, wherein one CH3 domain is altered to produce a "knob" and the other CH3 domain is altered to produce a "hole", so that by placing the "knob" amino acid within the "hole" heterodimerization of different heavy chains is supported. In contrast, pne particular advantage of the multispecific antibodies of the invention is that there is no requirement for supporting heterodimerization as due to the domain exchange in the modified heavy chain the modified heavy chain can bind both light chains of the multispecific antibody and can, of course, pair with another identical heavy chain.

When referred to "identical" and "identity" between polypeptides herein (e.g. "identity" between heavy chains or "identity" between the common light chain variable domain VL) is meant a 100% identity of the amino acid sequence of the polypeptides. However, the polypeptides may differ in glycan structures attached to the polypeptide chain.

One aspect of the invention is a method for the generation of a multispecific antibody, comprising the steps of
a) modifying a first heavy chain and a first common light chain of an antibody which specifically binds to a first antigen, by exchanging the variable domains VH$_1$ and VL from the heavy chain and the common light by each other; and
b) modifying the first common light to contain a kappa constant light chain domain CLκ
c) modifying a second heavy chain and a second common light chain of an antibody which specifically binds to a second antigen, by exchanging the variable domains VH$_2$ and VL from the heavy chain and the common light by each other; and
d) modifying the second common light to contain a lambda constant light chain domain CLλ;
wherein both variable light chain domains VL from the first common light of the second common light chain under b) are identical; and wherein both constant regions of the first and second heavy chain are identical.

Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the CDRs and FRs. In one embodiment, substitutional mutagenesis was performed in CDRs and/or FRs of the heavy chain. Exemplary changes are provided in Table 1 under the heading of "exemplary substitutions", and as further described below in reference to amino acid side chain classes. Conservative substitutions are shown in Table 1 under the heading of "preferred substitutions". Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;

(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more CDR residues are mutated and the variant antibodies displayed on phage and screened for a particular biological activity (e.g. binding affinity).

Alterations (e.g., substitutions) may be made in CDRs, e.g., to improve antibody affinity. Such alterations may be made in CDR "hotspots," i.e., residues encoded by codons that undergo mutation at high frequency during the somatic maturation process (see, e.g., Chowdhury, P. S., Methods Mol. Biol. 207 (2008) 179-196), and/or SDRs (a-CDRs), with the resulting variant VH or VL being tested for binding affinity. Affinity maturation by constructing and reselecting from secondary libraries has been described, e.g., in Hoogenboom, H. R. et al. in Methods in Molecular Biology 178 (2002) 1-37. In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves CDR-directed approaches, in which several CDR residues (e.g., 4-6 residues at a time) are randomized. CDR residues involved in antigen binding may be specifically identified, e.g., using alanine scanning mutagenesis or modeling. CDR-H3 and CDR-L3 in particular are often targeted.

A useful method for identification of residues or regions of an antibody that may be targeted for mutagenesis is called "alanine scanning mutagenesis" as described by Cunningham, B. C. and Wells, J. A., Science 244 (1989) 1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright, A. and Morrison, S. L., TIBTECH 15 (1997) 26-32. The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (Eu index numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US 2003/0157108; US 2004/0093621. Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO 2005/053742; WO 2002/031140; Okazaki, A. et al., J. Mol. Biol. 336 (2004) 1239-1249; Yamane-Ohnuki, N. et al., Biotech. Bioeng. 87 (2004) 614-622. Examples of cell lines capable of producing defucosylated antibodies include Lec13 CHO cells deficient in protein fucosylation (Ripka, J. et al., Arch. Biochem. Biophys. 249 (1986) 533-545; US 2003/0157108; and WO 2004/056312, especially at Example 11), and knockout cell lines, such as alpha-1,6-fucosyltransferase gene, FUT8, knockout CHO cells (see, e.g., Yamane-Ohnuki, N. et al., Biotech. Bioeng. 87 (2004) 614-622; Kanda, Y. et al., Biotechnol. Bioeng. 94 (2006) 680-688; and WO 2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878; U.S. Pat. No. 6,602,684; and US 2005/0123546. Antibody variants with at least one galactose residue in the oligosaccharide attached to the Fc region are also provided. Such antibody variants may have improved CDC function. Such antibody variants are described, e.g., in WO 1997/30087; WO 1998/58964; and WO 1999/22764.

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions. In one embodiment, said amino acid modification at one or more amino acid positions is identical in both heavy chains of the antibody according to the invention.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express FcγRI, FcγRII and FcγRIII. FcR expression on hematopoietic cells is summarized in Table 3 on page 464 of Ravetch, J. V. and Kinet, J. P., Annu. Rev. Immunol. 9 (1991) 457-492. Non-limiting examples of in vitro assays to assess ADCC activity of a molecule of interest is described in U.S. Pat. No. 5,500,362 (see, e.g. Hellstrom, I. et al., Proc. Natl. Acad. Sci. USA 83 (1986) 7059-7063; and Hellstrom, I. et al., Proc. Natl. Acad. Sci. USA 82 (1985) 1499-1502); U.S. Pat. No. 5,821,337 (see Bruggemann, M. et al., J. Exp. Med. 166 (1987) 1351-1361). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes, R. et al., Proc. Natl. Acad. Sci. USA 95 (1998) 652-656. C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro, H. et al., J. Immunol. Methods 202 (1996) 163-171; Cragg, M. S. et al., Blood 101 (2003) 1045-1052; and Cragg, M. S. and M. J. Glennie, Blood 103 (2004) 2738-2743). FcRn binding and in vivo clearance/half life determinations can also be performed using methods known in the art (see, e.g., Petkova, S. B. et al., Int. Immunol. 18 (2006: 1759-1769).

Antibodies with reduced effector function include those with substitution of one or more of Fc region residues 238, 265, 269, 270, 297, 327 and 329 (U.S. Pat. No. 6,737,056, numbering according to EU index of Kabat). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581, numbering according to EU index of Kabat).

As used herein, the amino acid positions of all constant regions and domains of the heavy and light chain are numbered according to the Kabat numbering system described in Kabat, et al., Sequences of Proteins of Immunological Interest, 5th ed., Public Health Service, National Institutes of Health, Bethesda, Md. (1991). In particular, for variable domains and for the light chain constant domain CL of kappa and lambda isotype, the Kabat numbering system (see pages 647-660) of Kabat, et al., Sequences of Proteins of Immunological Interest, 5th ed., Public Health Service, National Institutes of Health, Bethesda, Md. (1991) is used and is herein referred to as "numbering according to Kabat" and for the constant heavy chain domains (CH1, Hinge, CH2 and CH3) the Kabat EU index numbering system (see pages 661-723) is used and is herein referred to as "numbering according to EU index of Kabat".

In one embodiment the multispecific antibody is of IgG isotype. In one embodiment the multispecific antibody is of IgG1 or IgG4 isotype.

In one embodiment the multispecific antibody contains a constant heavy chain region of IgG1 subclass which comprises the mutations L234A and L235A (numbering according to EU index of Kabat; Kabat, E. A. et al., Sequences of Proteins of Immunological Interest, 5th ed., Public Health Service, National Institutes of Health, Bethesda, Md. (1991), NIH Publication 91-3242.)

In one embodiment the multispecific antibody contains a constant heavy chain region of IgG1 subclass which comprises the mutations L234A, L235A and P329G (numbering according to EU index of Kabat).

In one embodiment the multispecific antibody contains a constant heavy chain region of IgG4 subclass.

In one embodiment the multispecific antibody contains a constant heavy chain region of IgG4 subclass which comprises the mutations S228P and L235E (numbering according to EU index of Kabat).

In one embodiment the multispecific antibody contains a constant heavy chain region of IgG4 subclass which comprises the mutations S228P, L235E and P329G (numbering according to EU index of Kabat).

Certain antibody variants with improved or diminished binding to FcRs are described (see, e.g., U.S. Pat. No. 6,737,056; WO 2004/056312, and Shields, R. L. et al., J. Biol. Chem. 276 (2001) 6591-6604).

In certain embodiments, an antibody variant comprises an Fc region with one or more amino acid substitutions which improve ADCC, e.g., substitutions at positions 298, 333, and/or 334 of the Fc region (numbering according to EU index of Kabat).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie, E. E. et al., J. Immunol. 164 (2000) 4178-4184.

Antibodies with increased half lives and improved binding to the neonatal Fc receptor (FcRn), which is responsible for the transfer of maternal IgGs to the fetus (Guyer, R. L. et al., J. Immunol. 117 (1976) 587-593, and Kim, J. K. et al., J. Immunol. 24 (1994) 2429-2434), are described in US 2005/0014934. Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan, A. R. and Winter, G., Nature 322 (1988) 738-740; U.S. Pat. Nos. 5,648,260; 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (numbering according to Kabat) of the light chain; A118 (numbering according to EU index of Kabat) of the heavy chain; and S400 (numbering according to EU index of Kabat) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional non-proteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and non-proteinaceous moiety that may be selectively heated by exposure to radiation are provided. In one embodiment, the non-proteinaceous moiety is a carbon nanotube (Kam, N. W. et al., Proc. Natl. Acad. Sci. USA 102 (2005) 11600-11605). The radiation may be of any wavelength, and includes, but is not limited to, wavelengths that do not harm ordinary cells, but which heat the non-proteinaceous moiety to a temperature at which cells proximal to the antibody-non-proteinaceous moiety are killed.

Recombinant Methods and Compositions

Antibodies may be produced using recombinant methods and compositions, e.g., as described in U.S. Pat. No. 4,816,567.

One aspect of the invention is a method for the preparation of a multispecific antibody according the invention, comprising the steps of
a) transforming a host cell with expression vectors comprising nucleic acid molecules encoding a multispecific antibody according to the invention;
b) culturing the host cell under conditions that allow synthesis of said multispecific antibody molecule; and
c) recovering said multispecific antibody molecule from said culture.

In one embodiment of the invention, the host cell is transformed with (i) expression vectors comprising nucleic acid molecules encoding the modified heavy chain, (ii) expression vectors comprising nucleic acid molecules encoding the modified light chain comprising in C-terminal to N-terminal direction a constant light chain domain (CL) of kappa isotype (CLκ) and a variable heavy chain domain (VH$_1$) derived from an antibody, which specifically binds to a first antigen; and (iii) expression vectors comprising nucleic acid molecules encoding the modified light chain comprising in C-terminal to N-terminal direction a constant light chain domain of lambda isotype (CLλ) and a variable heavy chain domain (VH$_2$) derived from an antibody, which specifically binds to a second antigen. In one embodiment of the invention, the host cell is transformed with a molar amount of expression vectors comprising nucleic acid molecules encoding the modified heavy chain, which is about (in one embodiment, which equals) the molar amount of the sum of the molar amounts used for transforming the host cell with the expression vectors of the respective light chains as defined aforementioned under (ii) and (iii).

In one embodiment, for the generation of a multispecific antibody according to the invention exactly one type of expression vector including a nucleic acid encoding for the modified heavy chain is used. In one embodiment, for the generation of a multispecific antibody according to the invention a nucleic acid encoding for the modified heavy chain is used.

In one embodiment, an isolated nucleic acid encoding a multispecific antibody described herein is provided. Such nucleic acid may encode an amino acid sequence comprising the VL and/or an amino acid sequence comprising the VH of the antibody (e.g., the light and/or heavy chains of the antibody).

"Polynucleotide" or "nucleic acid" as used interchangeably herein, refers to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. A sequence of nucleotides may be interrupted by non-nucleotide components. A polynucleotide may comprise modification(s) made after synthesis, such as conjugation to a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotides(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl-, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs, and basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR2 ("amidate"), P(O)R, P(O)OR', CO, or CH2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

In a further embodiment, one or more vectors comprising such nucleic acid are provided. In an even further embodiment, one or more expression vectors comprising such nucleic acid are provided. In one embodiment, an expression vector containing such nucleic acid capable of expressing said nucleic acid in a prokaryotic or eukaryotic host cell is provided.

In a further embodiment, a host cell comprising such nucleic acid is provided. In an even further embodiment, a prokaryotic or eukaryotic host cell comprising a such an expression vector as defined above is provided. In one embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell).

In one embodiment, a method of making a multispecific antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of a multispecific antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, K. A., In: Methods in Molecular Biology, Vol. 248, Lo, B. K. C. (ed.), Humana Press, Totowa, N.J. (2003), pp. 245-254, describing expression of antibody fragments in E. coli.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, T. U., Nat. Biotech. 22 (2004) 1409-1414; and Li, H. et al., Nat. Biotech. 24 (2006) 210-215.

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of Spodoptera frugiperda cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham, F. L. et al., J. Gen Virol. 36 (1977) 59-74); baby hamster kidney cells (BHK); mouse sertoli cells (TM4 cells as described, e.g., in Mather, J. P., Biol. Reprod. 23 (1980) 243-252); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather, J. P. et al., Annals N.Y. Acad. Sci. 383 (1982) 44-68; MRC 5 cells; and FS4 cells. Other useful mammalian host cell lines include Chinese hamster ovary (CHO) cells, including DHFR⁻ CHO cells (Urlaub, G. et al., Proc. Natl. Acad. Sci. USA 77 (1980) 4216-4220); and myeloma cell lines such as Y0, NS0 and Sp2/0. For a review of certain mammalian host cell lines suitable for antibody production, see, e.g., Yazaki, P. and Wu, A. M., Methods in Molecular Biology, Vol. 248, Lo, B. K. C. (ed.), Humana Press, Totowa, N.J. (2004), pp. 255-268.

The multispecific antibody according to the invention is produced by recombinant means. Thus, one aspect of the current invention is a nucleic acid encoding the multispecific antibody according to the invention and a further aspect is a cell comprising said nucleic acid encoding a multispecific antibody according to the invention. Methods for recombinant production are widely known in the state of the art and comprise protein expression in prokaryotic and eukaryotic cells with subsequent isolation of the multispecific antibody and usually purification to a pharmaceutically acceptable purity.

For the expression of the antibodies as aforementioned in a host cell, nucleic acids encoding the respective modified light and heavy chains are inserted into expression vectors by standard methods. Expression is performed in appropriate prokaryotic or eukaryotic host cells like CHO cells, NS0 cells, SP2/0 cells, HEK293 cells, COS cells, PER.C6 cells, yeast, or *E. coli* cells, and the antigen binding protein is recovered from the cells (supernatant or cells after lysis). General methods for recombinant production of antibodies are well-known in the state of the art and described, for example, in the review articles of Makrides, S. C., Protein Expr. Purif. 17 (1999) 183-202; Geisse, S., et al., Protein Expr. Purif. 8 (1996) 271-282; Kaufman, R. J., Mol. Biotechnol. 16 (2000) 151-160; Werner, R. G., Drug Res. 48 (1998) 870-880.

The multispecific antibodies according to the invention have one constant kappa light chain domain (CLκ) and one constant lambda light chain domain (CLλ) and are suitably separated from the culture medium by conventional immunoglobulin purification procedures such as, for example, protein A-Sepharose, hydroxylapatite chromatography, gel electrophoresis, dialysis, or affinity chromatography, specifically the multispecific antibodies according to the invention are purified by two sequential affinity chromatography steps using kappa light chain and lambda light chain affinity chromatography, followed by a size exclusion chromatographic step (as e.g. described in Example 3).

The term "host cell" as used in the current application denotes any kind of cellular system which can be engineered to generate the antibodies according to the current invention. In one embodiment HEK293 cells and CHO cells are used as host cells.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included.

Expression in NS0 cells is described by, e.g., Barnes, L. M., et al., Cytotechnology 32 (2000) 109-123; Barnes, L. M., et al., Biotech. Bioeng. 73 (2001) 261-270. Transient expression is described by, e.g., Durocher, Y., et al., Nucl. Acids. Res. 30 (2002) E9. Cloning of variable domains is described by Orlandi, R., et al., Proc. Natl. Acad. Sci. USA 86 (1989) 3833-3837; Carter, P., et al., Proc. Natl. Acad. Sci. USA 89 (1992) 4285-4289; and Norderhaug, L., et al., J. Immunol. Methods 204 (1997) 77-87. A preferred transient expression system (HEK 293) is described by Schlaeger, E.-J., and Christensen, K., in Cytotechnology 30 (1999) 71-83 and by Schlaeger, E.-J., in J. Immunol. Methods 194 (1996) 191-199.

The control sequences that are suitable for prokaryotes, for example, include a promoter, optionally an operator sequence, and a ribosome binding site. Eukaryotic cells are known to utilize promoters, enhancers and polyadenylation signals.

A nucleic acid is "operably linked" when it is placed in a functional relationship with another nucleic acid sequence. For example, DNA for a pre-sequence or secretory leader is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

The term "transformation" as used herein refers to process of transfer of a vectors/nucleic acid into a host cell. If cells without formidable cell wall barriers are used as host cells, transfection is carried out e.g. by the calcium phosphate precipitation method as described by Graham, F., L., and Van der Eb, A., J., Virology 52 (1973) 456-467. However, other methods for introducing DNA into cells such as by nuclear injection or by protoplast fusion may also be used. If prokaryotic cells or cells which contain substantial cell wall constructions are used, e.g. one method of transfection is calcium treatment using calcium chloride as described by Cohen, S., N., et al, PNAS. 69 (1972) 2110-2114.

As used herein, "expression" refers to the process by which a nucleic acid is transcribed into mRNA and/or to the process by which the transcribed mRNA (also referred to as transcript) is subsequently being translated into peptides, polypeptides, or proteins. The transcripts and the encoded polypeptides are collectively referred to as gene product. If the polynucleotide is derived from genomic DNA, expression in a eukaryotic cell may include splicing of the mRNA.

A "vector" is a nucleic acid molecule, in particular self-replicating, which transfers an inserted nucleic acid molecule into and/or between host cells. The term includes vectors that function primarily for insertion of DNA or RNA into a cell (e.g., chromosomal integration), replication of vectors that function primarily for the replication of DNA or RNA, and expression vectors that function for transcription and/or translation of the DNA or RNA. Also included are vectors that provide more than one of the functions as described.

An "expression vector" is a polynucleotide which, when introduced into an appropriate host cell, can be transcribed and translated into a polypeptide. An "expression system" usually refers to a suitable host cell comprised of an expression vector that can function to yield a desired expression product.

Purification of antibodies is performed in order to eliminate cellular components or other contaminants, e.g. other cellular nucleic acids or proteins, by standard techniques, including alkaline/SDS treatment, CsCl banding, column chromatography, agarose gel electrophoresis, and others well known in the art. See Ausubel, F., et al., ed. Current Protocols in Molecular Biology, Greene Publishing and Wiley Interscience, New York (1987). As the intact multispecific antibodies according to the invention comprise two different constant light chain domains (kappa and lambda) at each arm of the antibody, they can purified from incomplete or mispaired byproducts by two sequential affinity chromatography steps using kappa light chain and lambda light chain affinity chromatography, followed by a size exclusion chromatographic step (as e.g. described in Example 3).

In general different methods are well established and widespread used for protein purification, such as affinity chromatography with microbial proteins (e.g. protein A or protein G affinity chromatography), ion exchange chromatography (e.g. cation exchange (carboxymethyl resins), anion exchange (amino ethyl resins) and mixed-mode exchange), thiophilic adsorption (e.g. with beta-mercaptoethanol and other SH ligands), hydrophobic interaction or aromatic adsorption chromatography (e.g. with phenyl-sepharose, aza-arenophilic resins, or m-aminophenylboronic acid), metal chelate affinity chromatography (e.g. with Ni(II)- and Cu(II)-affinity material), size exclusion chromatography, and electrophoretical methods (such as gel electrophoresis, capillary electrophoresis) (Vijayalakshmi, M. A., Appl. Biochem. Biotech. 75 (1998) 93-102).

The term "pharmaceutical composition" refers to a preparation which is in such form as to permit the biological activity of an active ingredient contained therein to be effective, and which contains no additional components which are unacceptably toxic to a subject to which the composition would be administered. A pharmaceutical composition comprises a therapeutically effective amount of the active ingredient in combination with a pharmaceutically acceptable carrier.

A "pharmaceutically acceptable carrier" or "pharmaceutically acceptable excipient" refers to an ingredient in a pharmaceutical composition, other than an active ingredient, which is nontoxic to a subject. A pharmaceutically acceptable carrier or excipient includes, but is not limited to, a buffer, excipient, stabilizer, or preservative.

Pharmaceutical Compositions

Pharmaceutical compositions of a multispecific antibody as described herein are prepared by mixing such antibody having the desired degree of purity with one or more optional pharmaceutically acceptable carriers (Remington's Pharmaceutical Sciences, 16th edition, Osol, A. (ed.) (1980)), in the form of lyophilized compositions or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyl dimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as poly(vinylpyrrolidone); amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rhuPH20 (HYLENEX®, Baxter International, Inc.). Certain exemplary sHASEGPs and methods of use, including rhuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations/compositions are described in U.S. Pat. No. 6,267,958. Aqueous antibody formulations/compositions include those described in U.S. Pat. No. 6,171,586 and WO 2006/044908, the latter formulations/compositions including a histidine-acetate buffer.

The composition disclosed herein may also contain more than one active ingredients as necessary for the particular indication being treated, preferably those with complementary activities that do not adversely affect each other. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methyl methacrylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, 16th edition, Osol, A. (ed.) (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The compositions to be used for in vivo administration are generally sterile. Sterility may be readily accomplished, e.g., by filtration through sterile filtration membranes.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

One aspect of the invention is a pharmaceutical composition comprising a multispecific antibody according to the invention.

Another aspect of the invention is the use of a multispecific antibody according to the invention for the manufacture of a pharmaceutical composition.

A further aspect of the invention is a method for the manufacture of a pharmaceutical composition comprising an a multispecific antibody according to the invention.

In another aspect, the present invention provides a composition, e.g. a pharmaceutical composition, containing an a multispecific antibody according to the present invention, formulated together with a pharmaceutical carrier.

Another aspect of the invention is said pharmaceutical composition for use as a medicament. Another aspect of the invention is said pharmaceutical composition for the treatment of cancer.

Another aspect of the invention is the multispecific antibody according to the invention for use as a medicament. Another aspect of the invention is the multispecific antibody according to the invention for the treatment of cancer.

Another aspect of the invention is the use of a multispecific antibody according to the invention for the manufacture of a medicament. Another aspect of the invention is the use of a multispecific antibody according to the invention for the manufacture of a medicament for the treatment of cancer.

Another aspect of the invention is a method of treatment of a patient suffering from a disease by administering a multispecific antibody according to the invention to said patient in the need of such treatment. Another aspect of the invention is a method of treatment of a patient suffering from cancer by administering a multispecific antibody according to the invention to said patient in the need of such treatment.

A pharmaceutical composition of the present invention can be administered by a variety of methods known in the art. As will be appreciated by the skilled artisan, the route and/or mode of administration will vary depending upon the desired results. To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Pharmaceutical carriers include sterile aqueous solutions or dispersions and sterile powders for the extemporaneous preparation of sterile injectable solutions or dispersion. The use of such media and agents for pharmaceutically active substances is known in the art.

The phrases "parenteral administration" and "administered parenterally" as used herein means modes of administration other than enteral and topical administration, usually by injection, and includes, without limitation, intravenous, intramuscular, intra-arterial, intrathecal, intracapsular, intraorbital, intracardiac, intradermal, intraperitoneal, transtracheal, subcutaneous, subcuticular, intra-articular, subcapsular, subarachnoid, intraspinal, epidural and intrasternal inj ecti on and infusion.

The term cancer as used herein refers to proliferative diseases, such as lymphomas, lymphocytic leukemias, lung cancer, non small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma and Ewings sarcoma, including refractory versions of any of the above cancers, or a combination of one or more of the above cancers.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol, sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The composition must be sterile and fluid to the extent that the composition is deliverable by syringe. In addition to water, the carrier preferably is an isotonic buffered saline solution.

Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition.

The following examples and figures are provided to aid the understanding of the present invention, the true scope of which is set forth in the appended claims. It is understood that modifications can be made in the procedures set forth without departing from the spirit of the invention.

3. Specific Embodiments of the Invention

In the following, specific embodiments of the invention are listed:
1. A multi specific antibody, comprising:
   a) two modified heavy chains; wherein each heavy chain comprises in C-terminal to N-terminal direction heavy chain constant domains 3, 2 and 1 (CH3, CH2 and CH1) and a light chain variable domain (VL), wherein the light chain variable domain (VL) is the variable domain of a common light chain;
   b) one modified light chain, wherein the modified light chain comprises in C-terminal to N-terminal direction a constant light chain domain (CL) of kappa isotype and a variable heavy chain domain ($VH_1$) derived from an antibody, which specifically binds to a first antigen; and
   c) one modified light chain, wherein the modified light chain comprises in C-terminal to N-terminal direction a constant light chain domain of lambda isotype and a variable heavy chain domain ($VH_2$) derived from an antibody, which specifically binds to a second antigen; wherein the variable domains $VH_1$ and VL form a first antigen binding site which specifically binds to a first antigen, and wherein the variable domains $VH_2$ and VL form a second antigen binding site which specifically binds to second antigen.
2. The antibody according to embodiment 1, wherein the antibody is bispecific.
3. The antibody according to embodiment 1 or 2, wherein the antibody is bivalent.

4. The antibody according to any one of the preceding embodiments, wherein the antibody is bispecific and bivalent.
5. The antibody according to any one of the preceding embodiments, wherein the antibody is of IgG1 or IgG4 subclass.
6. The antibody according to any one of the preceding embodiments, wherein the antibody is of IgG1 subclass.
7. The antibody according to any one of the preceding embodiments, wherein the antibody is of IgG4 subclass.
8. The antibody according to any one of the preceding embodiments, wherein the modified heavy chains comprise VL-CH1 domains, which are 100% identical in their amino acid sequence.
9. The antibody according to any one of the preceding embodiments, wherein the heavy chain constant domains CH3 of the multispecific antibody are not altered by amino acid substitutions to support heterodimerization.
10. The antibody according to any one of the preceding embodiments, wherein the heavy chain constant domains CH3 of the multispecific antibody are not altered by amino acid substitutions according to the knobs-into-holes technology to support heterodimerization.
11. The antibody according to any one of the preceding embodiments, wherein the heavy chain constant domains CH3 of the multispecific antibody are 100% identical in their amino acid sequence.
12. The antibody according to any one of the preceding embodiments, wherein
  a) the modified heavy chains consist in C-terminal to N-terminal direction of CH3-CH2-hinge-CH1-VL, wherein the VL is the variable domain of a common light chain;
  b) a first modified light chain consists in C-terminal to N-terminal direction of a constant light chain domain (CL) of kappa isotype and a variable heavy chain domain ($VH_1$) derived from an antibody, which specifically binds to a first antigen; and
  c) a second modified light chain consists in C-terminal to N-terminal direction of a constant light chain domain (CL) of lambda isotype and a variable heavy chain domain ($VH_2$) derived from an antibody, which specifically binds to a second antigen.
13. A method for the preparation of a multispecific antibody according to any one of the preceding embodiments, comprising the steps of
  a) transforming a host cell with expression vectors comprising nucleic acid molecules encoding a multispecific antibody according to any one of the preceding embodiments;
  b) culturing the host cell under conditions that allow synthesis of said multispecific antibody molecule; and
  c) recovering said multispecific antibody molecule from said culture.
14. The method according to embodiment 13, wherein the host cell is transformed with three different expression vectors, wherein a first expression vector comprises nucleic acid molecules encoding for the modified light chain comprising the constant light chain domain of kappa isotype, wherein a second expression vector comprises nucleic acid molecules encoding for the modified light chain comprising the constant light chain domain of lambda isotype, and wherein a third expression vector comprises nucleic acid molecules encoding for the modified heavy chain.
15. A nucleic acid encoding a light chain of an antibody according to any one of embodiments 1 to 12.
16. A nucleic acid encoding the heavy chain of an antibody according to any one of embodiments 1 to 12.
17. A nucleic acid encoding the multispecific antibody according to any one of embodiments 1 to 12.
18. An expression vector comprising a nucleic acid according to any one of embodiments 15 to 17.
19. An expression vector of embodiment 18 capable of expressing said nucleic acid in a prokaryotic or eukaryotic host cell.
20. A host cell comprising an expression vector according to embodiment 18 or 19.
21. The host cell of embodiment 20, wherein the host cell comprises three different expression vectors, wherein a first expression vector comprises nucleic acid molecules encoding for the modified light chain comprising the constant light chain domain of kappa isotype, wherein a second expression vector comprises nucleic acid molecules encoding for the modified light chain comprising the constant light chain domain of lambda isotype, and wherein a third expression vector comprises nucleic acid molecules encoding for the modified heavy chain.
22. The host cell according to embodiment 20 or 21, wherein the host cell is eukaryotic or prokaryotic.
23. The host cell according to embodiment 20 or 21, wherein the host cell is eukaryotic.
24. The host cell according to embodiment 20 or 21, wherein the host cell is prokaryotic.
25. A method for the generation of a multispecific antibody based on a first antibody, which specifically binds to a first antigen, and a second antibody, which specifically binds to a second antigen, wherein the first antibody and the second antibody comprise a common light chain, comprising the steps of
  a) modifying the light chain derived from said first antibody to obtain a light chain comprising in C-terminal to N-terminal direction a constant light chain domain of kappa isotype and a heavy chain variable domain ($VH_1$) by replacing the light chain variable domain (VL) by the heavy chain variable domain ($VH_1$) of the heavy chain derived from said first antibody and, optionally, replacing the original constant light chain domain by a constant light chain domain of kappa isotype;
  b) modifying the light chain derived from said second antibody to obtain a light chain comprising in C-terminal to N-terminal direction a constant light chain domain of lambda isotype and a heavy chain variable domain ($VH_2$) by replacing the light chain variable domain (VL) by the heavy chain variable domain ($VH_2$) of the heavy chain derived from said second antibody and, optionally, replacing the original constant light chain domain by a constant light chain domain of lambda isotype;
  c) modifying the heavy chain derived from said first antibody in order to obtain a heavy chain comprising in C-terminal to N-terminal direction heavy chain constant domains 3, 2 and 1 (CH3, CH2 and CH1) and a light chain variable domain (VL) by replacing the heavy chain variable domain ($VH_1$) by the light chain variable domain (VL) of the light chain derived from said first antibody, and/or modifying the heavy chain derived from said second antibody in order to obtain a heavy chain comprising in C-terminal to N-terminal direction heavy chain constant domains 3, 2 and 1 (CH3, CH2 and CH1) and a light chain variable domain (VL) by replacing the heavy chain variable domain (VH₂) by the light chain variable domain (VL) of the light chain derived from said second antibody.

26. The method of embodiment 25 for the generation of a multispecific antibody according to any one of embodiments 1 to 12.
27. A multispecific antibody obtained by the method according to embodiment 25 or 26.
28. A pharmaceutical composition comprising the multispecific antibody according to any one of embodiments 1 to 12 and 26 in combination with at least one pharmaceutically acceptable excipient.
29. The pharmaceutical composition according to embodiment 28, wherein the composition comprises a therapeutically effective amount of the multispecific antibody.
30. The multispecific antibody according to any one of embodiments 1 to 12 and 26 for use as a medicament.
31. The multispecific antibody according to any one of embodiments 1 to 12 and 26 for use in the treatment of cancer.
32. The pharmaceutical composition according to embodiment 28 or 29 for use as a medicament.
33. The pharmaceutical composition according to embodiment 28 or 29 for use in the treatment of cancer.
34. Use of the multispecific antibody according to any one of embodiments 1 to 12 and 26 for the manufacture of a medicament.
35. Use of the multispecific antibody according to any one of embodiments 1 to 12 and 26 for the manufacture of a medicament for the treatment of cancer.
36. A method for the treatment of a patient in need of therapy, characterized by administering to the patient a therapeutically effective amount of a multispecific antibody according to any one of embodiments 1 to 12 and 26.
37. A method for the treatment of a cancer patient in need of therapy, characterized by administering to the patient a therapeutically effective amount of a multispecific antibody according to any one of embodiments 1 to 12 and 26.

Description of the Sequences

SEQ ID NO: 1 nucleotide sequence of modified heavy chain CH3-CH2-CH1-VL, wherein VL is a variable domain of a common light chain (CLC-Fc cross-Mab)

SEQ ID NO: 2 nucleotide sequence of modified light chain comprising a polypeptide consisting of CLκ-VH₁-CLκ wherein VH₁ is the variable heavy chain domain from an antibody which binds to a first antigen ([anti-DR5 2A11 VH₁]-CLκ)

SEQ ID NO: 3 nucleotide sequence of modified light chain comprising a polypeptide consisting of CLκ-VH₁-CLκ wherein VH₁ is the variable heavy chain domain from an antibody which binds to a first antigen ([anti-DR5 8E11 VH₁]-CLκ)

SEQ ID NO: 4 nucleotide sequence of modified light chain comprising a polypeptide consisting of CLκ-VH₁-CLκ wherein VH₁ is the variable heavy chain domain from an antibody which binds to a first antigen ([anti-DR5 21C11 VH₁]-CLκ)

SEQ ID NO: 5 nucleotide sequence of modified light chain VH₂—CLλ wherein VH₂ is the variable heavy chain domain from an antibody which binds to a second antigen ([anti-FAP 3C6 VH₂]-CLλ)

SEQ ID NO: 6 amino acid sequence of modified heavy chain CH3-CH2-CH1-VL, wherein VL is a variable domain of a common light chain (CLC-Fc cross-Mab)

SEQ ID NO: 7 amino acid sequence of modified light chain comprising a polypeptide consisting of CLκ-VH₁-CLκ wherein VH₁ is the variable heavy chain domain from an antibody which binds to a first antigen ([anti-DR5 2A11 VH₁]-CLκ)

SEQ ID NO: 8 amino acid sequence of modified light chain comprising a polypeptide consisting of CLκ-VH₁-CLκ wherein VH₁ is the variable heavy chain domain from an antibody which binds to a first antigen ([anti-DR5 8E11 VH₁]-CLκ)

SEQ ID NO: 9 amino acid sequence of modified light chain comprising a polypeptide consisting of CLκ-VH₁-CLκ wherein VH₁ is the variable heavy chain domain from an antibody which binds to a first antigen ([anti-DR5 21C11 VH₁]-CLκ)

SEQ ID NO: 10 amino acid sequence of modified light chain VH₂-CLλ wherein VH₂ is the variable heavy chain domain from an antibody which binds to a second antigen ([anti-FAP 3C6 VH₂]-CLλ)

Example 1

Generation of the Common Light Chain Library (CLCL) and Binder Generation

A library for phage display was generated that has all of its diversity located in the heavy chain. The light chain was chosen from an existing antibody from a previous humanization project (humanized Light Chain ML1 of anti-MCSP antibody LC007 described in WO 2013/026832 (LC007 humanized antibody ML1 VL)).

Two different heavy chains were chosen to be included in this library. The first one is DP47 and the other one is DP88 (IMGT Acc Nos: IGHV3-23*01, and IGHV1-69*06, respectively). J-elements were: JH4 (FDYWGQGTLVTVSS (SEQ ID NO: 11)) and JH6 (MDAWGQGTTVTVSS (SEQ ID NO: 12)), respectively. The CDR3s of the two heavy chains were diversified using randomization primers based on trinucleotide building blocks as described (Virnekas et al.; Nucleic Acids Res. 1994 Dec. 25; 22(25):5600-7.) The lengths of the CDR3 loops in both libraries were either 4, 6, or 8 amino acids in lengths for that stretch corresponding to the D-element (amino acids 95-98, 95-100, or 95-100b. The antibody library was cloned in the Fab format in the conventional M13 phage display system (de Haard et al.; Journal of Biological Chemistry Volume 274, Issue 26, 25 Jun. 1999, Pages 18218-18230).

Phage panning was performed on recombinant FAP and DR5 protein after biotinylation and immobilization on streptavidin beads. Binding was confirmed after selection by ELISA and positive clones were sequenced by classical didesoxy sequencing before conversion into IgG or Cross-Mab format.

Example 2

Generation of a Bispecific Modified Common Light Chain DR5/FAP-Kappa-Lambda Antibody To generate a bispecific antibody (monovalent for each antigen) that simultaneously can bind to two different antigens without using any heterodimerization approach (e.g. knob-into-hole technology), a combination of a common light chain library with the so-called CrossMab technology was applied: The variable region of a common light chain (CLC) was fused to the CH1 domain of a standard human IgG1 antibody to form the VL/VH crossed molecule (fused to Fc) which is common for both specificities. To generate the crossed counterparts (VH-CL), a variable heavy chain domain specific for antigen A (isolated from a common light chain library) was fused to a constant human k light chain whereas a variable heavy chain domain specific for antigen B (also isolated from common light chain library) was fused to a constant human 1 light chain. This enables the purification of the desired bispecific antibody by applying subsequent purification steps with KappaSelect and LambdaFab Select columns (GE Healthcare) to remove undesired homodimeric antibodies.

For proof of concept, to see if these molecules can be produced in active form, antibodies directed against human death receptor 5 (TRAIL-R2) and human fibroblast activation protein (FAP) were combined to a bispecific antibody with a 1+1 valency.

In a first construct the DR5 binder 2A11 was combined with the FAP binder 3C6. After having shown that this molecule can bind to both antigens and is active in an apoptosis induction assay, two more DR5-FAP bispecific constructs were generated as described above: here the FAP binder 3C6 was fused to different DR5 binders isolated from the common light chain library (i.e. 8E11 and 21C11). These bispecific antibodies according to the invention specifically binding DR5 and FAP are further also referred to as "bispecific modified common light chain DR5/FAP-kappa-lambda antibodies".

All antibody expression vectors were generated using standard recombinant DNA technology as described in Sambrook, J. et al., Molecular cloning: A laboratory manual; Cold Spring Harbor Laboratory Press, Cold Spring Harbor, N.Y., 1989. Molecular biological reagents were used according to the manufacturer's recommendations. Genes or gene fragments were either amplified by polymerase chain reaction (PCR) or generated from synthetic oligonucleotides at Geneart AG (Regensburg, Germany) by automated gene synthesis. PCR-amplified or subcloned DNA fragments were confirmed by DNA sequencing (Synergene GmbH, Switzerland). Plasmid DNA was transformed into and amplified in suitable *E. coli* host strains for preparation of transfection-grade plasmid DNA using standard Maxiprep kits (Qiagen). For production of the bispecific molecules HEK293 EBNA cells were transfected with plasmids encoding the respective genes using a standard polyethlenimine (PEI) based method. The used plasmid ratio of the three expression vectors was 1:1:1. Transfected cells were cultivated for 7 days before supernatants were harvested for purification.

TABLE 2

Nucleotide sequences of bispecific modified common light chain DR5/FAP-kappa-lambda antibodies

| Construct | DNA sequence | Seq. ID No. |
|---|---|---|
| modified heavy chain [CH3-CH2-CH1-VL], wherein VL is a variable domain of a common light chain (CLC-Fc cross-Mab) (including signal sequence) | ATGGGATGGAGCTGTATCATCCTCTTCTTGGTAGCA ACAGCTACCGGTGTGCATTCCGACATCCAGATGACC CAGAGCCCCAGCAGCCTGAGCGCCAGCGTGGGCGAC AGAGTGACCATCACCTGCAGCGCCAGCCAGGGCATC CGGAACTACCTGAACTGGTATCAGCAGAAGCCCGGC AAGGCCCCCAAGCTGCTGATCTACTACACCAGCAGC CTGCACAGCGGCGTGCCTAGCCGGTTTAGCGGCAGC GGCTCCGGCACCGACTTCACCCTGACCATTAGCTCC CTGCAGCCCGAGGACTTCGCCACCTACTACTGCCAG CAGTACAGCAAGCTGCCCTGGACCTTCGGCCAGGGA ACAAAGGTGGAGATCAAGAGCTCCGCTAGCACCAAG GGCCCATCGGTCTTCCCCCTGGCACCCTCCTCCAAG AGCACCTCTGGGGGCACAGCGGCCCTGGGCTGCCTG GTCAAGGACTACTTCCCCGAACCGGTGACGGTGTCG TGGAACTCAGGCGCCCTGACCAGCGGCGTGCACACC TTCCCGGCTGTCCTACAGTCCTCAGGACTCTACTCC CTCAGCAGCGTGGTGACCGTGCCCTCCAGCAGCTTG GGCACCCAGACCTACATCTGCAACGTGAATCACAAG CCCAGCAACACCAAGGTGGACAAGAAAGTTGAGCCC AAATCTTGTGACAAAACTCACACATGCCCACCGTGC CCAGCACCTGAACTCCTGGGGGGACCGTCAGTCTTC CTCTTCCCCCCAAAACCCAAGGACACCCTCATGATC TCCCGGACCCCTGAGGTCACATGCGTGGTGGTGGAC GTGAGCCACGAAGACCCTGAGGTCAAGTTCAACTGG TACGTGGACGGCGTGGAGGTGCATAATGCCAAGACA AAGCCGCGGGAGGAGCAGTACAACAGCACGTACCGT GTGGTCAGCGTCCTCACCGTCCTGCACCAGGACTGG CTGAATGGCAAGGAGTACAAGTGCAAGGTCTCCAAC AAAGCCCTCCCAGCCCCCATCGAGAAAACCATCTCC AAAGCCAAAGGGCAGCCCCGAGAACCACAGGTGTAC ACCCTGCCCCCATCCCGGGATGAGCTGACCAAGAAC CAGGTCAGCCTGACCTGCCTGGTCAAAGGCTTCTAT CCCAGCGACATCGCCGTGGAGTGGGAGAGCAATGGG CAGCCGGAGAACAACTACAAGACCACGCCTCCCGTG CTGGACTCCGACGGCTCCTTCTTCCTCTACAGCAAG CTCACCGTGGACAAGAGCAGGTGGCAGCAGGGGAAC GTCTTCTCATGCTCCGTGATGCATGAGGCTCTGCAC AACCACTACACGCAGAAGAGCCTCTCCCTGTCTCCG GGTAAA | 1 |
| modified light chain [CLκ-VH₁-CLκ], wherein VH₁ is the variable heavy chain domain from an antibody which binds to a first | ATGGGCTGGAGCTGCATCATCCTGTTCCTGGTGGCC ACCGCCACCGGCGTGCATTCCGAGGTGCAGCTGCTG GAGAGCGGCGGCGGCCTGGTGCAGCCCGGCGGCAGC CTGAGGCTGAGCTGCGCCGCCAGCGGCTTCACCTTC | 2 |

TABLE 2-continued

Nucleotide sequences of bispecific modified common light chain DR5/FAP-kappa-lambda antibodies

| Construct | DNA sequence | Seq. ID No. |
|---|---|---|
| antigen (anti-DR5 2A11) (including signal sequence) | AGCAGCTACGCCATGAGCTGGGTGAGGCAGGCCCCC<br>GGCAAGGGCCTGGAGTGGGTGAGCGCCATCAGCGGC<br>AGCGGCGGCAGCACCTACTACGCCGACAGCGTGAAG<br>GGCAGGTTCACCATCAGCAGGGACAACAGCAAGAAC<br>ACCCTGTACCTGCAGATGAACAGCCTGAGGGCCGAG<br>GACACCGCCGTGTACTACTGCGCCAGGGGCCCCTAC<br>GGCAGGTACGCCGCCCTGGACTACTGGGGCCAGGGC<br>ACCCTGGTGACCGTGAGCAGCGCTAGCGTGGCCGCT<br>CCCAGCGTGTTCATCTTCCCACCCAGCGACGAGCAG<br>CTGAAGTCCGGCACAGCCAGCGTGGTGTGCCTGCTG<br>AACAACTTCTACCCCCGCGAGGCCAAGGTGCAGTGG<br>AAGGTGGACAACGCCCTGCAGAGCGGCAACAGCCAG<br>GAATCCGTGACCGAGCAGGACAGCAAGGACTCCACC<br>TACAGCCTGAGCAGCACCCTGACCCTGAGCAAGGCC<br>GACTACGAGAAGCACAAGGTGTACGCCTGCGAAGTG<br>ACCCACCAGGGCCTGTCCAGCCCCGTGACCAAGAGC<br>TTCAACCGGGGCGAGTGC | |
| modified light chain [CLκ-VH₁-CLκ], wherein VH₁ is the variable heavy chain domain from an antibody which binds to a first antigen (anti-DR5 8E11) (including signal sequence) | ATGGGCTGGAGCTGCATCATCCTGTTCCTGGTGGCC<br>ACCGCCACCGGCGTGCATTCCGAGGTGCAATTGTTG<br>GAGTCTGGGGGAGGCTTGGTACAGCCTGGGGGGTCC<br>CTGAGACTCTCCTGTGCAGCCTCCGGATTCACCTTT<br>AGCAGTTATGCCATGAGCTGGGTCCGCCAGGCTCCA<br>GGGAAGGGGCTGGAGTGGGTCTCAGCTATTAGTGGT<br>AGTGGTGGTAGCACATACTACGCAGACTCCGTGAAG<br>GGCCGGTTCACCATCTCCAGAGACAATTCCAAGAAC<br>ACGCTGTATCTGCAGATGAACAGCCTGAGAGCCGAG<br>GACACGGCCGTATATTACTGTGCGAAAGACTCTTCT<br>TCTTGGTACTCCTACGCTTTCGACTACTGGGGCCAA<br>GGAACCCTGGTCACCGTCTCGAGTGCTAGCGTGGCC<br>GCTCCCAGCGTGTTCATCTTCCCACCCAGCGACGAG<br>CAGCTGAAGTCCGGCACAGCCAGCGTGGTGTGCCTG<br>CTGAACAACTTCTACCCCCGCGAGGCCAAGGTGCAG<br>TGGAAGGTGGACAACGCCCTGCAGAGCGGCAACAGC<br>CAGGAATCCGTGACCGAGCAGGACAGCAAGGACTCC<br>ACCTACAGCCTGAGCAGCACCCTGACCCTGAGCAAG<br>GCCGACTACGAGAAGCACAAGGTGTACGCCTGCGAA<br>GTGACCCACCAGGGCCTGTCCAGCCCCGTGACCAAG<br>AGCTTCAACCGGGGCGAGTGCTGA | 3 |
| modified light chain [CLκ-VH₁-CLκ], wherein VH₁ is the variable heavy chain domain from an antibody which binds to a first antigen (anti-DR5 21C11) (including signal sequence) | ATGGGCTGGAGCTGCATCATCCTGTTCCTGGTGGCC<br>ACCGCCACCGGCGTGCATTCCCAGGTGCAATTGGTG<br>CAGTCTGGGGCTGAGGTGAAGAAGCCTGGGTCCTCG<br>GTGAAGGTCTCCTGCAAGGCCTCCGGAGGCACATTC<br>AGCAGCTACGCTATAAGCTGGGTGCGACAGGCCCCT<br>GGACAAGGGCTCGAGTGGATGGGAAGGATCATCCCT<br>ATCTTTGGTACAGCAAACTACGCACAGAAGTTCCAG<br>GGCAGGGTCACCATTACTGCAGACAAATCCACGAGC<br>ACAGCCTACATGGAGCTGAGCAGCCTGAGATCTGAG<br>GACACCGCCGTGTATTACTGTGCGAGAGAAGGTTTC<br>TACATCGACTACTGGGGCCAAGGGACCACCGTGACC<br>GTCTCCTCAGCTAGCGTGGCCGCTCCCAGCGTGTTC<br>ATCTTCCCACCCAGCGACGAGCAGCTGAAGTCCGGC<br>ACAGCCAGCGTGGTGTGCCTGCTGAACAACTTCTAC<br>CCCCGCGAGGCCAAGGTGCAGTGGAAGGTGGACAAC<br>GCCCTGCAGAGCGGCAACAGCCAGGAATCCGTGACC<br>GAGCAGGACAGCAAGGACTCCACCTACAGCCTGAGC<br>AGCACCCTGACCCTGAGCAAGGCCGACTACGAGAAG<br>CACAAGGTGTACGCCTGCGAAGTGACCCACCAGGGC<br>CTGTCCAGCCCCGTGACCAAGAGCTTCAACCGGGGC<br>GAGTGCTGA | 4 |
| modified light chain [VH₂-CLλ], wherein VH₂ is the variable heavy chain domain from an antibody which binds to a second antigen (anti-FAP 3C6) (including signal sequence) | ATGGGATGGAGCTGTATCATCCTCTTCTTGGTAGCA<br>ACAGCTACCGGTGTGCATTCCGAGGTGCAGCTGCTG<br>GAGAGCGGCGGCGGCCTGGTGCAGCCCGGCGGCAGC<br>CTGAGGCTGAGCTGCGCCGCCAGCGGCTTCACCTTC<br>AGCAGCTACGCCATGAGCTGGGTGAGGCAGGCCCCC<br>GGCAAGGGCCTGGAGTGGGTGAGCGCCATCAGCGGC<br>AGCGGCGGCAGCACCTACTACGCCGACAGCGTGAAG<br>GGCAGGTTCACCATCAGCAGGGACAACAGCAAGAAC<br>ACCCTGTACCTGCAGATGAACAGCCTGAGGGCCGAG<br>GACACCGCCGTGTACTACTGCGCCAAGAGCGTGGTG<br>TACAGCTACGACCCCGGCTTCGACTACTGGGGCCAG<br>GGCACCCTGGTGACCGTGTCCGGACAGCCCAAGGCC | 5 |

TABLE 2-continued

Nucleotide sequences of bispecific modified common light chain DR5/FAP-kappa-lambda antibodies

| Construct | DNA sequence | Seq. ID No. |
|---|---|---|
| | GCCCCCAGCGTGACCCTGTTCCCCCCCAGCAGCGAG GAGCTGCAGGCCAACAAGGCCACCCTGGTGTGCCTG ATCAGCGACTTCTACCCCGGCGCCGTGACCGTGGCC TGGAAGGCCGACAGCAGCCCCGTGAAGGCCGGCGTG GAGACCACCACCCCCAGCAAGCAGAGCAACAACAAG TACGCCGCCAGCAGCTACCTGAGCCTGACCCCCGAG CAGTGGAAGAGCCACAGGAGCTACAGCTGCCAGGTG ACCCACGAGGGCAGCACCGTGGAGAAGACCGTGGCC CCCACCGAGTGCAGC | |

TABLE 3 of bispecific modified common light chain DR5/FAP-kappa-lambda antibodies

| Construct | Sequence | Seq. ID No. |
|---|---|---|
| modified heavy chain [CH3-CH2-CH1-VL], wherein VL is a variable domain of a common light chain (CLC-Fc cross-Mab); italic ... signal sequence underlined ... common light chain variable domain VL bold ... CH1 to CH3 domains | *MGWSCIILFLVATATGVHS*<u>DIQMTQSPS SLSASVGDRVTITCSASQGIRNYLNWYQ QKPGKAPKLLIYYTSSLHSGVPSRFSGS GSGTDFTLTISSLQPEDFATYYCQQYSK LPWTFGQGTKVEIKSS</u>ASTKGPSVFPLA PSSKSTSGGTAALGCLVKDYFPEPVTVS WNSGALTSGVHTFPAVLQSSGLYSLSSV VTVPSSSLGTQTYICNVNHKPSNTKVDK KVEPKSCDKTHTCPPCPAPELLGGPSVF LFPPKPKDTLMISRTPEVTCVVVDVSHE DPEVKFNWYVDGVEVHNAKTKPREEQYN STYRVVSVLTVLHQDWLNGKEYKCKVSN KALPAPIEKTISKAKGQPREPQVYTLPP SRDELTKNQVSLTCLVKGFYPSDIAVEW ESNGQPENNYKTTPPVLDSDGSFFLYSK LTVDKSRWQQGNVFSCSVMHEALHNHYT QKSLSLSPGK | 6 |
| modified light chain [CLκ-VH₁-CLκ], wherein VH₁ is the variable heavy chain domain from an antibody which binds to a first antigen (anti-DR5 2A11); italic ... signal sequence underlined ... VH₁ domain of anti-DR5 2A11 bold ... CLκ | *MGWSCIILFLVATATGVHS*<u>EVQLLESGG GLVQPGGSLRLSCAASGFTFSSYAMSWV RQAPGKGLEWVSAISGSGGSTYYADSVK GRFTISRDNSKNTLYLQMNSLRAEDTAV YYCARGPYGRYAALDYWGQGTLVTVSSA</u>SVAAPSVFIFPPSDEQLKSGTASVVCLL NNFYPREAKVQWKVDNALQSGNSQESVT EQDSKDSTYSLSSTLTLSKADYEKHKVY ACEVTHQGLSSPVTKSFNRGEC | 7 |
| modified light chain [CLκ-VH₁-CLκ], wherein VH₁ is the variable heavy chain domain from an antibody which binds to a first antigen (anti-DR5 8E11); italic ... signal sequence underlined ... VH₁ domain of anti-DR5 8E11 bold ... CLκ | *MGWSCIILFLVATATGVHS*<u>EVQLLESGG GLVQPGGSLRLSCAASGFTFSSYAMSWV RQAPGKGLEWVSAISGSGGSTYYADSVK GRFTISRDNSKNTLYLQMNSLRAEDTAV YYCAKDSSSWYSYAPDYWGQGTLVTVSS A</u>SVAAPSVFIFPPSDEQLKSGTASVVCL LNNFYPREAKVQWKVDNALQSGNSQESV TEQDSKDSTYSLSSTLTLSKADYEKHKV YACEVTHQGLSSPVTKSFNRGEC | 8 |
| modified light chain [CLκ-VH₁-CLκ], wherein VH₁ is the variable heavy chain domain from an an which binds to a first antigen (anti-DR5 21C11); italic ... signal sequence underlined ... VH₁ domain of anti-DR5 21C11 bold ... CLκ | *MGWSCIILFLVATATGVHS*<u>QVQLVQSGA EVKKPGSSVKVSCKASGGTFSSYAISWV RQAPGQGLEWMGRIIPIFGTANYAQKFQ GRVTITADKSTSTAYMELSSLRSEDTAV YYCAREGFYIDYWGQGTTVTVSS</u>ASVAA PSVFIFPPSDEQLKSGTASVVCLLNNFY PREAKVQWKVDNALQSGNSQESVTEQDS KDSTYSLSSTLTLSKADYEKHKVYACEV THQGLSSPVTKSFNRGEC | 9 |
| modified light chain [VH₂-CLλ], wherein VH₂ is the variable heavy chain domain from an an which binds to a second antigen (anti-FAP 3C6); italic ... signal sequence underlined ... VH₂ domain of anti-FAP 3C6 bold ... CLλ | *MGWSCIILFLVATATGVHS*<u>EVQLLESGG GLVQPGGSLRLSCAASGFTFSSYAMSWV RQAPGKGLEWVSAISGSGGSTYYADSVK GRFTISRDNSKNTLYLQMNSLRAEDTAV YYCAKSVVYSYDPGFDYWGQGTLVTVSG</u>QPKAAPSVTLFPPSSEELQANKATLVCL ISDFYPGAVTVAWKADSSPVKAGVETTT PSKQSNNKYAASSYLSLTPEQWKSHRSY SCQVTHEGSTVEKTVAPTECS | 10 |

Accordingly, the following three bispecific antibodies according to the invention specifically binding to DR5 and FAP were generated:

TABLE 4 bispecific modified common light chain DR5/FAP - kappa - lambda antibodies

| GA803_G25_H14D_001 | kappa light chain based on anti-DR5 2A11 VH₁ (SEQ ID NO: 7) and lambda light chain based on anti-FAP 3C6 VH₂ (SEQ ID NO: 10) and heavy chain including common light chain variable domain (SEQ ID NO: 6) |
| GA803_G27_H14D_001 | kappa light chain based on anti-DR5 8E11 VH₁ (SEQ ID NO: 8) and lambda light chain based on anti-FAP 3C6 VH₂ (SEQ ID NO: 10) and heavy chain including common light chain variable domain (SEQ ID NO: 6) |

TABLE 4-continued bispecific modified common light chain
DR5/FAP - kappa - lambda antibodies

| | |
|---|---|
| GA803_G28_H14D_001 | kappa light chain based on anti-DR5 21C11 $VH_1$ (SEQ ID NO: 9) and lambda light chain based on anti-FAP 3C6 $VH_2$ (SEQ ID NO: 10) and heavy chain including common light chain variable domain (SEQ ID NO: 6) |

Figure 2A:
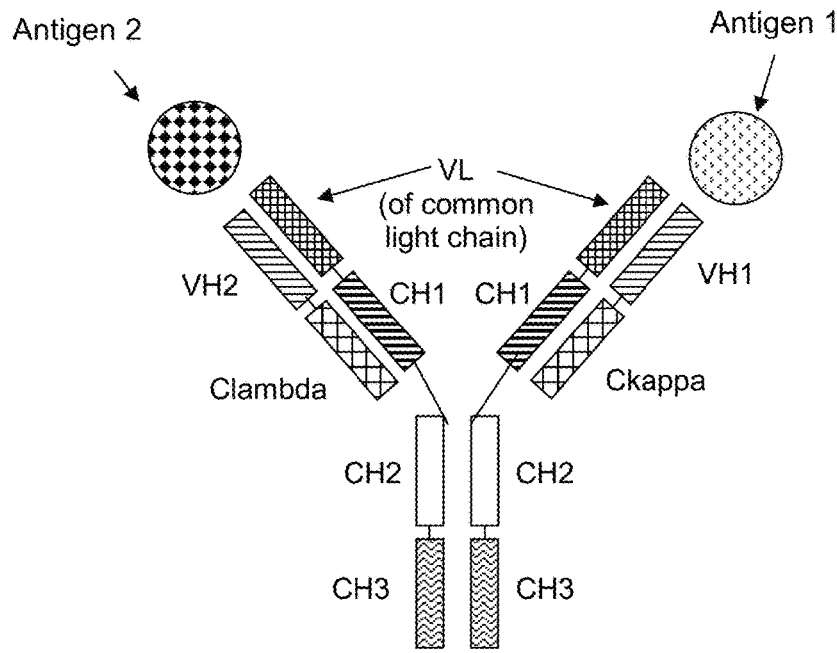
FIG. 2A A schematic illustration of a bispecific antibody of the invention, which specifically binds to two different antigens (antigen 1 and antigen 2) based on two antibodies comprising a common light chain. By a domain exchange between the heavy chain and light chain variable domain the heavy chains of the bispecific antibody include the VL domain of the common light chain. The antibody comprises two different light chains, wherein one light chain includes the respective variable heavy chain domain, which specifically binds to antigen 2, and the constant light chain domain of lambda isotype; and wherein the other light chain includes the respective variable heavy chain domain, which specifically binds to antigen 1, and the constant light chain domain of kappa isotype. The variable and constant domains of the heavy chain and the two different light chains are indicated.
Figure 2B:
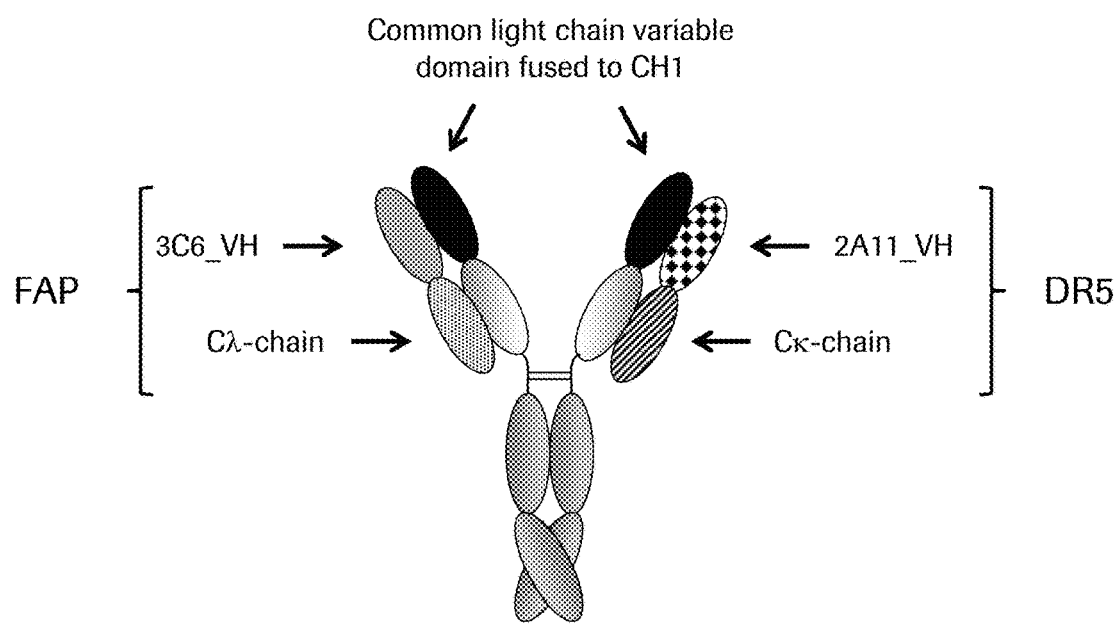
FIG. 2B A schematic illustration of a bispecific antibody according to the invention, which specifically binds to FAP and DR5. Within said antibody, the variable heavy chain domain ($VH_2$) from an anti-FAP (3C6) antibody is coupled to a constant light chain domain of lambda isotype in order to form a first modified light chain; and the variable heavy chain domain ($VH_1$) from an anti-DR5 (2A11) antibody is coupled to a constant light chain domain of kappa isotype in order to form a second modified light chain. Targeting moieties and respective light chain domains are indicated. Bispecific antibodies, wherein the VH from the anti-FAP (3C6) antibody is coupled to a CLλ domain and either the VH from an anti-DR5 (8E11) antibody or the VH from an anti-DR5 (21C11) antibody is coupled to a CLκ domain, were generated analogously, but are not depicted separately.

A schematic drawing of the architecture of the bispecific modified common light chain-kappa-lambda antibodies is shown in FIG. 2A. Variable and constant domains of the two identical modified heavy chains and the two different modified light chains are indicated. In FIG. 2B a schematic drawing of the bispecific kappa-lambda antibodies is shown for the antibody GA803_G25_H14D_001 (based on anti-DR5 2A11 and anti-FAP 3C6) as an example. Targeting moieties and respective light chain domains are indicated. The combinations of 3C6 with 8E11 and 21C11 were generated with an analogue domain architecture.

Example 3

Expression and Purification of a Bispecific Modified Common Light Chain DR5/FAP-Kappa-Lambda Antibody The molecule is produced by co-transfecting HEK293-EBNA cells growing in suspension with the mammalian expression vectors using polyethylenimine. The cells are transfected with the corresponding expression vectors in a 1:1:2 ratio ("vector modified $VH_1$-kappa light chain ((DR5-CLκ)": "vector modified $VH_2$-lambda light chain (FAP-CLλ)": "vector modified heavy chain with common light chain VL (CLC-Fc cross-Mab)").

HEK293-EBNA cells are cultivated in suspension serum free in CD CHO culture medium. For the production in 500 ml shake flask 400 million HEK293-EBNA cells are seeded 24 hours before transfection. For transfection cells are centrifuged for 5 min by 210×g, supernatant is replaced by pre-warmed 20 ml CD CHO medium. Expression vectors are mixed in 20 ml CD CHO medium to a final amount of 200 µg DNA. After addition of 540 µl PEI solution is vortexed for 15 s and subsequently incubated for 10 min at room temperature. Afterwards cells are mixed with the DNA/PEI solution, transferred to a 500 ml shake flask and incubated for 3 hours by 37° C. in an incubator with a 5% CO2 atmosphere. After incubation time 160 ml F17 medium is added and cell are cultivated for 24 hours. One day after transfection 1 mM valporic acid and 7% Feed 1 is added. After 7 days cultivation supernatant is collected for purification by centrifugation for 15 min at 210×g, the solution is sterile filtered (0.22 µm filter) and sodium azide in a final concentration of 0.01% w/v is added, and kept at 4° C.

The secreted protein is purified from cell culture supernatants by two sequential affinity chromatography steps using kappa light chain and lambda light chain affinity chromatography, followed by a size exclusion chromatographic step.

For first affinity chromatography step supernatant is loaded on a Capture Select Kappa affinity matrix (BAC) packed in a Tricorn 5/50 column (CV=1 mL, GE Healthcare) and equilibrated with 5 ml 50 mM TRIS, 100 mM glycine, 150 mM NaCl, pH 8.0. Unbound protein is removed by washing with at least 15 column volume 50 mM TRIS, 100 mM glycine, 150 mM NaCl, pH 8.0. Target protein is eluted in a step pH-gradient over 25 column volume to 50 mM TRIS, 100 mM glycine, 150 mM NaCl, pH 2.0.

Eluate from first purification step is neutralized by diluting 1:1 into 50 mM TRIS, 100 mM glycine, 150 mM NaCl, pH 8.0.

Second affinity chromatography step is done on a Capture Select Lambda affinity matrix (BAC) packed in a Tricorn 5/50 column (CV=1 mL, GE Healthcare) and equilibrated with 5 ml 50 mM TRIS, 100 mM glycine, 150 mM NaCl, pH 8.0. After loading, column is washed with at least 15 column volume 50 mM TRIS, 100 mM glycine, 150 mM NaCl, pH 8.0. By lowering the pH to pH2.0 in a step pH-gradient target protein is eluted from column. Fractions from Capture Select Lambda affinity column are pooled and concentrated using spin concentrator (Amicon MWCO: 30.000 Da). Thereby buffer is exchanged to 20 mM Histidine, 140 mM sodium chloride solution of pH 6.0.

Concentrated protein solution is subsequently loaded on a Superdex 200 10/300GL column (GE Healthcare) equilibrated with 20 mM Histidine, 140 mM sodium chloride solution of pH 6.0.

Example 4

Characterization of the Bispecific Modified Common Light Chain DR5/FAP-Kappa-Lambda Antibodies The protein concentration of purified protein samples is determined by measuring the optical density (OD) at 280 nm, using the molar extinction coefficient calculated on the basis of the amino acid sequence.

Figure 3:
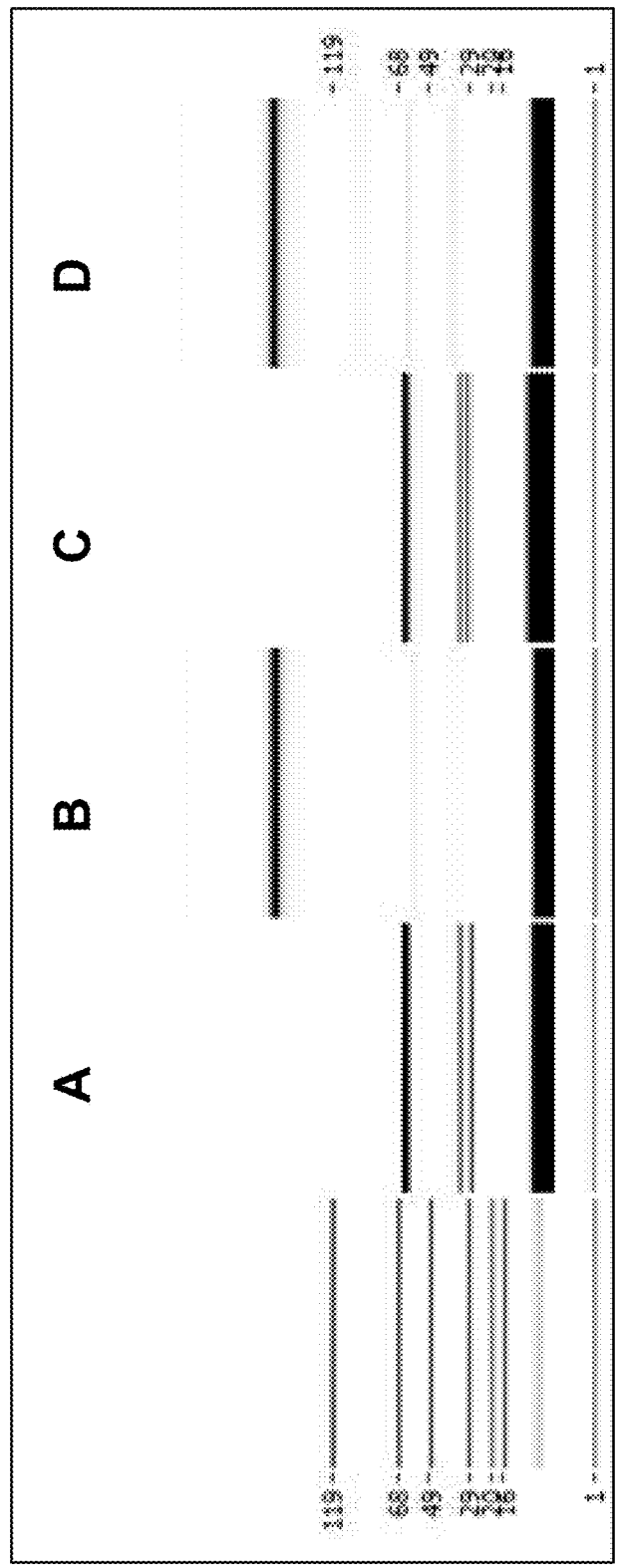
FIG. 3 Purity and molecular weight of bispecific antibodies according to the invention specifically binding to FAP and DR5 were analyzed by CE-SDS analyses under reducing and non-reducing conditions. The electropherogram is shown as SDS-Page of following bispecific antibodies:
A)<FAP(3C6)[CLλ]-DR5(8E11)[CLκ]> (reduced),
B)<FAP(3C6)[CLλ]-DR5(8E11)[CLκ]> (non reduced),
C) <FAP(3C6)[CLλ]-DR5(21C11)[CLκ]> (reduced),
D)<FAP(3C6) [CLλ]-DR5(21C11)[CLκ]> (non reduced).

Purity and molecular weight of molecules are analyzed by CE-SDS analyses in the presence and absence of a reducing agent. The Caliper LabChip GXII system (Caliper lifescience) is used according to the manufacturer's instruction. 2 ug sample is used for analyses. The electropherogram is shown as SDS-Page of the bispecific modified common light chain DR5/FAP-kappa-lambda antibody: A) 3C6/8E11 (reduced), B) 3C6/8E11 (non reduced) C) 3C6/21C11 (reduced), D) 3C6/21C11 (non reduced) (results are shown in FIG. 3).

The aggregate content of antibody samples is analyzed using a TSKgel G3000 SW XL analytical size-exclusion column (Tosoh) in 25 mM K2HPO4, 125 mM NaCl, 200 mM L-Arginine Monohydrocloride, 0.02% (w/v) NaN3, pH 6.7 running buffer at 25° C.

A molecule consisting of a common heavy chain with a kappa as well as lambda light chain can be homogeneously purified by two sequential affinity chromatography steps. The final monomer content of the preparation is listed in table 5.

TABLE 5

Yield and final monomer content of bispecific modified
common light chain DR5/FAP - kappa - lambda antibody

| bispecific modified common light chain DR5/FAP - kappa - lambda antibody | Yield [mg/l] | HMW [%] | LMW [%] | Monomer [%] |
|---|---|---|---|---|
| 3C6/8E11 | 0.72 | 5 | 6 | 89 |
| 3C6/21C11 | 0.44 | 3.4 | 3.2 | 93.4 |

LC-MS Analyses of the Bispecific Modified Common Light Chain DR5/FAP-Kappa-Lambda Antibody
Deglycosylation of the Bispecific Modified Common Light Chain DR5/FAP-Kappa-Lambda Antibody To confirm homogeneous preparation of the bispecific modified common light chain DR5/FAP-kappa-lambda antibody GA803_G27_H14D_001 by two sequential affinity chromatography steps final protein solution of is analyzed by LC-MS analyses. To remove heterogeneity introduced by carbohydrates the bispecific modified common light chain DR5/FAP-kappa-lambda antibody is treated with PNGaseF. Therefore the pH of the protein solution is adjusted to pH7.0 by adding 2 μl 2 M Tris to 20 μg protein with a concentration of 0.5 mg/ml. 0.8 μg IdeS is added and incubated for 68 h at 25° C.

LC-MS Analysis of Deglycosylated Bispecific Modified Common Light Chain DR5/FAP-Kappa-Lambda Antibody (on Line Detection)

The LC-MS method is performed on an Agilent HPLC 1200 coupled to a TOF 6441 mass spectrometer (Agilent). The chromatographic separation is performed on a Macherey Nagel Polysterene column; RP1000-8 (8 μm particle size, 4.6×250 mm; cat. No. 719510). Eluent A is 5% acetonitrile and 0.05% (v/v) formic acid in water, eluent B is 95% acetonitrile, 5% water and 0.05% formic acid. The flow rate is 1 ml/min, the separation is performed at 40° C. and 7 μg (15 μl) of an antibody sample obtained with a treatment as described before.

TABLE 6

LC-MS eluent conditions

| Time (min.) | % B |
| --- | --- |
| 0.5 | 15 |
| 10 | 60 |
| 12.5 | 100 |
| 14.5 | 100 |
| 14.6 | 15 |
| 16 | 15 |
| 16.1 | 100 |

During the first 4 minutes the eluate is directed into the waste to prevent the mass spectrometer to prevent the mass spectrometer from salt contamination. The ESI-source was running with a drying gas flow of 12 l/min, a temperature of 350° C. and a nebulizer pressure of 60 psi. The MS spectra are acquired using a fragmentor voltage of 350 V and a mass range 700 to 3200 m/z in positive ion mode using. MS data are acquired by the instrument software from 4 to 17 minutes.

Figure 4:
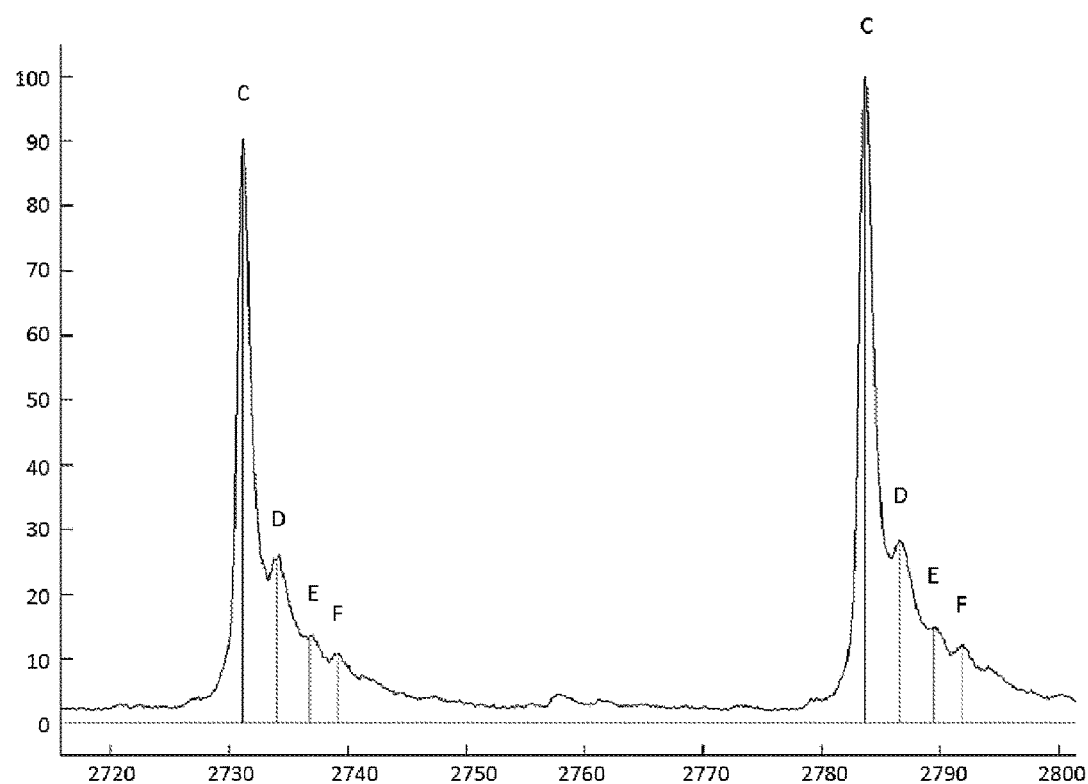
FIG. 4 Homogeneous preparation was confirmed by LC-MS using the anti-FAP and anti-DR5 bispecific antibody <FAP(3C6)[CLλ]-DR5(8E11)[CLκ]> as example. The main peak at 144697.1 Da corresponds to the correct molecular weight of the desired antibody molecule with two oxidation sites. Antibody molecules comprising either two kappa or two lambda light chains were not detected in LC-MS.

Results:

Homogeneous preparation is shown in FIG. 4 by LC-MS for the bispecific modified common light chain DR5/FAP-kappa-lambda antibody 3C6/8E11 as an example. The main peak at 144697.1 Da corresponds to the correct molecular weight of the protein with 2 oxidation sites Molecules carrying either two kappa or two lambda light chains are not detected in LC-MS (FIG. 4).

Example 5

Analyses of Simultaneous Binding to Two Different Antigens of the Bispecific Modified Common Light Chain DR5/FAP-Kappa-Lambda Antibody by Surface Plasmon Resonance All surface plasmon resonance (SPR) experiments are performed on a Biacore® T100 at 25° C. with HBS-EP as running buffer (0.01 M HEPES pH 7.4, 0.15 M NaCl, 3 mM EDTA, 0.005% Surfactant P20, Biacore, Freiburg/Germany).

Figure 5:
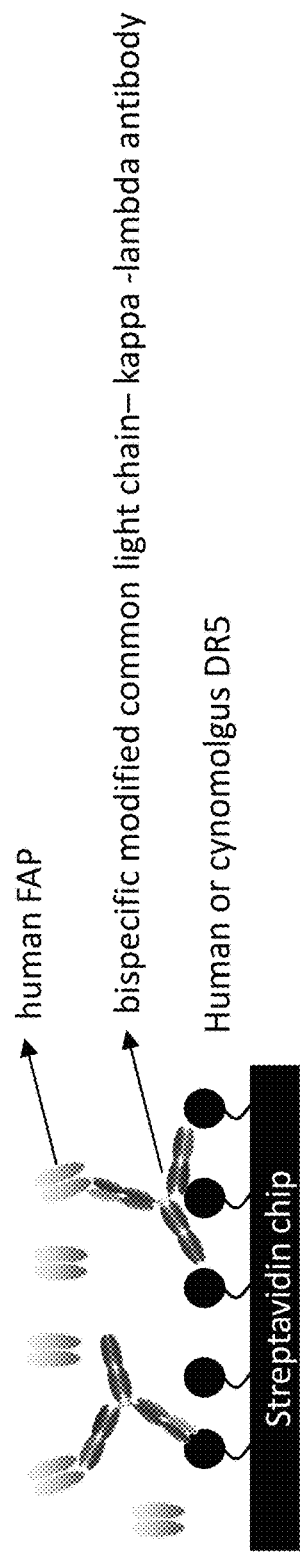
FIG. 5 A schematic illustration depicting the assay set-up for the detection of simultaneous binding to the two different antigens of a bispecific antibody, which specifically binds to DR5 and FAP, by surface plasmon resonance. Human or cynomolgus DR5 is coupled to a Streptavidin chip and used for immobilization of the bispecific antibody, while unbound human FAP is used assessment of antigen binding to FAP.

Simultaneous binding of the bispecific modified common light chain DR5/FAP-kappa-lambda antibody (GA803_G25_H14D_001) to the tumor antigen FAP and the human Death Receptor 5 (DR5) is performed by direct coupling of app. 120 resonance units (RU) of biotinylated human and cynomolgus DR5 on a Streptavidin chip (Biacore, Freiburg/Germany). A schematic drawing is shown in FIG. 5. Bispecific modified common light chain DR5/FAP-kappa-lambda antibody (GA803_G25_H14D_001) is captured for 90 s at 150 nM. Human FAP is passed subsequently at a concentration of 500 nM with a flowrate of 30 μl/min for 90 s. Dissoziation is measured for 60 s. Surface is regenerated by injection of 10 mM glycine, pH1.5 for 30 s.

Bulk refractive index differences are corrected for by subtracting the response obtained on reference flow cell where the recombinant human FAP is flown over a surface without captured bispecific modified common light chain DR5/FAP-kappa-lambda antibody.

Results

Figure 6:
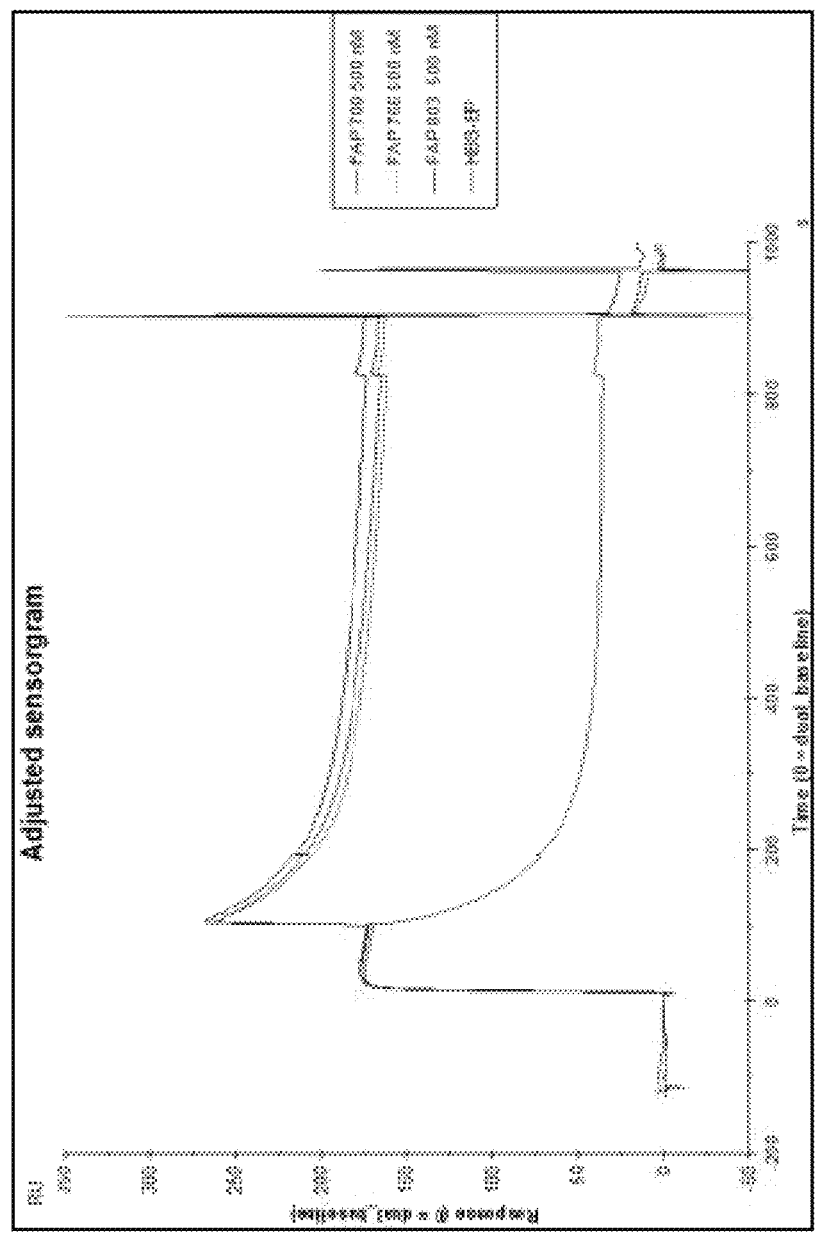
FIG. 6 An exemplary sensogramm, which is characteristic for the detection of simultaneous binding of the bispecific antibody according to the invention, which specifically binds to DR5 and FAP. Surface plasmon resonance measurements confirmed that the bispecific antibody according to the invention is capable of binding both antigens simultaneously (exemplary image of the sensogram received by analysis of the <FAP(3C6)[CLλ]-DR5(2A11)[CLκ]> bispecific antibody (specimen identifier GA803_G25_H14D_001).

Surface plasmon resonance measurement confirmed that the bispecific modified common light chain DR5/FAP-kappa-lambda antibody (GA803_G25_H14D_001) is able to bind both antigens simultaneously (shown in FIG. 6)

Example 6

Figure 7:
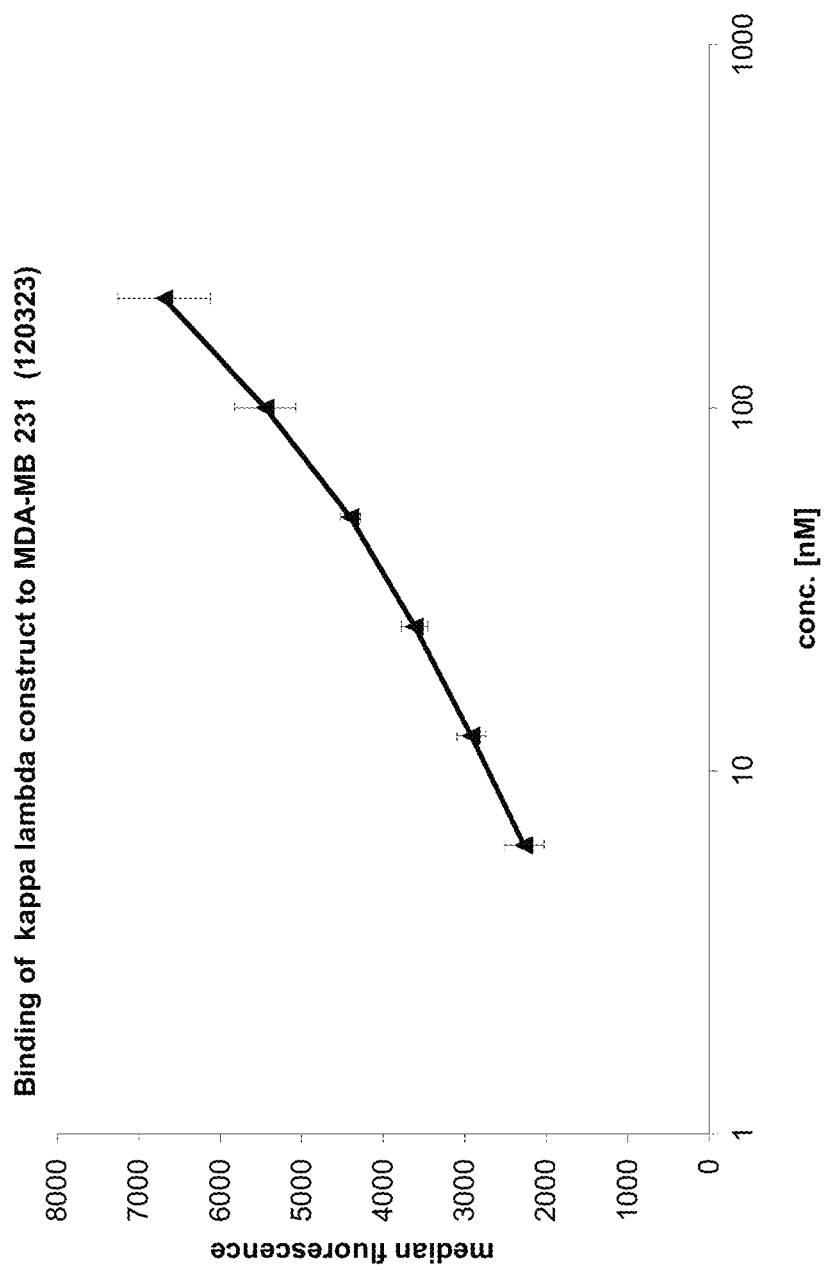
FIG. 7 Results from cell surface binding studies. Binding of the bispecific antibody according to the invention, which specifically binds to DR5 and FAP, to its antigen DR5 was assessed in cell binding studies using the DR5 expressing MDA-MB 231 tumor cell line by subsequent FACS analysis. Depicted is the result of the binding studies using the <FAP(3C6)[CLλ]-DR5(2A11)[CLκ]> bispecific antibody (specimen identifier GA803_G25_H14D_001). The constructs bind to MDA-MB 231 cells in a concentration dependent manner.

Cell Surface Binding of the Bispecific Modified Common Light Chain DR5/FAP-Kappa-Lambda Antibody Binding of human bispecific modified common light chain DR5/FAP-kappa-lambda antibody to cells of a DR5-expressing MDA-MB 231 tumor cell line and to cells of a FAP.expressing fibroblast cell line GM05389 was measured by FACS. As control another tetravalent bispecific DR5/FAP antibody construct containing the same binders was used. Briefly, 0.2 Mio cells per well in a 96 well round bottom plate were incubated with 40 μl of the indicated concentration of the constructs for 30 min at 4° C. Unbound construct was removed by washing the cells with PBS containing 0.1% BSA. Bound constructs were detected with Dylight649-conjugated AffiniPure F(ab')2 Fragment goat anti-human IgG Fcg Fragment Specific secondary antibody (Jackson ImmunoResearch #109-496-098; working solution 1:50 in PBS, 0.1% BSA). After 30 min incubation at 4° C. unbound antibody was removed by washing and cells were fixed using 1% PFA. Cells were analyzed using BD FACS Cantoll (Software BD DIVA). Results are shown in FIGS. 7 and 8. Binding of bispecific modified common light chain DR5/FAP-kappa-lambda antibody GA803_G25_H14D_001 was tested on DR5 positive MDA-MB 231 cells. The construct binds in a concentration dependent manner to MDA-MB 231 cells (FIG. 7).

Binding of bispecific modified common light chain DR5/FAP-kappa-lambda antibody GA803_G25_H14D_001 was tested on FAP positive GM05389 fibroblasts. The construct binds in a concentration dependent manner to GM05389 cells (FIG. 8).

Example 7

Apoptosis Assay

Apoptosis induction of human bispecific modified common light chain DR5/FAP-kappa-lambda antibody was measured using Cell Death Detection ELISAplus (Roche Applied Science #11774425001) in a co-culture assay. Briefly, 10,000 FAP expressing cells GM05389 were seeded in a 96well flat bottom cell culture plate and incubated overnight in an incubator. On the next day the diluted constructs were added at the indicated concentrations and incubated 10 min to allow binding of the antibodies. Then 10,000 apoptosis sensitive MDA-MB 231 tumor cells were added to the plates. As negative control apoptosis induction is tested in the absence of GM05389. After 24 h of incubation Cell Death Detection ELISA was performed as described in the manufacturer's instructions. Results are shown in FIG. 9. Apoptosis induction of three bispecific modified common light chain DR5/FAP-kappa-lambda antibodies with different DR5 binders was tested on MDA-MB 231 in the absence or presence of FAP expressing fibroblasts (GM05389). All constructs are able to induce specific apoptosis in the presence of FAP.

What is claimed is:

1. A multispecific antibody, comprising:
   (a) a first modified light chain, wherein the first modified light chain comprises in C-terminal to N-terminal direction:
      a constant light chain domain of kappa isotype (CLκ); and
      a variable heavy chain domain (VH$_1$) derived from an antibody which specifically binds to a first antigen;
   (b) a second modified light chain, wherein the second modified light chain comprises in C-terminal to N-terminal direction:
      a constant light chain domain of lambda isotype (CLλ); and
      a variable heavy chain domain (VH$_2$) derived from an antibody which specifically binds to a second antigen; and
   (c) two modified heavy chains, wherein each modified heavy chain comprises in C-terminal to N-terminal direction:
      heavy chain constant domains 3 and 2 (CH3 and CH2);
      a hinge region;
      a heavy chain constant domain 1 (CH1); and
      a light chain variable domain (VL),
         wherein the VL in one of the two modified heavy chains and the VL in the other of the two modified heavy chains are identical,
   wherein the first modified light chain of (a) pairs with one of the two modified heavy chains to form a first antigen binding site which specifically binds to the first antigen, and
   wherein the second modified light chain of (b) pairs with the other of the two modified heavy chains to form a second antigen binding site which specifically binds to the second antigen.

2. The multispecific antibody according to claim 1, wherein the antibody is a bivalent, bispecific antibody.

3. The multispecific antibody according to claim 1, wherein the antibody is of IgG class.

4. The multispecific antibody according to claim 1, wherein the antibody is of IgG1 or IgG4 subclass.

5. A pharmaceutical composition comprising the multispecific antibody according to claim 1 and at least one pharmaceutically acceptable excipient.

6. A pharmaceutical composition comprising the multispecific antibody according to claim 2 and at least one pharmaceutically acceptable excipient.

7. A pharmaceutical composition comprising the multispecific antibody according to claim 3 and at least one pharmaceutically acceptable excipient.

8. A pharmaceutical composition comprising the multispecific antibody according to claim 4 and at least one pharmaceutically acceptable excipient.

9. A nucleic acid encoding a multispecific antibody according to claim 1.

10. An expression vector containing a nucleic acid that encodes the multispecific antibody of claim 1.

11. A prokaryotic or eukaryotic host cell comprising an expression vector according to claim 10.

12. A method for the preparation of a multispecific antibody according to claim 1, comprising the steps of
   a) transforming a host cell with expression vectors comprising nucleic acid molecules encoding a multispecific antibody according to claim 1;
   b) culturing the host cell under conditions that allow synthesis of said multispecific antibody molecule; and
   c) recovering said multispecific antibody molecule from said culture.

* * * * *